(12) United States Patent
Boutelle et al.

(10) Patent No.: US 11,035,872 B2
(45) Date of Patent: Jun. 15, 2021

(54) MICROFLUIDIC FLOW CONTROLLER, FLUID ANALYSIS APPARATUS, ANALYSIS MODULE AND METHODS

(71) Applicant: IP2IPO Innovations Limited, London (GB)

(72) Inventors: Martyn Gordon Boutelle, London (GB); Michelle Louise Rogers, London (GB); Chi Leng Leong, London (GB); Sally Gowers, London (GB)

(73) Assignee: IP2IPO Innovations Limited, London (GB)

( * ) Notice: Subject to any disclaimer, the term of this patent is extended or adjusted under 35 U.S.C. 154(b) by 475 days.

(21) Appl. No.: 15/576,684

(22) PCT Filed: May 25, 2016

(86) PCT No.: PCT/GB2016/051511
§ 371 (c)(1),
(2) Date: Nov. 22, 2017

(87) PCT Pub. No.: WO2016/189302
PCT Pub. Date: Dec. 1, 2016

(65) Prior Publication Data
US 2018/0136247 A1 May 17, 2018

(30) Foreign Application Priority Data
May 26, 2015 (GB) ...................... 1508950

(51) Int. Cl.
*G01N 35/10* (2006.01)
*A61B 5/145* (2006.01)
(Continued)

(52) U.S. Cl.
CPC ..... *G01N 35/1097* (2013.01); *A61B 5/14525* (2013.01); *A61B 5/14532* (2013.01);
(Continued)

(58) Field of Classification Search
CPC ...... B01L 3/50; B01L 3/5055; B01L 2200/04; B01L 2300/043; B01L 2300/044;
(Continued)

(56) References Cited

U.S. PATENT DOCUMENTS 5,958,199 A 9/1999 Miyamoto et al.
6,413,396 B1 7/2002 Yang et al.
(Continued)

FOREIGN PATENT DOCUMENTS

CN 203324287 U 12/2013
CN 103822944 A 5/2014
(Continued)

OTHER PUBLICATIONS

International Search Report and Written Opinion dated Nov. 2, 2016 for International Application No. PCT/GB2016/051511, filed on May 25, 2016 (16 pages).
(Continued)

*Primary Examiner* — Lore R Jarrett
(74) *Attorney, Agent, or Firm* — Perkins Coie LLP

(57) ABSTRACT

A microfluidic flow controller for receiving analyte fluid and calibration fluids wherein the flow controller is configured to switch between (i) an analysis mode in which analyte fluid is passed to an analysis module and (ii) a calibration mode in which the analyte fluid is passed to an alternative destination and calibration fluid is passed to the analysis module, thereby maintaining flow rate of analyte fluid from a source and maintaining a steady flow rate of fluid through the analysis module in both analysis mode and calibration mode. The flow controller may vary the ration of multiple calibration fluids during a calibration mode. Means for accurately positioning sensors within a flow conduit of the analysis module is also described. Sensors are also described for use with or without the microfluidic flow controller for
(Continued)

the detection of metabolites and molecules. The sensors may or may not comprise enzymes and may be used with a sensing reagent, also described.

22 Claims, 33 Drawing Sheets

(51) Int. Cl.
*B01L 3/00* (2006.01)
*G01N 35/00* (2006.01)
*C12Q 1/00* (2006.01)
*C12Q 1/54* (2006.01)
*G01N 27/327* (2006.01)

(52) U.S. Cl.
CPC ...... *A61B 5/14546* (2013.01); *B01L 3/50273* (2013.01); *B01L 3/502707* (2013.01); *B01L 3/502715* (2013.01); *B01L 3/502738* (2013.01); *B01L 3/502746* (2013.01); *C12Q 1/005* (2013.01); *C12Q 1/006* (2013.01); *C12Q 1/54* (2013.01); *G01N 27/3274* (2013.01); *G01N 35/00693* (2013.01); *A61B 2560/0223* (2013.01); *A61B 2562/028* (2013.01); *B01L 2200/025* (2013.01); *B01L 2200/027* (2013.01); *B01L 2200/06* (2013.01); *B01L 2200/14* (2013.01); *B01L 2200/148* (2013.01); *B01L 2300/0609* (2013.01); *B01L 2300/0636* (2013.01); *B01L 2300/0645* (2013.01); *B01L 2400/0478* (2013.01); *B01L 2400/0633* (2013.01); *G01N 2035/00306* (2013.01)

(58) Field of Classification Search
CPC ....... B01L 2300/0636; B01L 2300/087; B01L 2300/123; B01L 2400/0487; B01L 3/502746; B01L 3/502707; B01L 3/502715; B01L 3/50273; B01L 3/502738; B01L 2200/025; B01L 2200/027; B01L 2200/06; B01L 2200/14; B01L 2300/0609; B01L 2300/0645; B01L 2400/0478; B01L 2400/0633; B01L 2200/148; B01L 2400/0457; B01L 3/5027; Y10T 156/1051; Y10T 29/4998; G01N 35/1097; G01N 2035/00306; G01N 27/3274; G01N 35/00693; C12Q 1/005; C12Q 1/006; C12Q 1/54; F15C 1/02; F15C 1/04; F16K 99/0001; A61B 5/14532; A61B 5/14546; A61B 2562/028; A61B 2560/0223; A61B 5/14525
See application file for complete search history.

(56) References Cited

U.S. PATENT DOCUMENTS

| | | | |
|---|---|---|---|
| 7,087,149 | B1 | 8/2006 | Muguruma et al. |
| 2001/0017269 | A1 | 8/2001 | Heller et al. |
| 2002/0025580 | A1 | 2/2002 | Vadgama et al. |
| 2002/0042090 | A1 | 4/2002 | Heller et al. |
| 2002/0090738 | A1 | 7/2002 | Cozzette et al. |
| 2003/0104119 | A1 | 6/2003 | Wilson et al. |
| 2003/0135100 | A1 | 7/2003 | Kim et al. |
| 2004/0020771 | A1 | 2/2004 | Taniike et al. |
| 2004/0211666 | A1 | 10/2004 | Pamidi et al. |
| 2009/0156922 | A1 | 6/2009 | Goldberger et al. |
| 2010/0159600 | A1 | 6/2010 | Shin et al. |
| 2011/0098597 | A1* | 4/2011 | Wu ............. B01L 3/5027 600/573 |
| 2011/0213230 | A1 | 9/2011 | Lindgren et al. |
| 2013/0041242 | A1 | 2/2013 | Karlsson et al. |
| 2014/0356849 | A1 | 12/2014 | Wikswo et al. |

FOREIGN PATENT DOCUMENTS

| | | | | |
|---|---|---|---|---|
| CZ | 27863 | U1 | 3/2015 | |
| EP | 2011438 | A2 | 1/2009 | |
| WO | 9802569 | A1 | 1/1998 | |
| WO | 9820332 | A1 | 5/1998 | |
| WO | 2013086505 | A1 | 6/2013 | |
| WO | WO2013086505 | A1 * | 6/2013 | ............ G01N 37/00 |
| WO | 2014041190 | A1 | 3/2014 | |
| WO | 2014081840 | A1 | 5/2014 | |
| WO | 2015010545 | A1 | 1/2015 | |

OTHER PUBLICATIONS

UK Exam Report dated Aug. 29, 2018 for UK Patent Application No. 1508950.1, filed on May 26, 2015 (4 pages).
UK Combined Search and Examination Report dated Nov. 23, 2015 for GB Patent Application No. 1508950.1, filed on May 26, 2015 (6 pages).
UK Amended Search Report dated Aug. 5, 2016 for GB Patent Application No. 1508950.1, filed on May 26, 2015 (2 pages).
Koh et al., "Fabrication of Nitric Oxide-Releasing Porous Polyurethane Membranes-Coated Needle-type Implantable Glucose Biosensors," Analytical Chemistry, 85 (21), 10488-10494, DOI: 10.1021/ac402312b, 2013.
Trzebinski et al., "Microfluidic Device to Investigate Factors Affecting Performance in Biosensors Designed for Transdermal Applications," Cass AE, Lab Chip.,12(2):348-52. doi: 10.1039/c11c20885c. Epub Nov. 30, 2011, Jan. 21, 2012.
Rogers et al., "Real-Time Clinical Monitoring of Biomolecules," Annual Review of Analytical Chemistry, 6:1, 427-453 doi: 10.1021/cn400047x, 2013.
Yang et al., "Needle-Type Lactate Biosensor," Biosens Bioelectron., 14(2), pp. 203-210, Feb. 1999.
Matzeu et al., "Advances in Wearable Chemical Sensor Design for Monitoring Biological Fluids," Sensors and Actuators B Chem., 211, pp. 403-418, 2015.
Diamond et al., "Wireless Sensor Networks and Chemo-/Biosensing," Chemical Review, 108, pp. 652-679, 2008.
Windmiller et al., "Wearable Electrochemical Sensors and Biosensors: A Review," Electroanalysis, 25, pp. 29-46, 2013.
Woderer et al., "Continuous Glucose Monitoring in Interstitial Fluid Using Glucose Oxidase-Based Sensor Compared to Established Blood Glucose Measurement in Rats," Analytica Chimica Acta, 581, pp. 7-12, 2007.
Facchinetti et al., "Reconstruction of Glucose in Plasma from Interstitial Fluid Continuous Glucose Monitoring Data: Role of Sensor Calibration," Journal of Diabetes Science and Technology, vol. 1, issue 5, pp. 617-623, 2007.
Curto et al., "Real-Time Sweat Ph Monitoring Based on a Wearable Chemical Barcode Micro-Fluidic Platform Incorporating Ionic Liquids," Sensors and Actuators B: Chemical, 171-172, pp. 1327-1334, 2012.
Jia et al., "Electrochemical Tattoo Biosensors for Real-Time Noninvasive Lactate Monitoring in Human Perspiration," Analytical Chemistry, 85, pp. 6553-6560, 2013.
Iguchi et al., "A Flexible and Wearable Biosensor for Tear Glucose Measurement," Biomed Microdevices, 9, pp. 603-609, 2007.
Yoda et al., "Analysis of Glycolysis Relevant Compounds in Saliva by Microbiosensors," Annals New York Academy of Sciences, 864, pp. 600-604, 1998.
Mannoor et al., "Graphene-Based Wireless Bacteria Detection on Tooth Enamel," Nature Communications, 3, 763, pp. 1-8, 2012.
Krustrup et al., "Muscle and Blood Metabolites during a Soccer Game: Implications for Sprint Performance," J. Med. Sci. Sports Exerc., 38, pp. 1165-1174, 2006.
Watson, "In Vivo Measurements of Neurotransmitters by Microdialysis Sampling," Analytical Chemistry, 78, pp. 1391-1399, 2006.

(56) References Cited

OTHER PUBLICATIONS

Parkin et al., "Resolving Dynamic Changes in Brain Metabolism Using Biosensors and On-Line Microdialysis," Trends in Analytical Chmistry, vol. 22, No. 9., pp. 487-497, 2003.
Nandi et al., "Recent Trends in Microdialysis Sampling Integrated with Conventional and Microanalytical Systems for Monitoring Biological Events: A Review," Analytica Chemica Acta, 651, pp. 1-14, 2009.
Rogers, M. L., et al., "Online Rapid Sampling Microdialysis (rsMD) Using Enzymebased Electroanalysis for Dynamic Detection of Ischaemia During Free Flap Reconstructive Surgery," Analytical and Bioanalytical Chemistry, vol. 405, 11, pp. 3881-3888, 2013.
Rogers et al., "Continuous Online Microdialysis Using Microfluidic Sensors: Dynamic Neurometabolic Changes During Spreading Depolarization," ACS Chemical Neuroscience, 4, pp. 799-807, 2013.
Birke-Sorensen, "Detection of Postoperative Intestinal Ischemia in Small Bowel Transplants," Journal of Transplantation, vol. 2012, Article ID 970630, (6 pages), 2012.
Wang et al., "Improved Temporal Resolution for In Vivo Microdialysis by Using Segmented Flow," Analytical Chemistry, vol. 80, pp. 5607-5615. 2008.
Sun et al., "Label Free Screening of Enzyme Inhibitors at Femtomole Scale Using Segmented Flow Electrospray Ionization Mass Spectrometry," Analytical Chemistry, 84, pp. 5794-5800, 2012.
Nandi et al., "Development of a PDMS-Based Microchip Electrophoresis Device for Continuous Online In Vivo Monitoring of Microdialysis Samples," Electrophoresis, 31, pp. 1414-1422, 2010.
Lucca et al., "Separation of Natural Antioxidants Using PDMS Electrophoresis Microchips Coupled with Amperometric Detection and Reverse Polarity," Electrophoresis, 35, pp. 3363-3370, 2014.
Lunte et al., "The Development of a Miniaturized Wireless Microdialysis-Microchip Electrophoresis System for In Vivo Monitoring of Drugs and Neurotransmitters in Awake and Freely Moving Sheep," 14th International Conference on Miniaturized Systems for Chemistry and Life Sciences, pp. 1535-1537, 2010.
Erkal et al., "3D Printed Microfluidic Devices with Integrated Versatile and Reusable Electrodes," Lab Chip, 14(12), pp. 2023-2032, 2014.
Snowden et al., "Fabrication of Versatile Channel Flow Cells for Quantitative Electroanalysis Using Prototyping," Analytical Chmistry, vol. 82, pp. 3124-3131, 2010.
Anderson et al., "A 3D Printed Fluidic Device that Enables Integrated Features," Analytical Chemistry, vol. 85, pp. 5622-5626, 2013.
Patel et al., "ATP Microelectrode Biosensor for Stable Long-Term In Vitro Monitoring from Gastrointestinal Tissue," Biosensors and Bioelectronics, 26, pp. 2890-2896, 2011.
Viggiano et al., "Reconstruction of Field Excitatory Post-Synaptic Potentials in the Dentate Gyrus from Amperometric Biosensor Signals," Journal of Neuroscience Methods, 206, pp. 1-6, 2012.
Vasylieva et al., "Covalent Enzyme Immobilization by Poly (Ethylene Glycol) Diglycidyl Ether (PEGDE) for Microelectrode Biosensor Preparation," Biosensor and Bioelectronics, 26, pp. 3993-4000, 2011.
Feuerstein et al., "Practical Methods for Noise Removal: Applications to Spikes, Nonstationary Quasi-Periodic Noise, and Baseline Drift," Analytical Chemistry, 81, pp. 4987-4994, 2009.
Heinonen et al., "Organ-Specific Physiological Responses to Acute Physical Exercise and Long-Term Training in Humans," Physiology (Bethesda, Md.), vol. 29(6), pp. 421-436, 2014.
Timofeev et al., "Cerebral Extracellular Chemistry and Outcome Following Traumatic Brain Injury: a Microdialysis Study of 223 Patients," Brain, 134, pp. 484-494, 2011.
Kristensen et al., "Microdialysis: Characterisation of Haematomas in Myocutaneous Flaps by Use of Biochemical Agents," British Journal of Oral and Maxillofacial Surgery, 51, pp. 117-122, 2013.
Domschke et al., "Initial Clinical Testing of a Holographic Non-Invasive Contact Lens Glucose Sensor," Diabetes Technology & Therapeutics, vol. 8, No. 1, pp. 89-93, 2006.
Schultz et al., "Time-Resolved Microdialysis for In Vivo Neurochemical Measurements and Other Applications," Annual Review of Analytical Chemistry, vol. 1, pp. 627-661, 2008.
Deeba et al., "Use of Rapid Sampling Microdialysis for Intraoperative Monitoring of Bowel Ischemia," Diseases of the Colon & Rectum, vol. 51, 9, pp. 1408-1413, 2008.
Rogers et al., "Optimisation of a Microfluidic Analysis Chamber for the Placement of Microelectrodes," Physical Chemistry Chemical Physics, 13, pp. 5298-5303, 2011.
Taylor, G., "Dispersion of soluble matter in solvent flowing slowly through a tube", Proc. R. Soc. Lond. A. Math. Phys. Sci., 219, 186-203, 1953.
Kitson et al., "Configurable 3D-Printed Millifluidic and Microfluidic 'Lab on a Chip' Reactionware Devices," Lab Chip, vol. 12, No. 18, pp. 3267-3271, 2012.
Therriault et al., "Chaotic Mixing in Three-Dimensional Microvascular Networks Fabricated by Direct-Write Assembly," Nature Materials, 2, pp. 265-271, 2003.
Waldbaur et al., "Let There be Chip—Towards Rapid Prototyping of Microfluidic Devices: One-Step Manufacturing Processes," Analytical Methods, vol. 3, issue 12, 2681, 2011.
Bellander et al., "Consensus meeting on microdialysis in neurointensive care". Intensive Care Med, 30, pp. 2166-2169, 2004.
Boutelle MG, Fillenz M. "Clinical microdialysis: the role of on-line measurement and quantitative microdialysis". Acta Neurochir Suppl, 67, pp. 13-20, 1996.
Fabricius et al., "Cortical spreading depression and peri-infarct depolarization in acutely injured human cerebral cortex". Brain, 129, pp. 778-790, 2006.
Feuerstein et. al., "Dynamic metabolic response to multiple spreading depolarizations in patients with acute brain injury: an online microdialysis study". J Cereb Blood Flow Metab, 30, pp. 1343-1355, 2010.
Grieshaber et al., "Electrochemical Biosensors—Sensor Principles and Architectures". Sensors, 8, pp. 1400-1458, 2008.
Hartings et al., "Spreading depolarisations and outcome after traumatic brain injury: a prospective observational study". The Lancet Neurology 10, pp. 1058-1064, 2011.
Heller and Feldman, "Electrochemical Glucose Sensors and Their Applications in Diabetes Management". Chem. Rev., 108, pp. 2482-2505, 2008.
Hutchinson et al., "Clinical cerebral microdialysis: a methodological study". J Neurosurg, 93, pp. 37-43, 2000.
Paraiso et al., "Bioelectrochemical Detection of Alanine Aminotransferase for Molecular Diagnostic of the Liver Disease". Int. J. Electrochem. Sci., 9, pp. 1286-1297, 2014.
Revzin et al., "Glucose, lactate, and pyruvate biosensor arrays based on redox polymer/oxidoreductase nanocomposite thin-films deposited on photolithographically patterned gold microelectrodes". Sensors and Actuators, B 81, pp. 359-368, 2002.
Thevenot et al., "Electrochemical Biosensors: Recommended Definitions and Classification". Pure Appl. Chem., 71, 12, pp. 2333-2348, 1999.

* cited by examiner

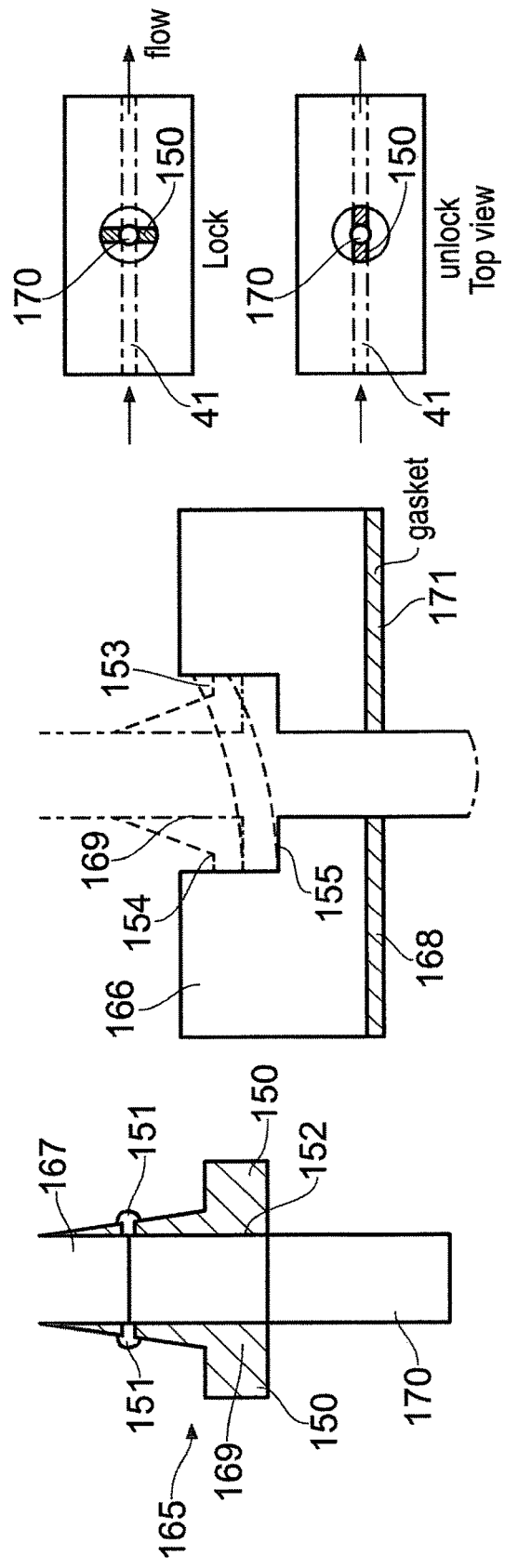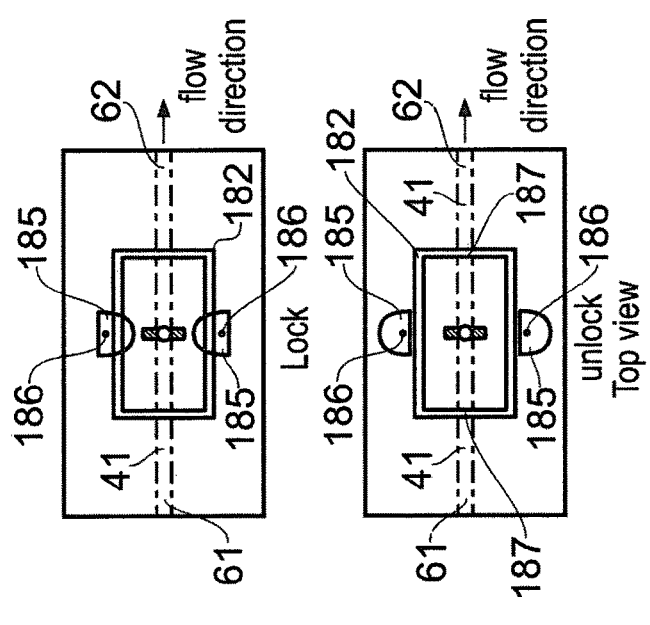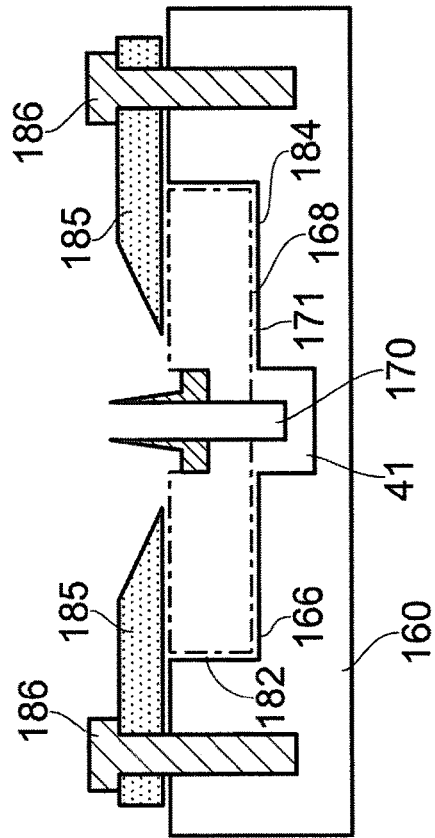
FIG. 10A
FIG 10B
FIG. 10C

MICROFLUIDIC FLOW CONTROLLER, FLUID ANALYSIS APPARATUS, ANALYSIS MODULE AND METHODS

FIELD OF THE INVENTION

The invention relates to the field of sensors and systems for measuring the amount of particular substances, for example metabolites, within a fluid sample, for example from a patient.

There are many situations in which real-time, continuous analysis of various substances within a subject are desired. One body of work concentrates on monitoring glucose levels in the blood, for example the monitoring of glucose levels in a diabetic, by either blood sampling probes or tissue sensors. For example, probes from Probe Scientific are commonly used as is the Abbots freestyle probe (Heller and Feldman, 2008 Rev Chem 108:2482-2505)

Another body of work looks at tissue levels of metabolites that are indicative of disease progression, local trauma or surgical procedures. One particular example of a need for such a technology is in the field of treatment of brain injury. Brain tissue is normally metabolically highly active and must consume large quantities of both glucose and oxygen to provide the necessary energy to maintain neuronal function. These energy substrates are provided by local blood flow which is tightly coupled to local neuronal activity. In brain tissue damaged by trauma, haemorrhage or local ischaemia energy demands are typically much greater.

However, local blood flow is typically reduced from normal and is unable to respond to dynamic increases in demand. This is because of local tissue swelling pressurises and pushes back against arterial blood pressure. In consequence the brain tissue is starved of energy, Within this damaged tissue the levels of key analytes such as glucose, lactate and pyruvate enables interpretation of tissue health in particular providing an assessment of the sufficiency of local energy supply, facilitating clinical judgment during critical periods of treatment. Sensors that can detect small concentration changes in these analytes need to be highly sensitive, fast, stable and selective. Ratios between lactate and pyruvate, or lactate and glucose are important metrics as they are less sensitive to artefacts in the data, such as that caused by changes in probe recovery. In particular, the lactate/glucose ratio has been shown to be an especially sensitive marker of tissue health, providing a clear indication as to whether tissue energy demands are being met.[15, 18, 21] In the brain, elevated lactate/pyruvate ratio has been shown to be predictive of patient outcomes.

A second example is provided by the detection of the onset of ischaemia in tissue such as the gut or flaps of muscle transferred as part of reconstructive surgery (Deeba S, Corcoles E P, Hanna B G, Pareskevas P, Aziz O, Boutelle M G, Darzi A. 2008. Use of rapid sampling microdialysis for intraoperative monitoring of bowel ischemia. Diseases of Colon and Rectum 51: 1408-13; and Rogers M L, Brennan P A, Leong C L, Cowers S A, Aldridge T, Mellor T K, Boutelle M G. 2013. Online rapid sampling microdialysis (rsMD) using enzyme-based electroanalysis for dynamic detection of ischaemia during free flap reconstructive surgery. Anal Bioanal Chem 405: 3881-8). Occlusion of blood flow, associated with the beginning of the period of ischaemia, results in a striking fall in tissue glucose and a rise in tissue lactate. This is most clearly seen as a rise in the lactate/glucose ratio, that is free from artefacts arising from surgical procedures. Successful reconnection of blood flow following anastomosis during microsurgery results in rapid restoration of normal levels.

In addition to the medical field, the clothing and sports industries has in recent years shown considerable interest in the development of wearable sensors to monitor a wide range of parameters, particularly with advances in body sensor networks (BSN),[1] providing the wearer with real-time information about their health and fitness.[2]

Developments in wearable sensors have mainly focused on the measurement of vital signs such as heart rate and electrocardiographic change, however, the ability to use chemo/bio-sensors to monitor additional physiological parameters can provide important information in addition to these physical parameters.[3,4] Amongst others, an area of particular interest in the use of wearable sensor technologies is sports. Access to real-time information can allow athletes to tailor their training to their individual characteristics, enabling them to assess their training effectiveness, to make adjustments and to track improvements in their performance.

Extensive research efforts have focused on the development of miniaturized on-body chemo/bio-sensors for the measurement of physiological analytes in different bodily fluids, such as interstitial fluid,[5,6] sweat,[7,8] tears[9,10] and saliva.[11,12] As with damaged tissue and brain injury, glucose and lactate are particularly attractive biomarkers to monitor, for a wide range of applications, as they provide information about tissue oxygenation levels. Lactate, in particular, has received much interest for sports monitoring. During intense exercise, tissue oxygen levels are insufficient for aerobic metabolism to meet the energy demands of the body. Instead, anaerobic metabolism occurs to meet these increased energy demands, leading to elevated lactate levels. Lactate can therefore be used as a measure of how hard the body is working, allowing athletes to modulate their effort accordingly, in order to train the body to increase its efficiency in clearing excess lactate or to avoid causing damage by over-training.

Commercially available lactate and glucose meters, which are also used for sports applications,[13] measure levels in blood. Although blood measurements provide important information about metabolite levels in the body, the use of finger-prick test strips has several limitations. For instance, in order to improve temporal resolution, blood samples have to be taken regularly, resulting in constant interruptions during the activity period. However, the main limitation of discrete sampling is the lack of temporal resolution, with the result that it is not possible to observe dynamic changes in metabolite levels.

Electrochemical sensors are one type of sensor used in to analyse metabolites and other biomolecules, and use amperometry, for example, to measure the concentration of chemical species in a solution. In addition to analysis of ions already present in solution, the use of enzymes to generate, for example $H_2O_2$, can be used to monitor the presence of other metabolites. For example lactate oxidase can be used to monitor the presence of lactate, via the formation of $H_2O_2$ which is then oxidised at, for example, a platinum electrode, resulting in generation of a current, and the current generated is proportional to the amount of $H_2O_2$ present, and therefore related to the amount of lactate in the sample. The final relationship does not have to be linear for the sensor to be considered useful.

Sensors in the form of Needle electrodes are described in Patel et al 2011 Biosensors and Bioelectronics 26: 2890-2896 for assessing ATP, for example. Needle electrodes are also described in, for example Koh et al (2013) Analyt Chem 85, 10488-10494; Viggianno et al (2012) J Neurosci Meth 206, 1-6.

Various coatings have been used for sensors with the aim of improving different aspects of sensor performance. As an example Poly-1-lysine has been used as hydrophilic coating for microfabricated electrodes, for example with polystyrene sulphonate (see Revzin et al (2002) Sensors and Actuators B 81, 359-368, which describes a two layer sensor; and Trzebinski et al (2012) Lab Chip 12: 348-352). Poly-1-lysine is not considered to form a hydrogel. Hydrogel coatings have been used, for example in Viggiano et al (2012) supra, which describes an electrode which comprises two layers.

Rogers et al (2013) ACS Chemical Neuroscience 4: 799-807 describes a glucose sensor comprising one layer, in which the enzyme was incorporated directly into an interference film consisting of poly(phenol).

Koh et al (2013) Analytical Chemistry 85: 10488-10494 describes an electrode in which the enzyme is located in a solid support, a sol-gel matrix, in a cavity in a platinum wire.

Paraiso et al (2014) Int J Electrochem Sci 9:1286-1297, discloses a two layer electrode for the detection of alanine aminotransferase by the detection of pyruvate.

US 2002/0042090 discloses a sensor comprising a glucose concentration-to-current transducing layer, an electrically insulating and glucose flux limiting layer, and optional horseradish peroxidase layer and biocompatible layer.

US 2013/0041242 discloses a sensor comprising an oxidase layer and a (separate) diffusion limiting membrane, for example a hydrogel.

Electrochemical sensors can be directly inserted into the tissue. However, after a short time this can render the sensor useless as the local area is depleted of oxygen and the electrochemical reaction ceases. This is potentially an issue for sensors such as a lactate sensor. However, the main issue with this type of set-up is that there is no good way to relate the in vivo calibration of the sensor in the tissue to the tissue concentration. Furthermore, as the sensitivity of the sensor changes with time, there is no ideal calibration obtained and therefore no reliable method of data interpretation.

An alternative is to employ the sensor on an extracellular composition using microdialysis. As the sample is freshly taken from the subject for each assay and moved through oxygen permeable tubing before analysis outside of the tissue, oxygen depletion is not an issue. Alternatively a small sample may be taken using ultrafiltration (ie vacuum applied to a stable membrane), the flow rates are then typically nanolitres per min.

Classical microdialysis consists of a slow pump which pumps perfusate liquid chosen to match the ionic composition of the tissue extracellular fluid, a microdialysis probe implanted into the tissue of interest, and a collection vial. In a clinical environment the vial is taken by clinical staff every 1-2 hours and placed in a central analyser where the levels of multiple key chemical biomarkers are determined. This places a significant time burden on the nursing staff and is subject to corruption of time sequences due to inadvertent errors in sample handling, for example late collection, mix-up in the time sequence or even loss of sample. Furthermore, samples every 1-2 hours can only reliably detect changes in dialysate concentrations that take place on a minimum 2-4 hour time scale.

Research in both human and animal models clearly show that important biomarker concentration changes take place on a much faster time scale than this. Faster sample collection takes place in research laboratories where staff are dedicated to this but it is not practical in a busy intensive care unit.

An improvement over taking a single sample multiple times is the use of online microdialysis, in which a continuous flow of liquid sample from the subject can be taken, and analysed at particular intervals or continuously (Boutelle M G, Fillenz M. 1996. Clinical microdialysis: the role of on-line measurement and quantitative microdialysis. Acta Neurochir Suppl 67: 13-20; and Parkin M C, Hopwood S E, Strong A J, Boutelle M G. 2003. Resolving dynamic changes in brain metabolism using biosensors and on-line microdialysis. TrAC Trends in Analytical Chemistry 22: 487-97; and Kristin N. Schultz and Robert T. Kennedy Annu. Rev. Anal. Chem. 2008. 1:627-61).

Microdialysis is an attractive technology for human in vivo monitoring, as commercial FDA-approved probes are available. Microdialysis combined with online analysis systems has been used to detect tissue health and ischemic events.[17-20]

Online measurement of dialysate levels is essential to monitoring key transient events that occur in damaged tissue. Microdialysis probes can be placed within the tissue to create a continuous liquid stream, however this method produces very small volumes per time, often sub-microlitre a minute. Microfluidics is very well placed to handle such tiny volumes accurately and reliably, but to be able to analyse the contents of such small volumes is highly problematic. For detection, electrochemistry provides an easily measurable output of either current or voltage related to concentration. In such small volumes, analysis using microelectrodes provides fast time responses with great sensitivity.

There is a natural synergy between microdialysis and microfluidic devices because high time resolution analysis of low volume flow rates requires very small internal volumes.[16,19,22]

Both microdialysis sampling and the analysis sensors are sensitive to flow rate. If the flow rate through the microdialysis probe varies, so too does the probes ability to collect (or recover) molecules from the surrounding tissue. To avoid artefacts in the data, the flow rate through the probe must remain constant. The sensors themselves will also produce artefacts if the flow rate across them changes due to changes in delivery of molecules to the sensor surface rather than concentration, as the current produced depends on the rate of delivery of electrons into the electrode surface.

There is therefore a need for improved sensors, for example metabolite sensors, that are capable of providing a continuous data stream from a sample in flow and that are highly sensitive. There is also need for an improved flow-control mechanism to enable the sensors to provide accurate data, ensuring the data is not influenced by differences in flow rate. The sensor will ideally be suitable for calibration at regular intervals. The sensors, systems and methods of the present invention address these problems.

According to one aspect, the present invention provides a microfluidic flow controller comprising:
  a fluid source connector for receiving analyte fluid;
  a first valve having: (i) an inlet coupled to the fluid source connector, (ii) a first outlet coupled to an analyte conduit for coupling to an analysis module; and (iii) a second outlet coupled to a drain conduit;
  a second valve coupled to a calibration fluid source inlet and having an outlet coupled to the analyte conduit;

a controller configured to substantially simultaneously:
a) switch the first valve between: (i) an analysis mode in which the inlet is fluidly coupled to the first outlet, and (ii) a divert mode in which the inlet is fluidly coupled to the second outlet; and
b) switch the second valve between (i) a standby mode in which delivery of calibration fluid to the analyte conduit is blocked and (ii) a calibration mode in which the valve is configured to deliver calibration fluid to the analyte conduit,
the flow controller being thereby configured to maintain a steady flow rate of fluid through the analyte conduit during both the analysis mode and the calibration mode.

The second valve may include a first port and a second port, the first port being coupled to a first pump and the second port being coupled to the calibration fluid source inlet, the second valve being configured such that in the standby mode the first and second ports are fluidly coupled to one another and in the calibration mode the pump is fluidly coupled to the analyte conduit.

The microfluidic flow controller may include a third valve coupled to a second calibration fluid source inlet and having an outlet coupled to the analyte conduit,
the controller being configured to switch the third valve between (i) a standby mode in which delivery of second calibration fluid to the analyte conduit is blocked and (ii) a calibration mode in which the valve is configured to deliver calibration fluid to the analyte conduit, the switching being substantially simultaneous with the switching of the first and second valves such that the standby modes of the second and third valves coincide and the calibration modes of the second and third valves coincide.

The third valve may include a first port and a second port, the first port being coupled to a second pump and the second port being coupled to a second calibration fluid source inlet, the third valve being configured such that in the standby mode the first and second ports are fluidly coupled to one another and in the calibration mode the second pump is fluidly coupled to the analyte conduit.

The first pump may be a piston pump and the controller may be further configured to activate the first pump to charge via the second valve second port when the second valve is in the standby mode and to discharge via the second valve outlet when the second valve is in the calibration mode. The second pump may be a piston pump and the controller may be further configured to activate the second pump to charge via the third valve second port when the third valve is in the standby mode and to discharge via the third valve outlet when the third valve is in the calibration mode. The second valve may be coupled to the calibration source inlet via a pump. The microfluidic flow controller may include an analysis module fluidly coupled to the analyte conduit. The microfluidic flow controller may include a first reservoir of calibration fluid coupled to the calibration fluid source inlet. The microfluidic flow controller may include a second reservoir of calibration fluid coupled to the second calibration fluid source inlet. The microfluidic flow controller may include a collection vessel fluidly coupled to the drain conduit for receiving analyte when the first valve is in the divert mode. The controller may be configured to periodically switch from the analysis mode to the calibration mode.

The microfluidic flow controller may include a flush valve coupled to a flush fluid source inlet and having an outlet coupled to the analyte conduit, the controller being further configured to switch the flush valve between (i) a standby mode in which delivery of flush fluid to the analyte conduit is blocked and (ii) a flush mode in which the flush valve is configured to deliver flush fluid to the analyte conduit,
the flow controller being thereby configured to enable a flush fluid to pass through the analyte conduit to clear gas bubbles and obstructions from the analyte conduit and from any analysis module coupled to the analyte conduit.

The flush valve may include a first port and a second port, the first port being coupled to a flush pump and the second port being coupled to the flush fluid source inlet,
the flush valve being configured such that in the standby mode the first and second ports are fluidly coupled to one another and in the flush mode the flush pump is fluidly coupled to the analyte conduit.

The microfluidic flow controller may include a reservoir of flush fluid coupled to the flush fluid source inlet.

The microfluidic flow controller may include a reagent valve coupled to a reagent fluid source inlet and having an outlet coupled to the analyte conduit, the controller being further configured to switch the reagent valve between (i) a standby mode in which delivery of reagent to the analyte conduit is blocked and (ii) an analysis mode in which the reagent valve is configured to deliver reagent to the analyte conduit.

The reagent valve may include a first port and a second port, the first port being coupled to a reagent pump and the second port being coupled to the reagent fluid source inlet,
the flush valve being configured such that in the standby mode the first and second ports are fluidly coupled to one another and in the analysis mode the flush pump is fluidly coupled to the analyte conduit,
the switching being substantially simultaneous with the switching of the first and second valves such that the analysis modes of the first valve and the reagent valve coincide and the divert mode of the first valve and the standby mode of the reagent valve coincide.

The microfluidic flow controller may include a reservoir of reagent coupled to the reagent fluid source inlet.

The controller may be configured to ensure that a combined flow rate of analyte fluid entering the analyte flow conduit from the fluid source connector and from the reagent valve during the analysis mode is matched to a flow volume of calibration fluid and reagent fluid entering the analyte flow conduit during the calibration mode.

According to another aspect, the invention provides a method of fluid monitoring comprising:
receiving an analyte fluid from an analyte fluid source into a microfluidic flow controller;
receiving a calibration fluid from a calibration fluid source into the microfluidic flow controller;
operating the microfluidic flow controller to alternatingly pass the analyte fluid and the calibration fluid to an analysis module so as to maintain a steady flow rate of fluid through the analysis module during both an analysis mode and a calibration mode.

The method may include maintaining a steady flow rate of analyte fluid from the analyte fluid source by operating the flow controller to alternatingly pass the analyte fluid to (i) the analysis module and (ii) a drain conduit.

The method may be performed using a microfluidic flow controller as defined above.

According to another aspect, the invention provides a microfluidic fluid analysis apparatus comprising:
a fluid source connector for receiving analyte fluid;
a first calibration source inlet for coupling to a first reservoir for a first calibration fluid;

a second calibration source inlet for coupling to a second reservoir for a second calibration fluid;
an analysis module configured to receive fluid for analysis;
a flow controller configured to (i) fluidly couple the fluid source connector to the analysis module during an analysis mode; and (ii) deliver the first and second calibration fluids to the analysis module during a calibration mode, the flow controller being further configured to vary the ratio of flow rates of the first and second calibration fluids to the analysis module during the calibration mode.

The flow controller may include a first pump for delivering said first calibration fluid and a second pump for delivering said second calibration fluid to the analysis module during the calibration mode. The microfluidic fluid analysis apparatus may include a first calibration fluid reservoir coupled to supply said first pump and a second calibration fluid reservoir coupled to supply said second pump. The flow controller may be configured to periodically implement a calibration routine comprising:
  operating the flow controller to deliver a first ratio of first and second calibration fluids to the analysis module and subsequently to deliver at least a second ratio of first and second calibration fluids, different from the first ratio, to the analysis module;
  and the apparatus may include a calibration processor configured to determine a calibration profile derived from the ratios of calibration fluids and consequential analysis outputs from the analysis module.

One of the first and second ratios may include a 100% proportion of one of the calibration fluids and a zero proportion of the other one of the calibration fluids.

The flow controller may be configured to implement the calibration routine periodically based on at least one predefined time interval. The flow controller may be configured to implement the calibration routine periodically based on a calibration profile slope. The flow controller may be configured to implement the calibration routine periodically based on a rate of change of calibration profile over time. The flow controller may be further configured to isolate the fluid source connector and the analysis module when the flow controller is in in the calibration mode.

The microfluidic fluid analysis apparatus may be configured to issue an alert signal based on the determined calibration profile, which indicates an expiry time of the analysis module.

According to another aspect, the invention provides a method of automatically calibrating a microfluidic fluid analysis apparatus comprising:
  receiving analyte fluid from an analyte fluid source into a microfluidic flow controller;
  receiving a first calibration fluid from a first calibration fluid source into the microfluidic flow controller;
  receiving a second calibration fluid from a second calibration fluid source into the microfluidic flow controller;
  operating the microfluidic flow controller to pass the analyte fluid to the analysis module during an analysis mode of operation;
  operating the microfluidic flow controller to pass the calibration fluids to the analysis module during a calibration mode of operation,
  during the calibration mode of operation, varying the ratio of the flow rates of the first and second calibration fluids passing to the analysis module.

The method may include determining a calibration profile derived from the ratios of calibration fluid flow rates and consequential analysis outputs from the analysis module.

The method may further include implementing a calibration routine periodically based on at least one predefined time interval. The method may include implementing the calibration routine periodically based on a calibration profile slope. The method may include implementing the calibration routine periodically based on a rate of change of calibration profile over time.

According to another aspect, the invention provides a microfluidic analysis module comprising:
  a flow conduit having an inlet and an outlet;
  an aperture in a lateral wall of the flow conduit between the inlet and the outlet;
  an engagement mechanism coupled to the lateral wall configured to receive an sensor holder;
  a sensor holder configured for removable engagement with the engagement mechanism of the lateral wall and having a needle sensor mount for positioning a needle sensor assembly therein to extend from a distal end of the sensor holder,
  the sensor holder being configured to enable adjustment of the extent to which a needle mounted therein extends through the aperture and into the flow conduit.

The needle sensor mount may comprise a longitudinal shaft extending therethrough for receiving a said needle sensor assembly and a retention mechanism for adjustably retaining the needle sensor assembly in a longitudinal position. The retention mechanism may comprise a grub screw. The engagement mechanism may comprise a bayonet mount or a screw thread mount. The microfluidic analysis module may include a needle sensor. The needle sensor may comprise a needle electrode. The needle sensor may comprise at least one sensor exposed at a distal end thereof, the needle having a tip extending distally of the at least one sensor by a distance equal to a portion of the diameter of the flow conduit. The distance may be set to place said at least one sensor within the central half portion of the flow conduit. The needle sensor may comprise plural said sensors positioned proximally of the needle tip, each of said plural sensors being proximal of the tip by a distance set to place the plural sensors within the central half portion of the flow conduit. The needle electrode may comprise an electrically conductive shaft and tip.

According to another aspect, the invention provides method of mounting a sensor within a microfluidic analysis module comprising:
  providing a flow conduit having an inlet and an outlet and an aperture in a lateral wall of the flow conduit between the inlet and the outlet, and an engagement mechanism coupled to the lateral wall configured to receive a sensor holder;
  disposing a needle sensor assembly into a needle sensor mount of the sensor holder such that a needle sensor of the needle sensor assembly extends from a distal end of the sensor holder;
  engaging the sensor holder with the engagement mechanism of the lateral wall;
  adjusting the extent to which the needle sensor extends through the sensor holder before and/or after engaging the sensor holder with the engagement mechanism of the lateral wall so as to adjust the extent to which the needle sensor extends through the aperture and into the flow conduit.

Adjusting may comprise adjusting the position of a sensor on the needle sensor such that it lies within the central half portion of the lateral cross-section of the flow conduit.

Throughout the present specification, reference to 'online' monitoring or analysis is intended to encompass systems in which electrochemical analysis is applied over a period of time on fluids flowing past the electrochemical sensors, providing a plurality of measurements during the period of time.

Throughout the present specification, references to 'microfluidic' are intended to encompass manipulation and analysis of small volumes of fluid at flow rates of less than a few tens of microlitres, or more preferably 10 microliters or less. Typical flow conduits may be in the size range 1 to 1000 microns in diameter/width, e.g. of cross-sectional area of about 1 micron$^2$ up to 1 mm$^2$, though smaller dimensions can be envisaged. Typical flow rates may lie in the range 1 to 10 microlitres per minute.

Flow Control

FIGS. 1 and 2 illustrate principles of operation of a microfluidic flow controller which is particularly configured to enable an analyte flow from a subject to be maintained and, contemporaneously, enable a calibration source to be switched in and out of circuit with an analysis module while enabling continuous analyte or calibration fluid flow through the analysis module.

Microfluidic flow controller 1 comprises a fluid source connector 2 for receiving a flow of fluid analyte from a suitable source S, such as a human patient undergoing online microdialysis by way of microdialysis probe P. Any suitable connection apparatus 3 including a fluid line from the probe P and source S may be used to couple the flow controller 1 to the source. A first valve 4 has: an inlet 4a coupled to the fluid source connector 2; a first outlet 4b which is coupled to an analyte conduit 5; and an second outlet 4c which is coupled to a drain conduit 6. The drain conduit 6 may be detachably coupled to a suitable collection vessel or receptacle 7 for receiving unused analyte which may be discarded or collected for alternative analysis.

A second valve 8 has: a first port 8a coupled to a first pump 9; a second port 8b coupled to a first calibration source inlet 10; and an outlet 8c coupled to the analyte conduit 5. A third valve 11 has: a first port 11a coupled to a second pump 12; a second port 11b coupled to a second calibration source inlet 13; and an outlet 11c coupled to the analyte conduit. The first and second calibration source inlets 10, 13 may be respectively coupled to suitable reservoirs 14, 15 of first and second calibration fluids. The reservoirs 14, 15 may, for example, be detachable sources or remote sources connected by fluid line or may be integrated into the flow controller 1 itself.

An analysis module 16 has an inlet 17 which is coupled to the analyte conduit 5 and may have an outlet 18 for coupling to a suitable outlet for fluid disposal, collection or recirculation, or even for passing through a further analysis module downstream of the analysis module 16. This latter option might not be possible if the downstream analysis module would be incompatible with output from the upstream analysis module, discussed later.

A controller 20 is operable to control the operation of the valves 4, 8, 11; the pumps 9, 12, and the analysis module 16.

In certain circumstances, it may be very important that a constant flow and a constant flow rate of analyte from the source S via the probe P is maintained. It may also be very important that a constant flow and a constant flow rate of fluid is maintained through the analysis module 16. For example, maintaining a constant flow rate through a microdialysis probe ensures there are no artefacts from changes in the probe's ability to collect and recover analytes from the surrounding tissue in patient source S, leading to changes in the dialysate concentration. Such artefactual transient changes in concentration can be masked in classical 1- or 2-hourly microdialysis samples yet represent a serious threat in dynamic on-line analysis modules with fast sensors and biosensors.

It may also be important to enable the analysis module 16 to be periodically calibrated by the introduction of one or more calibration fluids, without disrupting flow through the dialysis probe P itself. Variable or disturbed flow rates through the analysis module 16 may result in variable performance of electrodes in the analysis module and the ability to sense the desired analytes.

In a preferred arrangement, the controller 20 is configured to substantially simultaneously:

a) switch the first valve 4 between: (i) an analysis mode in which the inlet 4a is fluidly coupled to the first outlet 4b, and (ii) a divert mode in which the inlet 4a is fluidly coupled to the second outlet 4c; and b) switch the second valve 8 between (i) a standby mode in which delivery of calibration fluid to the analyte conduit 5 is blocked and (ii) a calibration mode in which the valve is configured to deliver calibration fluid to the analyte conduit 5 via outlet 8c.

In a similar manner, the controller 20 may also be configured to, substantially simultaneously with a) above, c) switch the third valve 11 between (i) a standby mode in which delivery of calibration fluid to the analyte conduit 5 is blocked and (ii) a calibration mode in which the valve is configured to deliver calibration fluid to the analyte conduit 5 via outlet 11c.

The flow controller 1 is thereby configured to maintain a steady flow rate of fluid through the analyte conduit 5 to the analysis module during both the analysis mode and the calibration mode. During the calibration mode, the flow controller may be operable to allow flow of both first and second calibration fluids into the analyte conduit 5, in any ratio including zero flow from the second valve 8 and 100% flow from the third valve 11, or zero flow from the third valve and 100% flow from the second valve, and any ratio in between.

During the calibration mode, the analyte flow from source S is diverted to the drain conduit 6 to maintain flow through the probe P.

In the analysis mode, the first valve 4 is operable to pass the analyte flow from source S to the analysis module 16 as shown by arrow 24a.

In the preferred configuration shown in FIGS. 1 and 2, the pumps 9, 12 are reciprocating pumps, e.g. piston pumps, which can be respectively charged from reservoirs 14, 15 when the calibration sources are isolated from the analyte conduit 5 (during the standby mode/analysis mode) and can be discharged to the analyte conduit 5 during the calibration mode. To achieve this, the second and third valves 8, 11 may be configured such that first and second ports 8a, 8b (or 11a, 11b) are fluidly connected during the standby mode, whereas first port 8a and outlet 8c (or 11a and 11c) are fluidly connected during the calibration mode. During the standby mode of the second valve 8, the pump 9 may be operated to charge its chamber from the first calibration source reservoir 14 as indicated by arrow 21a and during the calibration mode, the pump 9 may be operated to discharge its chamber to the analyte conduit 5 as indicated in FIG. 2 by arrow 22a. Similar operation of pump 12 and reservoir 15 may be effected as indicated by arrows 21b and 22b.

During the calibration mode, the calibration fluids from pumps 9, 12 may be combined at interconnector 23 and flow to the analyte conduit 5 as shown by arrow 25, while the analyte flow from fluid source connector 2 is diverted to the receptacle 7 as indicated by arrow 24b.

This configuration allows analyte, such as microdialysate, to be switched to and from the analysis module 16, without disrupting or stopping the flow through the microdialysis probe P and the added capability of allowing automatic collection of the dialysate in a receptacle 7 for more classical (off-line) sample-based analysis during autocalibration.

In a general aspect, it can be seen that the system described in connection with FIGS. 1 and 2, and the variations thereof, is capable of effecting a method of fluid monitoring which includes: receiving an analyte fluid from an analyte fluid source S, e.g. via a dialysis probe P; receiving one or more calibration fluids from one or more calibration fluid sources 9, 14; 12, 15; and alternatingly passing the analyte fluid and the calibration fluid to an analysis module 16 so as to maintain a steady flow rate of fluid through the analysis module during both an analysis mode and a calibration mode.

The system exemplified in FIGS. 1 and 2 may be configured as a closed system ensuring that no air bubbles are introduced during switching. Air bubbles can be very disruptive to electrochemical recordings. Therefore, switching between analysis mode and calibration mode is preferably implemented sufficiently quickly and cleanly to avoid any generation of bubbles or other disruptions in the flow rates.

Various modifications may be made to the flow controller as described with reference to FIGS. 1 and 2. For example, one, two or more calibration fluid pumps and calibration fluid supplies may be used. The pumps 9, 12 may be non-reciprocating pumps (e.g. not piston pumps requiring a separate charge phase and discharge phase as discussed above) and may be in series with their respective reservoirs 14, 15 and valves 8, 11 for single direction pumping towards the respective valves 8, 11. In this case, valves 8, 11 may be configured as simple on-off valves separating the respective pumps 8, 11 from the analyte conduit 5. The three-port valves 4, 8, 11 of FIGS. 1 and 2 can also be configured with 'off' positions in which all flows are stopped, if desired.

Some or all of the valves 4, 8, 11, analyte conduit 5, pumps 9, 12, reservoirs 14, 15, fluid source connector 2, interconnectors 23, 26, analysis module 16 and conduits therebetween may be integrated onto a unitary substrate or comprise discrete parts which may be readily plugged into or attached to a common substrate. Some parts may be disposable plug-in units such as the analysis module 16, reservoirs 14, 15 etc. The analysis module 16 may comprise a monolithic device or 'chip'. Preferably, in a plug-in design, all consumable parts may be easily replaced by a non-expert user. The substrate and parts thereon may be fabricated using additive manufacturing techniques such as 3D printing for highly accurate dimensional control.

Various modifications to the microfluidic flow controller of FIGS. 1 and 2 can be envisaged. With reference to FIG. 11, an analyte conduit flushing arrangement may be added. In the example arrangement of FIG. 11 a flush pump 120 and flush reservoir 122 are coupled to the analyte conduit 5 by way of a valve 121 and a flush conduit 123 which joins the analyte conduit via the interconnectors 27, 26. The flush pump 120 may operate in the same manner as the calibration fluid pumps 9, 12, e.g. to charge the pump 120 from reservoir 122 when the pump is isolated from the analyte conduit 5, and to discharge the pump 120 to the flush conduit 123 and the analyte conduit 5 during a flushing operation.

Alternatively, the valve 121 could be a simple on-off valve with the pump and reservoir in series. While the flush pump 120 is in operation to flush the analyte conduit 5, the valve 4 is switched to divert mode (indicated by arrow 24b in FIG. 2), i.e. where the analyte fluid from source S is diverted to a drain conduit 6 or collection vessel 7.

The flush pump 120 preferably runs at a higher flow rate than the calibration fluid pumps 9, 12 and is useful to remove air bubbles or other obstructions to flow.

With reference to FIG. 12, a further feature may be added to the microfluidic flow controller, such as the microfluidic flow controller 1 of FIG. 1 or any of the variations thereof described herein. In this arrangement a further interconnect 126 in the analyte conduit 5 and a further valve 125 coupled to the analyte conduit by a reagent conduit 127 are used to enable delivery of a suitable reagent, such as a sensing reagent, to the analyte conduit 5, from a reagent reservoir 128 and reagent fluid source inlet 130 using a reagent pump 129. The reagent pump 129 may operate in the same manner as the calibration fluid pumps 9, 12, e.g. to charge the reagent pump 129 from reagent reservoir 128 when the reagent pump 129 is isolated from the analyte conduit 5, and to discharge the pump 129 to the analyte conduit 5 during an analysis mode, as shown by arrow 124 and arrow 24a. Alternatively, the reagent pump 129 may be a non-reciprocating pump (e.g. not a piston pump requiring a separate charge phase and discharge phase as discussed above) and may be in series with the reservoir 128 and valve 125 for single direction pumping towards the valves 125. In this case, the valve 125 could be a simple on-off valve with the reagent pump and reagent reservoir in series.

While the reagent pump 129 is in operation to deliver reagent to the analyte conduit 5, the valve 4 is switched to analysis mode, i.e. where the analyte fluid from source S is delivered to the analyte conduit 5, and the one or more calibration valves (e.g. second valve 8 and third valve 11) are in standby mode, i.e. not delivering calibration fluid to the analyte fluid conduit 5. In this way, the analyte fluid (e.g. dialysate) from the source S may be combined with a reagent suitable to initiate a reaction in the analyte fluid to render component parts of the analyte fluid more readily detectable by the analysis module 5. Similarly, during calibration mode when the valve 4 is switched to drain mode and the calibration fluid valves 8, 11 are switched to calibration mode, the reagent valve 125 may be switched to add reagent fluid to the calibration fluid(s), if necessary. The controller 20 (not shown in FIG. 12) may be operable to ensure that the combined flow volume reaching the analysis module 5 from the first valve 4 and the reagent valve 125, or from the calibration fluid valves (e.g. second and third valves 8, 11) and the reagent valve 125 is maintained within the required specification of flow rate or constant flow rate. In this respect, the reagent fluid may be considered as part of the analyte fluid flow stream and part of the calibration fluid flow stream.

If a reagent fluid is being used, this may limit the possibility of using a second downstream analysis module or multiple sensors within the analysis module unless they are compatible with the reagent and/or any by-products therefrom FIG. 13 illustrates how the functions of the flushing arrangement and the reagent delivery arrangement may be combined in the same microfluidic flow control apparatus.
Calibration When the analyte fluid has been switched away from the analyte conduit 5 (and away from the analysis module 16) to the drain conduit 6, a calibration process may be effected.

The controller 20 may be configured to control the valves 8, 11 and microfluidic pumps 9, 12 to perfuse a range of predetermined calibration fluid standards through the analysis module past the sensors in the analysis module. In a preferred configuration, the total flow rate of calibration fluids from the pumps 9, 12 during the calibration mode should be the same flow rate as the analyte fluid (e.g. microdialysate) in the analysis mode if the sensors are flow sensitive. In the configuration shown in FIGS. 1 and 2 the controller 20 may be configured to control of the ratio of output of the two (or more) pumps 9, 12 so as to allow any substrate concentration to be delivered to the analysis module 16 from 100% first calibration fluid/0% second calibration fluid to 0% first calibration fluid/100% second calibration fluid whilst maintaining constant flow rate. The calibration fluids may, for example, be any suitable solutions for calibration purposes, such as solutions at two different concentrations. If more than two calibration fluid reservoirs 14, 15/pumps 9, 12/valves 8, 11 are available, more complex ratios of calibration fluids, or selection combinations, may be chosen for the calibration mode. Calibration fluid or fluids from the valves 8, 11 may be delivered to the analysis module 16 together with reagent fluid from reagent valve 125 (FIG. 13), if required.

Once calibration has been achieved, the valves 8, 11 may all switch back to standby mode, the pumps 9, 12 can refill from the reservoirs 14, 15 containing the different calibration fluids (e.g. upper and lower concentration fluids) and the analyte (e.g. microdialysate), or analyte plus reagent, may be once again perfused through the analysis module 16. Where reagent fluid is being used, analysis and calibration modes would normally both require the reagent fluid to be delivered, and preferably with identical total flow rates through the analysis module.

The system exemplified in FIGS. 1 and 2 allows full automation of a calibration process and the flow controller 1 can periodically switch from analysis mode to calibration mode. The expression 'periodic' in this context is intended to encompass various control strategies including calibration at fixed time intervals or variable time intervals which may be predefined/user-programmed time intervals or calibration on-demand, e.g. when triggered by other conditions prevailing within the system or as triggered by analysis of the calibration data, discussed later. Calibration should ideally be as frequent as required to ensure the data recorded from the sensors in the analysis module is accurate and reliable.

During calibration mode, the controller 20 may be configured to execute a calibration routine in which the flow controller 1 is operative to vary the ratio of flow volumes/flow rates of calibration fluids from the first and second calibration source inlets to the analysis module. In one example as exemplified in FIG. 3, the first calibration fluid may comprise a solution at concentration A and the second calibration fluid may comprise a solution at concentration B. Varying the ratio of flow volumes during the calibration mode may comprise implementing a stepwise transition of calibration fluid flows 30 as a function of time to commence at, e.g. 100% B concentration during time period 31; a 75%/25% ratio of B/A during time period 32; a 50%/50% ratio of B/A during time period 33; a 25%/75% ratio of B/A during time period 34; and a 0%/100% ratio of B/A during time period 35. The duration of the time periods 31-35 may be selected to ensure that any measurements from the analysis module for each concentration level have sufficient time to stabilise. This period can be kept very short by ensuring that flow conduit dimensions are kept as small as possible.

With reference to FIG. 4, a microfluidic fluid analysis apparatus 48 includes an analysis module 16 which may comprise a number of sensors such as electrodes 40 positioned within an analyte flow channel/conduit 41. The electrodes 40 are configured for sensing different chemical/biochemical molecules/ions flowing through the analyte flow channel 41. Electrical current outputs 42 from the electrodes in the analysis module 16 can be converted to voltages and digitised with high precision by sampler and A/D converter 43.

Alternatively, electrical voltage outputs 42 from the electrodes (e.g. ion selective electrodes) may be sensed and digitised by the sampler and A/D converter 43. The digitised samples can then be passed to a calibration processor 44. Based on the known calibration fluid concentrations passing through the analyte flow channel 41 under the control of controller 20, the digitised outputs of the electrodes 40 may be used to define one or more calibration curves/profiles defining the analysis module sensitivity. These calibration profiles may be stored in memory 45. The expression 'calibration profile' is intended to encompass both (i) linear (straight line) relationships between the current or voltage and the analyte concentration and (ii) non-linear (e.g. curved) relationships between the current or voltage and the analyte concentration.

As the flow control apparatus can control autocalibration timing and the calibration fluid concentration values delivered to the analysis module, it can automatically determine the analysis module sensitivity response curve/profile at regular intervals. Curve fitting and parameterisation of the fit allows the electrode outputs 42 to be converted in real-time either to digital or analogue signals 46 that are directly proportional to the analyte concentrations with a fixed scale. This is of particular advantage to all downstream display and event detection software. Furthermore, the system keeps track of the analytical module sensor performance as sensitivity changes with time. In this way, the system can predict the best time interval between autocalibrations to minimise loss of real-time patient data (which may occur during calibration) and yet maintain the sensors as 'fit for purpose'. The system can also estimate the lifetime of the current sensors.

For example, as shown in FIG. 5, an initial calibration process performed by the controller 20 and calibration processor 44 may determine a first calibration characteristic/profile 50 relating electrode current and molecule/ion concentration. A subsequent second calibration process performed may determine a second calibration profile 51, and subsequent third and fourth calibration processes may determine third and fourth calibration profiles 52, 53 respectively. These calibration profiles may be stored by calibration processor 44 in memory 45. Comparison of calibration profiles 50-53 over time can enable the microfluidic fluid analysis apparatus to automatically determine an appropriate calibration interval. For example, depending upon the accuracy required by the user, the change in calibration profile from profile 50 to profile 51 may be used to identify the rate of change in sensor sensitivity as a function of time. Dependent upon the accuracy required, the calibration process may be automatically run more, or less, frequently dependent upon the rate of change of calibration profile 50-53 over time.

The system may further be operative to determine when the calibration profile 53 has reached a characteristic (e.g. a degree of slope, and/or a degree of non-linearity) which is indicative of inadequate sensor performance or of excessive sensor degradation. For example, the shallow slope of calibration profile 53 may be indicative of inadequate sensor performance (e.g. insensitivity). The calibration processor 44 may be configured to trigger an alarm or alert status which may indicate expiry of the analysis module, e.g. that the sensor or electrode or analysis module must be changed. By monitoring the rate of change of calibration profile 50-53 as a function of time, the calibration processor 44 may be configured to predict an optimum time to change the sensor or electrode or analysis module, and to thereby determine an expected expiry time thereof.

The combination of electrochemical biosensor devices within the analysis module 16 and the autocalibration control system 20, 44 provides a smart sensor functionality that appears to the end-user to be a perfect sensor with consistent and predefined characteristics.

An exemplary analysis module may be configured with specially configured sensors, for example electrodes, for the detection of pyruvate, glucose, lactate, potassium, sodium etc in the analyte flow. A typical calibration interval in this context may be, for example, of the order of every 2 to 3 hours.

Sensor/Electrode Positioning

FIG. 6 shows a perspective view of an analysis module 16 which is suitable for use with the apparatus of FIGS. 1 and 2. FIG. 7 shows the components of the analysis module 16 in exploded form. Housing 60 defines a microfluidic analyte flow conduit 41 (FIG. 4) extending longitudinally therethrough from an inlet 61 to an outlet 62. The housing 60 defines a pair of receptacles 63, 64 each extending into the housing body and configured to receive a respective sensor holder 65, 66. Each sensor holder 65, 66 is configured to receive and engage a respective needle sensor assembly 67, 68. Each needle sensor assembly 67, 68 may include a collar portion 69 and a needle shaft 70 through which pass sensor wires, terminating at sensors such as electrodes at the distal end 71. The sensors/electrodes are exposed at the distal end 71 in a manner described below. Although the analysis module 16 as shown in FIGS. 6 and 7 provides two sensor holders 65, 66, the module may generally include one or more sensor holders 65, each configured to receive and engage one or more needle sensor assemblies 67, 68. Two sensor holders may, for example, be deployed for two separate needle sensors, one for glucose and the other for lactate sensing.

Referring now to FIG. 8, as shown in the cross-sectional diagram of FIG. 8*a*, the flow conduit 41 extends longitudinally from the inlet 61 to the outlet 62, optionally via a bend 80 (the bend and upright section may be omitted to reduce conduit volume). At the inlet 61 and the outlet 62, the housing 60 may define receptacles 61*a*, 62*a* for receiving fluid line connectors (such as 73, 74 seen in FIG. 7) for easy coupling of the analysis module 16 respectively to an analyte fluid supply line and a drain. The housing 60 defines the lateral walls 81 of the flow conduit 41. The expression 'lateral' in this context may encompass top, bottom and side walls of the conduit 41, and includes a curved wall of a conduit of circular or non-rectangular cross-section. An aperture 82 is defined in the lateral wall 81 of flow conduit 41 (best seen in the magnified detail of FIG. 8*b* which is rotated 90 degrees anticlockwise from the image of FIG. 8*a*). The aperture 82 provides for fluid communication between the flow conduit 41 and the receptacle 63. The receptacle 63 also defines an engagement mechanism for capturing and retaining a sensor holder 65 when engaged therewith. In the example shown, the engagement mechanism is a bayonet fitting comprising a pair of channels 84 for receiving and guiding pegs of the sensor holder 65 to be described below. The channels 84 may include a helical section and a straight section as generally known in bayonet fittings. The straight section enables the longitudinal (depth) position of the holder 65 in the receptacle to be fixed. Alternative engagement mechanisms may readily be deployed in this context. In the top view of FIG. 8*c*, the receptacle 63, the open end of channels 84 and the aperture 82 as well as the inlet 61 may be readily seen. The receptacle 64 may generally be of the same design as the receptacle 63. The dimensions shown in FIG. 8 are given in millimetres and serve as a typical, non-limiting example.

Referring now to FIG. 9, the sensor holder 65 comprises a body 90 defining a cavity 91 serving as a needle sensor assembly mount for receiving a needle sensor assembly 67 or 68 (FIG. 7). At the distal end of the cavity 91 is an aperture 92 for allowing passage of the needle shaft 70 of the needle sensor assembly 67, 68. The sensor holder 65 further includes a soft compressible and resilient seal member 93 at the distal end of the holder 65. The seal member 93 has a sealing surface 94 which effects sealing engagement with the inside bottom surface of the receptacle 63 or 64 when the sensor holder 65 is engaged with the receptacle 63 or 64. The seal member 93 preferably has a truncated cone shape as shown which can assist in fluidic sealing and reduce the chance of incorrect positioning of the sensor holder 65 and thus the needle sensor assembly 67/needle shaft 70 when installing the sensor holder 65 in the receptacle 63 or 64. The seal member 93 also provides sealing engagement with the shaft 70 of the needle passing therethrough, preferably by friction fit while still allowing adjustment of the longitudinal position of the needle passing through the seal member 93. Pegs 95 form part of the bayonet fitting and are configured to travel within and be retained by the channels 84. A pair of screw holes 97 are used to retain grub screws (not shown) which can bear against the collar portion 69 of a needle sensor assembly 67 or 68 to set the position of the needle sensor assembly within the sensor holder 65. A slot opening 98 can be provided to provide access for a wire 101 coupled to a sensor/electrode defined by the outer wall of the needle shaft 70 itself (as seen in FIG. 6). Other sensor/electrode wires 102 can emerge from the proximal end of the needle sensor assembly, also as seen in FIG. 6. The dimensions shown in FIG. 9 are given in millimetres and serve as a typical, non-limiting example.

As mentioned above, any suitable engagement mechanism between the sensor holder and the flow conduit wall or walls may be deployed. For example, the flow conduit 41 housing may include a vertical channel/recess (relative to a horizontal flow conduit) for guidance of a distal end of the holder relative to an aperture in the wall of the flow conduit, and a horizontal pressure plate on the distal end of the holder may be biased against a sealing surface of the wall of the flow conduit housing by way of a suitable biasing and latching mechanism.

A major challenge is to incorporate and secure the sensing surfaces, or sensor elements/electrodes in the correct position inside the microfluidic flow conduit 41 while at the same time preventing any leaks. Precise positioning of the distal end 71 of the needle where the sensor elements are exposed within the flow conduit 41 is important to ensure that the exposed sensors are positioned within a precise part of the cross-sectional flow velocity profile of the fluid flowing within the conduit. With reference to FIG. 10, a typical flow velocity profile across a lateral cross-sectional dimension of the fluid conduit is indicated at 110, showing a maximum velocity in the central portion 111 of the flow conduit 41 and reduced velocity towards the walls 81 of the flow conduit. The expression "lateral cross-sectional dimension" includes top to bottom as shown in FIG. 10, or in the dimension perpendicular to the plane of the diagram in FIG. 10.

The exposed parts of the sensor elements, e.g. electrodes 112 may be set within a central portion of the needle shaft 70 which may be cut at a bevel as shown such that the electrodes 112 are exposed to the flow at the distal end 71 of the needle shaft. Preferably, the walls 81 of the fluid conduit 41 are smooth without recesses or other features disturbing fluid flow or providing stagnant regions which could affect the speed of response and sensitivity to changes in the composition of the fluid flow reaching the electrodes 112. This is particularly important where the needle shaft 70 emerges from the aperture 82. For example, a 50 micron deep recess in the walls 81 of the fluid conduit 41 where the electrodes 112 emerge, causing the electrodes to be displaced out of the central portion 111 of the flow velocity profile 110 may add 60 seconds to the response time of the electrodes to changes in analyte concentration in the analyte flow. Further, if the electrodes do not fully emerge from the aperture 82 into the flow stream, very poor performance of the analysis module may result.

More generally, the distal end 71 of the needle shaft 70 can comprise any particular profile required in order to position the electrodes 112 or sensor elements at any desired lateral position of the flow conduit 41, e.g. at any desired position in the cross-sectional flow velocity profile 110, including flush with a wall 81 of the fluid conduit 41.

Particularly in the case of a bevelled profile at the distal end 71 of the needle shaft 70, the rotational position (orientation) of the needle shaft about its longitudinal axis may have a profound effect on the sensitivity of the sensor elements such as electrodes 112 to the analyte flow in fluid conduit 41. It may be advantageous to ensure that the rotational position of the sensor elements 112 is guided, fixed or otherwise controlled by the engagement of needle sensor assembly 67, 68 within the respective sensor holder 65, 66 and by the engagement of the sensor holder 65, 66 in the receptacles 63, 64. This may readily be achieved by any suitable mechanism that determines a rotational position of the needle about its axis relative to the flow conduit 41. In one example a guide means such as a longitudinal channel or other profiled element may be provided in the sensor holder 65 which is configured to engage with a corresponding lug or other complementary profiled element in the needle sensor assembly 67, 68, such as on the collar portion 69. The co-operating profiled elements could comprise a non-circular cross-section of the cavity 91 in body 90 and a corresponding non-circular cross-section of the collar portion 69 such that the collar portion 69 can only enter the cavity 91 in one or a restricted range of orientations about the longitudinal axis. Alternatively, visual markings could be provided on the needle sensor assembly to indicate a desired rotational position. The rotational position of the sensor holder 65 relative to the receptacles 63 or 64 may, of course, be determined by the bayonet mechanism. The rotational position may be particularly important where the needle sensor tip is bevelled relative to the needle longitudinal axis, to ensure that the sensor elements are not shielded from the fluid flow by the shaft of the needle, for example.

In use, the needle sensor assembly 67 may be introduced into the sensor holder 65 and fixed in position using the grub screws in screw holes 97, such that the distal end 71 of the needle shaft 70 extends beyond the sealing surface 94. The holder 65 can then be inserted into the respective receptacle 63 or 64 and engaged therein by the bayonet mechanism. Precise adjustments to the longitudinal position of the needle shaft 70 within the holder 65 and thus to the distance the needle projects beyond the sealing surface can be made before, or after the holder is inserted into the receptacle. Hence, the distance that the needle shaft extends into the flow conduit 41 can be very precisely adjusted using the grub screws and by visual microscopic inspection. When the holder is inserted, needle position can be inspected down the conduit from the outlet 62 end. With flow conduit dimensions of a few hundred microns, precise longitudinal positioning of the needle distal end in the flow velocity profile requires considerable accuracy.

The sensor holder may be fabricated using a 3D printer capable of printing both hard and soft plastics simultaneously on the same component. This enables the sealing member 93 as well as the body 90 of the holder to be printed.

Adjustment of the positioning of the distal end 71 of the needle sensor assembly 67, 68 can be assisted by configuring the needle such that the electrodes 112 are somewhat proximal of the extreme tip 115 of the needle as seen in cross-section in FIG. 10. In particular, the extreme tip 115 of the needle extends distally of the electrode or electrodes 112 by a distance d which serves to position the electrode or electrodes 112 within the central portion 111 of the flow conduit 41. Thus, in a general aspect, the needle extreme tip extends distally of the electrode or electrodes by a distance equal to a portion of the diameter of the flow conduit 41 so as to place the electrode or electrodes within the central half portion 111 of the flow conduit 41. In this way, the longitudinal position of the needle 70 can be adjusted until the extreme tip thereof abuts the lower wall 81 of the flow conduit, which assures that the electrodes 112 will then be optimally positioned within an optimum flow zone of the flow conduit.

Although the needle sensor assembly in the example of FIG. 10 is shown as comprising electrodes 112 as the sensor elements, the sensor elements may comprise other types of sensor or biosensor. For example, optical sensors, possibly incorporating fibre optic cables passing through a needle sensor assembly similar to that described above, may be envisaged for detecting concentrations of certain analytes, e.g. pyruvate.

Alternative configurations of apparatus for sensor/electrode positioning can be envisaged. An alternative design for the analysis module 16 is illustrated in FIGS. 10A, 10B and 10C.

In the arrangement of FIG. 10A, the shaft 170 of a sensor assembly 167 is captured by a collar 169 with wings 150 which form a part of a bayonet fitting of a sensor holder 165. One or more grub screws 151 extend laterally through the collar 169 to fix the shaft 170 at a desired longitudinal position within the collar 169. A sealing medium 152 may form a tight seal against the shaft 170, while still allowing longitudinal sliding adjustment of the shaft 170 position within the collar 169. The sealing medium 152 may comprise a compressible, resilient material and may form part of the collar 169 itself and/or part of the sensor shaft 170 itself, or comprise an additional layer in between.

With reference to FIG. 10B, a block 166 defines a recess 154 into which the collar 169 (shown in dashed outline) is received. The recess 154 is configured to engage with a complementary part 153 of the bayonet fitting, e.g. including a guide channel which directs axial and rotational motion of the collar wings 150 to firmly engage with the block 166 against a recess base 155. The recess base 155 may include a gasket (not shown) for a fluid tight seal. The bayonet fitting is preferably configured for locking engagement of the sensor holder 165 with the block 166 by way of a quarter turn, as indicated in the inset top view diagrams, with the bayonet wings 150 perpendicular to the flow channel/conduit 41. The base 168 of the block 166 may include a gasket 171 for fluid tight sealing against a structure below. The gasket 171 could form an integral part of the block 166 or a separate layer there on. When the sensor holder 165 is coupled to the block 166, the shaft 170 of the sensor extends downwards below the base 168 and/or gasket 171 of the block 166. The block 166 can be configured to hold one, two or more sensors holders 165 as required, or may even be configured to hold no sensor holders 165 if it is required to serve as a blanking plate.

With reference to FIG. 10C, a housing 160 defines the analyte flow conduit 41 and an aperture 182 in a lateral (top) wall of the conduit 41. The block 166 can be positioned within the aperture 182 and retained in place by any suitable compression mechanism. In the example shown, the compression mechanism comprises a pair of rotatable discs 185 which can be locked into position over the block 166 using screws 186, and apply downward pressure against the base 184 of the aperture 182. The block 166 (and/or the aperture walls) may be provided with end gaskets 187 at least at the edges shown in the top view inset diagrams so as to provide additional fluid sealing at the edges of the aperture 182 immediately above the channel 41 to prevent fluid escape from the channel.

Thus, in a general aspect, the arrangement of FIGS. 10A to 10C provides a sensor holder comprising sensor holder 165 and block 166 which is configured for removable engagement with an engagement mechanism comprising discs 185 and screws 186. Like in arrangements described above, the sensor holder 165, 166 enables fine adjustment of the extent to which a needle sensor shaft extends through the aperture 182 and into the flow conduit 41.

In this arrangement, the housing 160 of the channel 41 may be more readily manufactured by various means including additive manufacturing processes or by soft lithography or injection moulding which may be better able to give a smooth, void free channel at the scale required for microdialysis flow rates. Very precise control of the sensor shaft 170 depth within the flow conduit 41 is possible by setting/adjusting the position of the sensor shaft 170 within the collar 169.

Alternatively, the sensor shaft 170 could be fixed to the collar 169 at the time of manufacture (not necessarily requiring grub screws 151). In this instance, fine adjustment to the sensor shaft 170 position may be made by a suitable vertical adjustment mechanism in the mechanism coupling the collar 169 to the block 166, e.g. a screw thread mechanism.

If a very precise manufacturing process can be used to define the thickness of the block 166 (e.g. from the recess base 155 to the block base 168), and the channel depth relative to the base 184 of the aperture, it may be possible to lock the sensor shaft 170 into longitudinal position within collar 169 during manufacture with the correct length of sensor shaft 170 extending therefrom. This could be done using a depth guide using a template channel and adjusting position using the extension of the shaft into the template channel to set the depth. In this way many sensors could be set to the correct position at one time as a batch process.

The systems and apparatus described above exemplify systems which handle continuous, single phase microfluidic flows. The systems can be adapted to implement multiphase flows, e.g. temporally-separated two phase flows in which discrete portions of analyte fluid are regularly separated by an alternative phase of non-analyte fluid such as a gas/air or an immiscible other fluid such as an oil.

Within damaged tissue the levels of key analytes such as glucose, lactate and pyruvate enables interpretation of tissue health facilitating clinical judgment during critical periods of treatment. Sensors such as those described above that can detect small concentration changes in these analytes need to be highly sensitive, fast, stable and selective. Ratios between lactate and pyruvate, or lactate and glucose are important metrics as they are less sensitive to artefacts in the data, such as that caused by changes in probe recovery. The very small volumes of fluid flow, and the intermittent calibration routines without disturbance to fluid flows, provided by the apparatus described above, provides very substantial improvements in on line analyte fluid monitoring with high data rates, fast response, and continuing accuracy.

Delivery of such performance is highly challenging. The approach described above is for a smart sensor, which behaves as an idealised sensor because it is within a controlled environment that manages its own limitations. Periodic and automatic calibration of the sensors enables reliable interpretation of the sensor output (current to concentration). As clinical monitoring often occurs for multiple consecutive days, this system is ideally automated.

To avoid artefacts in the data, the flow rate through a probe P should preferably remain constant. The sensors/analysis modules may also produce artefacts if the flow rate across them changes due to changes in delivery of molecules to the sensor surface rather than changes in concentration. The computer-controlled environment described above can avoid both artefacts.

The apparatus and methods described above operate within the microfluidic domain as defined above. However, preferred flow rates of analyte fluid flow and calibration fluid flow envisaged in the apparatus and methods described may be between 0.3 and 2 microlitres per minute or even up to 5 microlitres per minute.

The outputs 46 from the system can be readily ported to various portable devices including Android and iOS display devices as well as other conventional computerised hardware and software. This allows remote control and monitoring of the system from any suitable device.

Other embodiments are intentionally within the scope of the accompanying claims.

The present invention also provides sensors that are considered to be suitable for using with a sample in flow, and suited for use in online continuous monitoring systems; considered to have good sensitivity; good linear working range and a stabilised transduction stage (i.e. typically are not significantly disturbed by bubbles or multi-phase flow). These features are desirable but not essential. For example, a linear working range is useful but not essential. Sensors with a non-linear curve fit are also useful. For example, it is considered that a glucose sensor as described below, for example, may be non linear at low concentrations as well as at higher concentrations.

Therefore, in one aspect, the invention provides a sensor, comprising at least one working electrode, at least one auxiliary electrode, and at least one reference electrode, wherein the sensor comprises a hydrogel layer that extends over the said at least one working electrode, auxiliary electrode and reference electrode.

By a sensor we include the meaning of an electrochemical sensor, an amperometric sensor, a biosensor, and an amperometric biosensor. An electrochemical sensor is one that functions by the production of a current when a potential is applied between two electrodes. The current generated may be proportional to the concentration of chemical species in solution, or for example in a hydrogel. An amperometric sensor is a sensor that measures the current at a constant potential. There are other ways in which sensors can be used, for example there are several dynamic voltametric technologies where the potential is pulsed or scanned. These include Chronamperometry, cyclic voltammetry and differential pulse voltammetry. A biosensor is defined by the International Union of Pure and Applied Chemistry as a sensor wherein the bio recognition agent is integrated with the detection mechanism (DANIEL R. THEÂVENOT, KLARA TOTH, RICHARD A. DURST AND GEORGE S. WILSON 1999 Pure Appl. Chem., Vol. 71, No. 12, pp. 2333±2348).

Sensors of the present invention include biosensors, particularly for the detection of glucose, lactate or pyruvate wherein the sensor comprises a hydrogel with an enzyme. The invention also comprises sensors that are not strictly biosensors, for example a sensor for the detection of pyruvate used with a sensing liquid which contains an enzyme. The term sensor is intended to cover all of these various sensors.

Sensors are reviewed in Grieshaber et al 2008 Sensors 8: 1400-1458, for example.

The sensor may be for the detection of metabolites of molecules in a sample taken from a subject, for example from a human or animal subject. The sensor may be used in, for example, the diagnosis of a medical condition, monitoring the progression of evolving pathology (e.g. traumatic brain injury) or surgical interventions, or for the evaluation of the appropriate treatment regimens. The sensor may also be used during exercise, for example to aid an athlete in his/her training.

By a sample taken from a subject we include the meaning of extracellular fluid extracted from the subject via microdialysis.

Alternatively the sensor and sensor system herein described may not be used in conjunction with a sample from a human or animal subject, but may be used in conjunction with any other sample. For example, the sample may be an environmental sample, and the sensor may be used to detect and analyse the levels of a particular molecule, in particular may be used wherein the molecule and situation is such that a continuous measurement is desired.

In a preferred embodiment the sensor is for use with a sample obtained from an animal or human subject. The sensor may be termed a biosensor. A biosensor is a sensor that comprises a biological molecule to detect an agent, metabolite or molecule. The biological molecule can be any biological molecule, for example can be a protein, for example an antibody or an enzyme, or could be a nucleic acid, for example DNA or mRNA, By at least one working electrode we mean that the sensor may comprise one or more working electrodes, for example may comprise 2 working electrodes, or may comprise 3 working electrodes or more. The working electrodes may be consecutively arrayed.

An electrode is considered to be an anode when electrons move from the solution into the electrode. An electrode is considered to be a cathode when the reverse is true and electrons move from the electrode into the solution. The working electrode may be an anode or may be a cathode, depending upon the reaction that is taking place and what is being measured.

Typically it is hydrogen peroxide that is being detected (for example with the working electrode held at +0.7V) and the electrons move from the hydrogen peroxide into the electrode, thus in this situation the electrode is considered to be anodic. However in some embodiments wherein a mediator, such as ferrocene monocarboxylic acid, is used, and the working electrode is held at 0V, the working electrode is operated as a cathode because electrons move from the electrode to the ferrocinium ions.

The working electrode may therefore be a source of electrons (to allow sensing by reduction of species in solution), or may be a sink for electrons (to allow sensing by oxidation of the species in solution).

The working electrode may be formed from or comprise an inert material, for example the working electrode may be carbon (such as glassy carbon, carbon fibres, carbon nanotubes, Boron doped diamond, graphene) or gold. In a preferred embodiment the working electrode is a solid metal with good conductance. In a particularly preferred example the working electrode is platinum as it is considered to have an optimal surface for the oxidation of hydrogen peroxide. The working electrode may comprise a core, for example carbon, that is coated in a metal of choice, for example may be coated with platinum.

The choice of material for the working electrode is dependent upon the reaction that is being conducted. The skilled person would readily be able to determine the most suitable material for the particular reaction.

In one embodiment the at least one auxiliary electrode and the at least one reference electrode are separate entities. In an alternative embodiment, the at least one auxiliary electrode and the at least one reference electrode may be combined, i.e. one physical electrode that performs the functions of both an auxiliary electrode and a reference electrode. For example a silver/silver chloride wire may act as a combined reference and auxiliary electrode. This arrangement is not as preferred as it is considered that such an arrangement may be less stable than when the three electrodes are distinct entities. However, this arrangement may be useable for single measurements over limited time periods and small currents. Typically the three electrodes are distinct.

The working electrode may make direct contact with the analyte, or may make contact with a product of a catalysed reaction involving the analyte. As an example, the working electrode may make direct contact with dopamine (a neurotransmitter). Dopamine can be directly oxidised at the electrode surface to give 2 electrons, which are measured as a current. Other examples include ascorbic acid (which is also considered to be an interefent and is discussed below).

Alternatively, if the working electrode is to be used to assess the concentration of an analyte that is not electroactive under the relevant conditions, for example, the concentration of the analyte can be determined by conversion of the analyte to a product that is electroactive and can generate a current that depends on (for example is proportional to) the initial concentration of the analyte in the fluid (which may be in a hydrogel) contacting the working electrode. It is considered that everything can be oxidised or reduced (for example even inert gases). The issue to consider is can the potential required in the solvent in which you are working (for example water) be achieved without oxidising or reducing the solvent. This gives a concept of a potential window for a solvent. An additional issue is whether the oxidation/reduction occurs at an appreciable rate, which is dependent on the electrode material. For example, ascorbic acid oxidises at −0.19V at some carbon materials and at +0.45 V at platinum.

The reference electrode can be made from, for example silver wire that has been chloridised to create a silver/silver chloride reference electrode. This can be achieved, for example, by applying a mildly oxidising potential (e.g. done electrochemically where the reference electrode is acting as the working electrode in a new cell). In one embodiment, the wire may be dipped in a reference solution (for example from BASi) for 5 seconds, followed by dipping in HCl for 30 seconds. HCl can be used to clean the working electrode without stripping the newly made reference electrode, in situations wherein the electrodes are together, for example when the electrodes are arranged as a needle electrode/sensor. It is considered that cleaning with for example HCl is only required when it is not physically possible to apply the reference solution only onto the silver wire.

The electrodes may be arranged in any order or any arrangement suitable for the detection of the particular analyte. In a preferred arrangement, the working electrode and the reference electrode are located within an outer sheath that functions as the auxiliary electrode. In one embodiment the auxiliary electrode comprises or consists of a metal shaft, for example a hollow metal shaft, for example a hollow needle. In one embodiment the auxiliary electrode is a stainless steel shaft. In a further embodiment the auxiliary electrode is a stainless steel needle. This type of arrangement, wherein the sensor comprising the electrodes is in the shape of a needle will be referred to as a needle electrode or needle sensor, whether or not the auxiliary electrode is actually a needle. It is considered advantageous however to have the arrangement wherein the working and reference electrode are within the auxiliary electrode as it maintains a three electrode system with a μm sized space. This is particularly suited for analysis in analyte flow stream of μm sized dimensions. It is preferred if all of the electrodes are integrated in this or a similar way into a single unit.

Thus, the auxiliary electrode may be the outer metal shaft of a needle sensor. The auxiliary electrode may typically be formed from stainless steel, gold or platinum.

One important factor to consider when contemplating the auxiliary electrode is its size. It is considered advantageous if the surface area of the auxiliary electrode is much larger than that of the working electrode, as it is considered that the operation of the auxiliary electrode will then not limit the reactions on the working electrode.

When the auxiliary electrode is stainless steel, it is considered that only small oxidation currents may be passed through the electrode (ie the auxiliary electrode passes small reduction currents) which is considered to not corrode the stainless steel material.

The sensor also comprises a hydrogel layer. Hydrogels are considered to have a flexible polymeric framework that is substantially hydrophilic, promoting hydrogen bonding to, for example, water. Thus the hydrogel is considered to incorporate substantial quantities of water as part of its composition. This water rich environment in turn stabilises many enzymes and allows easy passability of water soluble substrates. The network nature of the hydrogel is sufficient to entrap large protein molecules such as albumin and enzymes. The hydrogel may be considered to be firm yet elastic (rather than the brittle nature of solid gels such as sol-gels) which is tolerant to handling and for example entry into narrow entry holes or channels.

The hydrogel may comprise albumin or may comprise PEG-DE. One example of a hydrogel is a hydrogel comprising 30 mg/ml albumin, 60 mg/ml PEG-DE, 2% glycerol in 0.01M PBS but other forms of hydrogel may be used.

In one embodiment the sensor has a linear working range over the expected concentration range. In another embodiment the sensor has a non-linear working range. For example, it is considered that glucose sensors tend to be non-linear at low concentrations as well as at higher concentrations. In a further embodiment, the sensor has a non-linear and a linear working range, depending upon the concentration of metabolite or molecule under detection.

The sensor typically is for use outside the body. In such cases the choice of the hydrogel is not constrained by issues such as mechanical durability, penetration and removal from tissue. Therefore any hydrogel suitable for use in the sensor is encompassed in the present invention. Preferably the hydrogel is such that when, for instance, the hydrogel comprises an enzyme or other bioactive molecule or substrate, the hydrogel is such that it does not interfere with any enzymatic or other reaction.

In one embodiment the hydrogel covers only the working electrode or working electrodes. In a preferred embodiment the hydrogel covers at least part of all electrodes within the sensor. Thus, typically there would be hydrogel between each of the electrodes within the sensor and between the fluid being analysed and each of the electrodes.

In a preferred embodiment, the hydrogel covers only the distal end of the sensor, of all three electrodes, i.e. the end which contacts the sample. The hydrogel may also cover the glue in between the electrodes that holds them together. For mechanical reasons, for example, the hydrogel may stay adhered to the sensor better if the hydrogel does not extend up the outer surface of a needle electrode/sensor, as discussed further in the Examples. It is considered that when the hydrogel covers all three electrodes, even if only at the very distal tip, i.e. when the electrodes are arranged in a needle fashion, the hydrogel protects against electrical disconnection. To protect against electrical disconnection from, for example, bubbles, it is considered essential that the hydrogel covers at least part of the auxiliary electrode, to complete the circuit.

The hydrogel layer is considered to aid in reducing electrical disconnection of one or more electrodes due to multi-phase flow, for example air bubbles or non-aqueous carrier liquid within the fluid flow and therefore is considered to have beneficial properties.

When the working electrode and the reference electrode are located within an outer needle-like sheath, which may form an auxiliary electrode, the size of the overall sensor is considered to be very small, particularly in diameter. For example the overall diameter of the sensor, for example the diameter of the auxiliary electrode sheath is for example between 311 μm (a 30 G needle) and 514 μm (a 25 G needle), for example may be 412 μm (a 27 G needle). The electrode sheath may be bigger than this, or may be smaller, for example 220 μm. The size of the sensor chosen may depend on the size of channels and tubing used. For example, the smaller the diameter of the tubing, the smaller the channel that can be used, and the smaller the electrodes. Using a smaller channel may improve time resolution of the measurements conducted, as discussed further below.

The diameter of the working electrode is preferably 50 μm or smaller or larger, for example may be between 10 μm and 75 μm, for example may be 10 μm or 25 μm. It is considered that the signal to noise is better for smaller electrodes, providing that layer 1 sticks to the electrode.

The diameter of the reference electrode is preferably 50 μm or smaller or larger, for example may be between 25 μm and 75 μm. It is considered that if the electrode is too small it will be susceptible to corrosion.

When the working electrode and the reference electrode are located within an outer sheath, for example an outer auxiliary electrode, the length may also considered to be small. The auxiliary electrode may be an annular ring, for example when positioned flush with the channel wall, or some of the shaft length may be exposed within the channel, for example when the sensor is for use in a microfluidic device or system.

The length of the electrodes when used with a microfluidic chip is typically defined by the channels and the subsequent placement of the needle within that channel. From an electrochemical point of view the size of the auxiliary electrode is determined by the diameter of the needle and the needle wall thickness (ie the ring at the tip).

In one embodiment the hydrogel comprises an enzyme, for example an oxidase. The enzyme within the hydrogel should be such that it is capable of converting the metabolite or molecule under investigation into a molecule capable of forming a current and therefore detection via the electrode. For example, oxidase enzymes utilise available oxygen to catalyse a reaction leading to the formation of hydrogen peroxide. Hydrogen peroxide is readily detected by the sensor described herein and therefore any enzyme capable of producing hydrogen peroxide may be included in the hydrogel.

In one embodiment the sensor is for the detection of lactate, glucose or pyruvate. Therefore the hydrogel may comprise lactate oxidase, glucose oxidase or pyruvate oxidase. In a more preferred embodiment the hydrogel comprises lactate oxidase or glucose oxidase. The sensor may alternatively be for the detection of choline or ATP, and therefore in alternative embodiments the hydrogel may comprise choline oxidase or hexokinase. Other oxidases or suitable enzymes, such as horseradish peroxidase, may also be included in the hydrogel. In one embodiment the hydrogel comprises horseradish peroxidase.

Cofactors for the enzymes may also be included in the hydrogel. For example, where the enzyme is pyruvate oxidase, the hydrogel may also comprise $MgCl_2$ and TPP. Cofactors such as these are considered to be small and likely to diffuse out of the hydrogel. However, it is considered useful if cofactors that stabilise the enzyme are present in the hydrogel when it is being formed so that the space enclosing the enzyme is suitable for a properly constituted functional enzyme.

Other agents that aid in the detection of the metabolite or molecule under investigation may also be included in the gel. For example:
1) a mediator molecule—however if the molecule is small it is considered that the molecule would also have to be in the analysis solution and be able to get through layer 1.
2) An enzymatic filter such as:
   (a) ascorbate oxidase (which is not a normal oxidase and produces water instead of hydrogen peroxide)—filters out ascorbate interferent chemically;
   (b) catalase—converts hydrogen peroxide back into oxygen. This would typically only be at the outside edge of the hydrogel but would prevent leakage of hydrogen peroxide into the analysis stream (which could interfere with other sensors present) and maintain oxygen concentrations. However, if the catalase was near the electrode surface it would compete very well with the electrode.

It will be apparent to the skilled person that the amount of enzyme in the hydrogel should be chosen to be sufficient to enable detection of the analyte molecule over the expected concentration range. Typically a quantity of enzyme would be chosen which would mean that the capacity of the enzyme to convert the analyte molecule into the detected entity (for example hydrogen peroxide) is not the limiting factor in the amount of hydrogen peroxide that is produced. For example, should the enzyme concentration be too low, the enzyme may be saturated by the amount of analyte molecule present, so higher quantities of analyte may not be distinguishable and importantly the conversion efficiency of the substrate into hydrogen peroxide would be low. If this is the case, fluctuations in the concentration above the concentration of detection of the sensor would be missed. Therefore it is preferred if the concentration of the enzyme in the hydrogel at the electrode is chosen to be above an amount that is considered to lead to a "plateau" of response.

Generally, the apparent Km of the system is determined. The amount of the enzyme varies the Vmax. However if sufficient enzyme is available then conversion rates are high and the sensor can keep going above the Km curvature because although the enzyme binding might be close to saturation in a homogeneous situation, the enzyme is in a reaction layer and while the outside layers of enzymes might be saturated the inner ones still have binding capacity.

The skilled person would be well aware of techniques to determine the concentration of enzyme required, for example by simple calibration using samples of known concentration that are relevant to physiological concentrations. In one embodiment the amount of enzyme on the electrode is that which results from: dipping the tip of the electrode, or all three electrodes, or needle electrode as defined above in a solution comprising 60 mg/ml lactate oxidase, (at 20-60 U/mg), 30 mg/ml albumin, 60 mg/ml PEG-DE, 2% glycerol in 0.01M PBS for one minute; and drying the electrode(s) upside down at 55° C. for 2 hours.

Typically lactate oxidase has 20-60 U/mg, glucose oxidase has 250 U/mg and pyruvate oxidase has 25 U/mg, wherein typically 1 Unit is the amount of enzyme taken to convert 1 µmol of substrate per minute under specified conditions of substrate, pH, cofactor and temperature.

Typically the amount of enzyme that is in the solution into which the electrode is dipped is between, for example, 40 mg/ml to 400 mg/ml, for example between 60 mg/ml to 350 mg/ml, for example between 80 mg/ml to 300 mg/ml, for example between 100 mg/ml and 250 mg/ml, for example between 120 mg/ml and 200 mg/ml, for example between 140 mg/ml and 180 mg/ml, for example between 150 mg/ml and 160 mg/ml.

Typically the amount of enzyme that is in the solution into which the electrode is dipped is between, for example 800U/ml and 100,000 U/ml, for example between 1,000 U/ml and 75,000 U/ml, for example between 2,000 U/ml and 50,000 U/ml, for example between 4,000 U/ml and 25,000 U/ml, for example between 5,000 U/ml and 20,000 U/ml, for example between 7,000 U/ml and 15,000 U/ml, for example between 10,000 U/ml and 12,000 U/ml.

The skilled person would also be aware that enzyme can be lost from the hydrogel, or inactivated, and would be capable of taking this into account in the required calculations.

In one embodiment the hydrogel may be chosen for compatibility with the chosen enzyme.

In an alternate embodiment, the hydrogel does not comprise an enzyme. This is considered to be useful when assessing a metabolite or molecule that may not be optimally assayed by a method involving enzymatic conversion in the hydrogel layer. For example it is considered that the detection of pyruvate when pyruvate oxidase is located in the hydrogel may not be the most sensitive method and it may be preferred that the pyruvate oxidase be added instead in solution to the fluid to be analysed, for example dialysate, allowed to react, and then the formation of hydrogen peroxide analysed via the sensors. Such a method and reagent for use in such a method is described in more detail below. Therefore the sensor may comprise a hydrogel that does not contain an enzyme.

Furthermore, in some embodiments, for example wherein the sensor is for measuring the amount of pyruvate, the sensor may not comprise a hydrogel at all. Therefore in a particular embodiment, the invention provides a sensor, comprising at least one working electrode, at least one auxiliary electrode, and at least one reference electrode, wherein the sensor does not comprise a hydrogel layer that extends over the said at least one working electrode, auxiliary electrode and reference electrode. Other preferences for the sensor typically are as indicated above. This sensor is considered to be useful in the detection of pyruvate, for example in conjunction with a sensing reagent of the invention, described in later aspects. However, hydrogels have beneficial properties in addition to their use to immobilise enzymes, as described above, and therefore even for the measurement of pyruvate, the sensor may comprise a hydrogel.

When discussing a first, second and third layer, in below embodiments and aspects, it will be appreciated that the second layer is the hydrogel layer, and therefore where the second layer is missing the third layer will therefore be the second layer, but will be described herein as the third layer, to avoid confusion. Therefore an electrode may have a first and a third layer (i.e. no hydrogel layer), but only comprise two layers In a preferred embodiment of the sensor, prior to application of the hydrogel layer (when the sensor comprises a hydrogel layer, and independent of the inclusion of an enzyme in the hydrogel layer), the at least one working electrode is coated in a first layer. In a preferred embodiment, only the distal tip of the working electrode is coated in a first layer.

The first layer is considered to protect the electrode from damage and from fouling. For example, the first layer protects against poisoning of the working electrode function, optionally by poisoning of the electrochemical transduction reaction. The first layer is such that it blocks the access of any enzymes in the hydrogel layer (the second layer) to the electrode. Enzymes tend to denature on the electrode which is considered undesirable.

It is possible to include enzymes within this first layer in one embodiment, but it is preferred that the enzyme is located in a second hydrogel layer, as it is possible to incorporate more enzyme into this layer, making the sensor more stable, and the barrier to interference (the first layer) is more coherent due to no interruption of its form from the enzyme molecules.

The protection of the electrode from enzymes is particularly important when the enzymes are in solution. For example as stated above it is considered preferable to detect pyruvate in solution, adding the enzyme in solution to the dialysate. In this case (and in the case where pyruvate oxidase is located in the hydrogel) the first layer is therefore particularly important because pyruvate levels are considered to be very low and as such the relative magnitude of the interfering levels can be high. Layer 1 also stops the enzyme adhering on the electrode surface.

The first layer is also considered to block the access of smaller interferent molecules that could be oxidised by the electrode at the same potential to give a current which would interfere with the accuracy of the detection of the desired analyte, for example metabolite. Examples of such interferent molecules include ascorbic acid which is present in tissue, and (at much lower levels) some neurotransmitters. It is considered that these molecules are blocked from accessing the electrode via size exclusion, and possibly charge. Hydrogen peroxide is both very small and neutral and is therefore capable of passing through the first layer to the electrode. Therefore in one embodiment the first layer can be any layer that allows hydrogen peroxide to pass through, but that blocks substantially all of enzymes and interferent molecules from passing through. The skilled person would be well aware of chemicals to produce a layer with such properties. Examples of useful agents for use in the first layer are m-phenylenediamine, polyphenol, and O-phenylenediamine.

It is considered preferable if the first layer is thin, for example 15-20 nm, for example just larger than an enzyme molecule.

The first layer may be added to the working electrode by electropolymerisation. For example, the working electrode may be dipped into a solution of 100 mM m-phenylenediamine (PPD) in 0.01M PBS, and held at 0V for 20 seconds, 0.7V for 20 minutes, 0V for at least 2 minutes. The initial 0V is considered to aid in reproducibility, the 0.7V initiates polymerisation of the PPD, and the final 0V allows the film production to settle into a more stable film. Alternative agents include poly-phenol.

Where PBS is the buffer, it is important to consider both the phosphate acting as the buffer, and the physiological saline, which in 0.01M PBS is approximately 147 mM NaCl and 2.7 mM KCl. A fixed Cl concentration is generally required for the integrated reference electrode, which normally comes from the dialysate.

The layer is considered to have to be non-conducting and compact, to give selectivity by virtue of size or charge. Agents suitable for use in such a first layer will be apparent to the skilled person.

In addition to the first layer and the second hydrogel layer (when present), the working electrode is also coated with a third layer. The third layer is considered to extend the dynamic range and increases the sensitivity of the sensor. Surprisingly, despite the third layer increasing the apparent Imax for the sensor, it results in an increase in sensitivity. Generally a layer with these properties would be expected to decrease the sensitivity. Without wishing to be bound by any particular theory, it is considered that the third layer prevents enzyme from being lost to the analysis stream, and that it also may make layer 2 thinner (ie the effect of the Tetrahydrofuran (THF) solvent on the layer) without loss of enzyme thereby improving the delivery of peroxide to the electrode surface.

In one embodiment the third layer is polyurethane. Other suitable agents for use as a third layer include agents which are a solvent dissolved polymer or polymerised in situ by some other means than the electrode, as the polymer is not in contact with the electrode. Such agents will be known to the skilled person.

All three electrodes of the sensor may be coated in the third layer. When the electrodes are arranged in needle electrode arrangement, it is preferred if all three electrodes are coated in the third layer.

The electrodes are coated in the third layer preferably only at the distal tip. The electrodes may be coasted further up the electrode shaft/needle, provided it does not inhibit the auxiliary reaction to a great extent The third layer has the surprising advantages of extending the dynamic range of the sensor and to protect against any flow variations, which could occur within the microfluidic chip, affecting mass transport to the biosensor surface, and may be applied by dipping the needle tip into the polyurethane solution (25 mg/ml polyurethane and 0.25 µl/ml Brij 30 surfactant in tetrahydrofuran) twice for 15 s each, leaving the needle to dry upside down for 10 min in between dipping, and for 30 min after the final coating. Due to the high volatility of THF, evaporation of the polyurethane solution is fast and therefore the results from this method can be variable. Whilst the sensors are clearly mass transport limited the dynamic range of the sensors is considerably extended. For lactate sensors this is a highly desirable as physiological concentrations can be higher than the dynamic range of the hydrogel sensors. See the Examples, for example Example 9.

Thus it is considered highly desirable that the hydrogel of the working electrode is covered in the third layer, as this is considered to increase the linear range, and reduce the sensitivity to analysis stream flow rate.

In one embodiment, it is considered that the working electrode has no length, or a negligible length and is an inlaid disc electrode at the tip of the needle. The process of elecropolymerisation will apply the film only where the correct potential to polymerised is applied (ie only at the working electrode).

In one embodiment, where the electrodes are arranged as a needle electrode, the distal tip of the sensor may comprise an angled surface, as discussed above. The angle may, for example be between 90 degrees and 30 degrees to the longest end of the metal shaft, (the auxiliary electrode), for example between 80 degrees and 40 degrees, for example between 70 degrees and 50 degrees, for example 60 degrees. The degree of the angle is determined by the receptacle which holds the sample. For example, when using microfluidics, the channel may only be 500 um deep. In some embodiments the sensor has a diameter of approximately 330 um. In this case, the maximum angle is approximately 30 degrees, otherwise to ensure the entire tip is in the microfluidic device, the tip would be substantially embedded into the far side of the chamber, which is not desirable. The skilled person will be readily able to determine the angle at which the tip should be cut, depending on the rest of the system that the sensor is to be used with. The skilled person will also be readily able to determine which face of the sensor faces the fluid flow. Typically the cut face of the sensor is not on the opposite side of the sensor from the direction of fluid flow.

When the sensor is used in a continuous flow microdialysate system, it is preferred if the electrodes are in the middle of the flow, and not recessed (ie in a side channel out of the main flow) and also not close to the far side of the microfluidic chamber. In one embodiment the tip of the needle electrode is angled such that it contacts the far side of the chamber, ensuring that the working and reference electrodes are in the correct spatial position. For example at a given angle, with the electrodes placed towards the short length of the shaft/auxiliary electrode, contact of the long length of the shaft/auxiliary electrode with the far side of the chamber places the working and reference electrodes at the correct height above the far side of the chamber.

For example, the needle electrode may comprise at least one electrode exposed at a distal end thereof, the needle having a tip extending distally of the at least one electrode by a distance equal to a portion of the diameter of the flow conduit. This is discussed further above.

Preferably the sensor of the present invention is used at constant single potential, giving an amperometric current, and is used in the presence of a continuous flow of analyte.

Although the flow of analyte is continuous, the sampling of the date may not be continuous, but may occur sufficiently fast enough for an effective continuous stream of data. For example the reading from the sensor(s) may be digisited at approximately 200 Hz. The sample can be digitised at as low a frequency as 10 Hz and still give an effectively continuous stream of data. The reading from the sensor may be digitised at much faster rates than 200 Hz. However, it is considered that there is a limit to the usefulness of data obtained over a particular rate. For example, the data should be obtained at a rate sufficiently high enough to rapidly detect changes in metabolite or molecule level, but perhaps not so great a rate as it generates too much non-useful data which may overpower data analysis systems. For example a reading every 10 seconds may be considered acceptable, or an average reading over every 10 seconds, providing an average of continuously obtained data Alternatively, the sensor may be used with dynamic voltametric techniques where the potential is pulsed or scanned, for example Chronamperometry, cyclic voltammetry, and differential pulse voltammetry.

As stated above, it is considered that a more sensitive and accurate reading of the levels of pyruvate can be obtained by assessing the amount of hydrogen peroxide generated when the pyruvate oxidase is added in solution to the dialysate. Therefore, a second aspect of the present invention provides a sensing reagent, in particular a sensing reagent for the detection of pyruvate.

The sensing reagent of the present invention comprises an enzyme, preferably an oxidase enzyme, a buffer and the particular co-factors required for the function of that enzyme for instance a divalent cationic salt such as $MgCl_2$ $MnCl_2$, $CaCl_2$ and $CoCl_2$.

For example, in one embodiment the sensing reagent comprises pyruvate oxidase, Thyamine Pyrophosphate, and $MgCl_2$.

It will be apparent to the skilled person that the pH of the reagent is essential to the stability and performance of the particular enzyme or enzymes (if several enzymes may be used simultaneously, for example in different sensors within the same fluid flow). The preferred pH range of the enzyme(s) will be known from the prior art, or can be determined readily using simple optimisation.

The reagent is typically at a pH of between 6.0, 6.2, 6.4, 6.6, 6.8, 7.0, 7.2, 7.4, 7.5, 7.6, 7.7 or 7.8, for example between pH 6.0 and 7.5, optionally pH 7.0. The reagent may of course be any suitable pH. For example, enzymes such as pyruvate oxidase have a pH range over which their activity is optimal (considered to be between pH 6.0 and 7.5). However, outside of this range the enzyme may still have activity, but a reduced level of activity. Therefore to obtain a similar level of activity from a reagent that has a suboptimal pH, the reagent may comprise a higher amount of enzyme to compensate. For pyruvate oxidase it is considered that the enzyme will have minimal function when pH is less than 5 or above 7.5. Within this range the optimum is 6-7.5 and the optimal pH is 7. This information can be found in the datasheet supplied with the enzyme. Therefore the sensing reagent of the invention may have a pH of between, for example, 5 and 9, for example between 6 and 8, for example 7.4.

Likewise, the preferred working concentration of the enzyme and co-factors can be optimised by for example carrying out an in vitro assay, modifying the concentration of one or more reagents and assessing the effect on enzymic activity.

The reagent will typically comprise agents (enzymes and for example co-factors) that are in a more concentrated form than that required for use, as addition of the reagent to dialysate will inevitably result in dilution of the sensing reagent. Therefore, knowledge of the desired working concentration is required, and with the knowledge of the dilution factor, the desired concentration of agents in the sensing reagent can be determined.

For example, in one embodiment the sensing reagent comprises an enzyme, for example pyruvate oxidase, in a concentration such as to provide a concentration of 0.06 mg/ml to 12 mg/ml pyruvate oxidase, for example 1 to 8 mg/ml, for example 6 mg/ml of added pyruvate oxidase at a unit concentration of 25 U/mg, at the sensor, i.e. in the sensing reaction solution, i.e. once the sensing reagent is mixed with the desired amount of dialysate.

The concentration of the enzyme, for example pyruvate oxidase in the sensing reagent, i.e. prior to dilution with the dialysate, is typically between 0.5 and 50 mg/ml, for example between 5 mg/ml and 45 mg/ml, for example between 10 mg/ml and 40 mg/ml, for example between 15 mg/ml 35 mg/ml, for example between 20 mg/ml and 30 mg/ml, for example 25 mg/ml, wherein the enzyme for example pyruvate oxidase is at a unit concentration of 25 U/mg.

The concentration of the enzyme at the sensor, i.e. following dilution of the enzyme with dialysate, is typically between 1 mg/ml and 10 mg/ml of an enzyme of 25 U/mg, for example between 2 mg/ml and 9 mg/ml, for example between 3 mg/ml and 8 mg/ml, for example between 4 mg/ml and 7 mg/ml, for example between 5 mg/ml and 6 mg/mi. Preferably the concentration is 6 mg/ml.

In a preferred embodiment the concentration of enzyme in the sensing reagent, i.e. prior to dilution with the dialysate is 30 mg/ml (750 U/ml), and in a further preferred embodiment this is used with a constant 0.5 μL/min flow rate, and results in a concentration of enzyme at the sensor of 6 mg/ml (150 U/ml).

It is considered that an enzyme concentration of 30 mg/ml (750 U/ml) is in fact a large excess and that it is possible to reduce the amount of enzyme by a factor of 100 and the reaction would still run to completion. It is considered beneficial if there is sufficient enzyme to ensure a timely completion of the reaction.

In one embodiment the concentration of enzyme, for example pyruvate oxidase, in the sensing reagent is between 0 and 0.5 mg/ml, for example between 0.1 mg/ml and 0.4 mg/ml, for example between 0.2 mg/ml and 0.3 mg/ml, of an enzyme of 25 U/mg.

In one embodiment the concentration of the enzyme at the sensor, i.e. following dilution of the enzyme with dialysate, is between 0.01 mg/ml and 0.1 mg/ml, for example between 0.02 mg/ml and 0.09 mg/ml, for example between 0.03 mg/ml and 0.08 mg/ml, for example between 0.04 mg/ml and 0.07 mg/ml, for example between 0.05 mg/ml and 0.06 mg/ml, for example 0.055 mg/ml, of an enzyme, for example pyruvate oxidase, of 25 U/mg.

Additionally, in one example, the sensing reagent comprises a divalent ion, for example Mn2+, Ca2+, Co2+ or Mg2+, for example $MgCl_2$, in a concentration such as to provide a concentration of 0.00 mM to 20.0 mM, for example between 1.0 mM and 19.0 mM, for example between 2.0 mM and 18.0 mM, for example between 3.0 mM and 17.0 mM, for example between 4.0 mM and 16.0 mM, for example between 5.0 mM and 15.0 mM, for example between 6.0 mM and 14.0 mM, for example between 7.0 mM and 13.0 mM, for example between 8.0 mM and 12.0 mM, for example between 7.0 mM and 11.0 mM, for example between 8.0 mM and 10.0 mM, for example 9.0 mM. It is preferred if the concentration of MgCl2 at the sensor is 16.8 mM i.e in the sensing reaction solution, i.e. at the sensor.

All of Mn2+, Ca2+, Co2+ or Mg2+ are considered to be activators of the enzyme, for example activators of pyruvate oxidase, but it is considered that Mg and Mn are the best.

In one embodiment the concentration of $MgCl_2$ in the sensing reagent, i.e. prior to dilution with the dialysate, is between 0.0 mM and 30 mM, for example between 5.0 mM and 25 mM, for example between 10 mM and 20 mM, for example between 15 mM and 17.5 mM, for example 16.8 mM. In a preferred embodiment the concentration of $MgCl_2$ in the sensing reagent is 16.8 mM, and this is preferably used with a flow ratio (calibration 2 μL/min and enzyme 0.5 μL/min), which results in a concentration of 16.8 mM $MgCl_2$ at the sensor.

It is considered that the enzyme will function without $MgCl_2$ as long as there is TPP. Therefore in one embodiment the concentration of $MgCl_2$ is 0.0 mM in the presence of TPP.

The sensing reagent may comprise TPP in a concentration such as to provide a concentration of between 0.0 mM and 8.0 mM TPP, or for example 1.0 mM-7.0 mM TPP, for example 2.0 mM TPP-6.0 mM TPP, for example between 3.0 mM TPP and 5.0 mM TPP, for example 4.0 mM TPP, in the sensing reaction solution, i.e. at the sensor. Preferably the concentration of TPP at the sensor is 4.8 mM.

The concentration of TPP in the sensing reagent, i.e. prior to dilution with the dialysate, is between 0.0 to 8.0 mM TPP, or for example 1.0 mM-7.0 mM TPP, for example 2.0 mM TPP-6.0 mM TPP, for example between 3.0 mM TPP and 5.0 mM TPP, for example 4.0 mM TPP, in the sensing reagent. Preferably the concentration of TPP at the sensor is 4.8 mM. With a flow rate ratio (calibration 2 μL/min and enzyme 0.5 μL/min) the concentration of TPP in the sensing reagent, i.e. in the reservoir prior to dilution with dialysate is 6 mM TPP.

The concentration of TPP at the sensor, i.e. after dilution with dialysate may be higher than 4.8 mM TPP, as it is considered that a concentration higher than this will give the same results. However it is not considered advantageous if the concentration of TPP at the sensor is lower than this. This of course depends on the exact concentration of for example enzyme, other co-factors and substrate in the dialysate, which the skilled person would be well aware and will take into contemplation when setting up the reagent/system.

In one embodiment, the sensing reagent comprises:
pyruvate oxidase, in a concentration such as to provide a concentration of, for example, 0.06 mg/ml to 18 mg/ml pyruvate oxidase, for example 1 to 8 mg/ml, for example 6 mg/ml of added pyruvate oxidase in the sensing reaction solution, i.e. once the sensing reagent is mixed with the desired amount of dialysate, and $Mg^{2+}$, for example $MgCl_2$, in a concentration such as to provide a concentration of, for example 0.04 mM to 60 mM, for example 16.8 mM of $MgCl_2$ in the sensing reaction solution, and TPP in a concentration such as to provide a concentration of, for example 0.5 to 20 mM TPP, or for example 0.8-8 mM TPP, for example 4.8 mM TPP, in the sensing reaction solution.

In a particular example, the sensing reagent comprises 0.3 mg/ml to 80 mg/ml pyruvate oxidase, 0.2 mM to 70 mM Mg2+, 0.06 to 15 mM TPP, for example 30 mg/ml pyruvate oxidase, 84 mM Mg2+, 25 mM TPP (for mixing at a ratio of 1:4 with the analyte fluid, for example) or 60 mg/ml pyruvate oxidase, 168 mM Mg2+, 50 mM TPP (for mixing at a ratio of 1:9 with the analyte fluid, for example).

Another method of detecting substrates is to use a mediated approach, for example via the addition of multiple enzymes such as horseradish peroxidase and an electrochemical mediator such as ferrocene monocarboxylic acid. This allows use of a lower operation potential (avoiding interferences). Optical mediators such as Texas Red can also be used. Careful sequencing of the addition of the enzymes is required to avoid 'futile mediation' causing a substantial drop in sensitivity.

Given the low concentration of pyruvate in many dialysate samples it may on occasions be desirable to operate a stop/go batch-wise processing using the computer-controlled syringes (as described above). Thus a defined volume of dialysate would be mixed with the novel enzyme mixture and allow to react to completion (that is all pyruvate converted to for example hydrogen peroxide or activated mediator). The concentration of this electrochemically active product can then be determined either using a microelectrode device disclosed above giving a constant current, or, using a larger area electrode, carry our exhaustive oxidation of reduction of the peroxide/mediator. This method would give the total charge hence, if the volume was fixed precisely, inform the user of the concentration without the need for calibration.

However, the sensor described above is considered to be particularly useful for continuous monitoring of a dialysate sample. This requires a steady flow of sample from the subject to be passed across the sensor electrodes. It will be appreciated therefore that the sensor of the present invention may be used in conjunction with a microfluidic flow controller. Both microdialysis sampling and the analysis sensors may be sensitive to flow rate. If the flow rate through the microdialysis probe varies, so too does the probes ability to collect (or recover) molecules from the surrounding tissue. To avoid artefacts in the data, the flow rate through the probe should remain constant. The sensors themselves may also produce artefacts if the flow rate across them changes due to changes in delivery of molecules to the sensor surface rather than concentration. We have developed a computer-controlled environment which is considered to be useful in avoiding or minimising both artefacts.

In a further aspect, the invention provides a sensor system comprising one or more sensors as described herein.

This sensor system may or may not include the sensing reagent as described in the second aspect. For example, when monitoring the levels of pyruvate, it is preferable to provide the pyruvate oxidase in a solution, as disclosed herein, rather than immobilised in a hydrogel on the electrodes. In this case, the system would comprise a sensor with or without a hydrogel, but containing no pyruvate oxidase in the hydrogel. The sensing reagent disclosed herein comprising pyruvate oxidase would be added to the dialysate and then the sensors would sense the produced hydrogen peroxide.

Alternatively, the sensor system may not comprise the sensing reagent, and may comprise an enzyme, for example lactate oxidase, immobilised in the hydrogel according to the first aspect of the invention.

In another embodiment the sensor system comprises more than one sensor disclosed herein, for example may comprise two or more of: a sensor for detecting lactate, in which case the sensor comprises lactate oxidase in the hydrogel; a sensor for detecting glucose, comprising glucose oxidase in the hydrogel; a sensor for detecting pyruvate, which may or may not comprise a hydrogel, and which may or may not comprise pyruvate oxidase in the hydrogel. When the system comprises a sensor for detecting pyruvate but wherein the sensor does not comprise pyruvate oxidase in the hydrogel, the sensor system also comprises a sensing reagent, as disclosed herein.

For example, the sensing solution may comprise pyruvate oxidase, TPP, $MgCl_2$ and a buffer, optionally PBS, citrate buffer or HEPES.

It will be appreciated that lactate oxidase or glucose oxidase, for example, could similarly be provided in a sensing reagent and not immobilised on a sensor. However, it is considered that detection of glucose, lactate and pyruvate in the same sample is best achieved by having glucose oxidase and lactate oxidase present immobilised on respective sensors, and pyruvate oxidase provided in solution, since this is considered to provide optimal sensitivity and minimal interference between the assays for the three analytes.

The sensor system may be used with any sample. For example the sensor system may be used with an environmental sample, or preferably a medical sample such a sample from an animal or human subject. More preferably the sample is from a human or animal subject and is in constant flow. Typically the sample may be obtained by microdialysis, as discussed further below.

In a further embodiment, the sensor system comprises a microfluidic platform in addition to the sensor or sensors and/or sensing reagent as described above. By a microfluidic circuit we include the meaning of a microfluidic platform that may further comprise a microfluidic chip, connectors, junctions and other components necessary to provide a flow of dialysate. Examples of aspects of the microfluidic platform and microfluidic circuit are described above, and provide preferred features of the present microfluidic platform.

The Microdialysis probe used to provide the dialysate for all aspects of the invention may be, for example, a Brain CMA-70 (from MDialysis); a Freeflap CMA-70 (from MDialysis); a MAB9.14.2 (Microbiotech SE); MAB6.14.2 (Microbiotech SE); or MAB11.35.4 (Microbiotech SE).

The sensor system may also further comprise horseradish peroxidase and an electrochemical mediator, for example ferrocene carboxylic acid, or potassium hexacyanoferrate.

It will be appreciated that the sensors and sensor systems can be used in various methods, for example used in a method for the analysis of dialysate from a human or animal subject, the method comprising detection of a metabolite. Therefore, in a further aspect, the invention provides a method for the analysis of dialysate from a human or animal subject. The method of the invention comprises the detection of a metabolite or molecule using a sensor as defined in the first aspect of the invention, or the sensor system according to the third aspect of the invention.

In one embodiment the method is for the analysis of lactate. Typically the hydrogel of one or more of the sensors comprises lactate oxidase.

In another embodiment, the method is for the analysis of glucose. Typically the hydrogel of one or more of the sensors comprises glucose oxidase.

In a further embodiment, the method is for the analysis of pyruvate. The hydrogel of one or more of the sensors may comprise pyruvate oxidase. Alternatively, for example, the analyte fluid is exposed to pyruvate oxidase.

The method may also be for the analysis of lactate and/or glucose and/or pyruvate and/or another one or more metabolites or molecules. The output may be a ratio of different analytes.

The method of the present invention can be carried out on any sample, for example a single sample taken from a subject. Preferably however the sample is a continuous sample extracted from a subject. The sample and/or other fluid may pass continuously over the one or more sensors.

An alternative method for detecting the amount of pyruvate in the dialysate from a human or animal comprises:
adding a sensing reagent for the sensing of pyruvate to the dialysate,
contacting the dialysate and sensing reagent with a sensor according to aspect one, or the sensor system according the second aspect, wherein the sensor does not comprise a hydrogel, or wherein the sensor does comprises a hydrogel but wherein the hydrogel does not comprise an enzyme.

The sensing reagent may be a sensing reagent according to earlier aspects of the invention. Preferably the sensing reagent is sufficient to convert essentially all pyruvate present to acetyl phosphate+$CO_2$+$H_2O_2$ (ie sufficient to provide a largely linear relationship between amount of pyruvate present and amount of hydrogen peroxide generated).

In a preferred method wherein the metabolite or molecule is monitored using a sensing reagent, the sensing reagent is added prior to contacting the dialysate with the sensor.

It is preferred if the enzyme in the sensing reagent is of a sufficient concentration to enable all of the metabolite or molecule in the sample (for example dialysate) to be reacted to completion (to achieve an accurate determination of the metabolite or molecule) in the time between the sensing reagent and the sample being mixed and the mixture reaching the sensor. Thus, the amount of enzyme required may depend on the time between mixing and sensing. Less enzyme may be required if the time of reaction can be extended to allow all of the metabolite or molecule in the dialysate to be reacted to completion to achieve an accurate determination of the metabolite or molecule.

A combination of these factors can be used to arrive at a system comprising a suitable amount of enzyme relative to the amount of dialysate and the time allowed for reaction, to allow the reaction to reach completion.

It is preferable if there is a large excess of enzyme compared to substrate such that the reaction reaches completion quickly. The amount of enzyme required can be readily determined via simple optimisation, which will be apparent to the skilled person. For example, the enzyme may be added to a final concentration of 6 mg/ml (for pyruvate oxidase, for example), which is considered to be an excess of enzyme and will lead to a complete reaction in a short period of time. The enzyme (pyruvate oxidase, for example) may be added to as low as 0.06 mg/ml which is still considered to be an excess and able to lead to an essentially 100% complete reaction, or at least an essentially linear relationship between amount of pyruvate present and amount of hydrogen peroxide generated by the time that the mixture reaches the sensor.

A final concentration of 6 mg/ml pyruvate oxidase is considered to be an approximately 100 fold excess for a reaction time of 30 seconds for the dialysate if the dialysate contained 1 mM pyruvate. Physiological levels of dialysate are considered to be typically about 100 uM or less.

An advantage of excess enzyme is that the reaction is not susceptible to variables such as precise reaction time or temperature.

For example, in one embodiment, the sensing reagent is added at least 1, 2, 5, 10, 20, 25 or 30 seconds prior to contact with the sensor. For example, the sensing reagent may be added to the dialysate in the sensor system sufficiently upstream of the sensor that it takes at least 1, 2, 5, 10, 20, 25 or 30 seconds before the dialysate/sensing reagent mix reaches the sensor. This time will be dependent on the flow rate and can easily be determined by the skilled person.

For example, taking account of the flow rate and the desired time of arrival at the sensor, the sensing reagent may be added a particular distance upstream of the sensor. For example the sensing reagent may be added 8 cm upstream of the sensor when the sensing reagent is added at a flow rate of 0.5 ul/min in a 150 um internal diameter tube, and the flow rate of the dialysate is 2 ul/ml in a 120 um diameter tube. In this situation it is considered that it takes 30 seconds for the reagent and dialysate to reach the sensor.

The method wherein the pyruvate is detected using a sensing reagent can be used in conjunction with the earlier method, in which a metabolite, for example lactate and/or glucose is detected using a sensor comprising a hydrogel comprising an enzyme. Therefore in one embodiment the method is for the analysis of lactate, glucose and pyruvate, wherein the lactate is monitored using a sensor comprising a hydrogel comprising lactate oxidase, the glucose is monitored using a sensor comprising a hydrogel comprising glucose oxidase, and the pyruvate is monitored using a sensor which may or may not comprise a hydrogel, but wherein the hydrogel does not comprise an enzyme.

In a preferred embodiment of either method, at least two parameters are monitored by the sensing system, for example at least two of glucose, lactate and pyruvate are analysed. In one embodiment the absolute levels of a particular metabolite or molecule are monitored. The absolute levels may be compared to a standardised value, for example to a value corresponding to the population average value. The absolute level may also be compared to the patient's own value from, for example, a sample from another tissue, for example from a tissue that is considered unlikely to be affected by the factor under investigation. Alternatively, the absolute value may be compared to one or more values taken from the same subject from the same tissue, for example from the same site, at a time prior to the value now obtained.

However, absolute levels are considered to be difficult to determine given their dependency on dialysis flow rate, microdialysis probe membrane area and tissue properties. Therefore, in an alternate example, the absolute levels of a particular metabolite are not considered to be critical, rather it is the relative levels, or the ratio of metabolites that is important, and in particular the way that the ratio of the metabolites changes over time. In one embodiment the relative levels of three or more metabolites are monitored, for example the levels of all of lactate, glucose and pyruvate. For example the relative percentage change, or determination of the area under the curve excesses or deficits for each metabolite or molecule, or ratio of two metabolites or molecules is considered to be preferable. Ratio changes are also considered to be more useful as they can used to compare patients more reliably.

For example the ratio between lactate and pyruvate, or lactate and glucose are considered to be important metrics as they are less sensitive to artefacts in the data, such as that caused by changes in probe recovery. In particular, the lactate/glucose ratio has been shown to be an especially sensitive marker of tissue health, providing a clear indication as to whether tissue energy demands are being met.

On seeing that the tissue glucose was low an iv injection of glucose could be give (likely to clash with a diabetic patient, though this may not be a particular concern if the patient is otherwise likely to die from the brain injury in the absence of intervention), but in the TBi situation if glucose level is low the flux of glucose into the injured tissue can be increased, for example the blood pressure could be increased to improve cerebral perfusion pressure, or by increasing the concentration of glucose in the blood, for example by the administration of glucose. For a pharmaceutical compound designed to improve tissue state or counteract ongoing tissue pathology. The effect and time course of the drug could be determined from the measures of the system.

Further aspects of how the microdialysis probe may be operated, the results that may be achieved and how they may be acted on are set out in Example 7.

In a preferred embodiment, the dialysate is a microdialysate, preferably extracted from a subject in a continuous flow. The microdialysis probe may be as indicated above.

The microdialysate may be analysed in a polymeric microfluidic chamber.

It is preferred if the method of analysis is performed using a control system for controlling the movement of the microdialysate into and out of the microfluidic chamber.

In certain situations, it is preferable if the metabolite(s) or molecule(s) are monitored continuously for a prolonged period. For example the method may comprise monitoring the metabolite(s) or molecule(s) for at least one hour, four hours, 12 hours, 24 hours, 48 hours, 72 hours, four days, five days, six days or more, for example 1 week, 2 weeks, 3 weeks, 4 weeks, 1 month, 2 months, 4 months, 6 months or 1 year or more. This continuous monitoring may be interrupted for periods of calibration. The calibration may take up to about 60, 50, 40, 30, 20 or 10 minutes, and the calibration may be performed at intervals of between 0.5 and 12 hours, for example between 1 hour and 11 hours, or between 2 hours and 10 hours, or between 3 hours and 9 hours, or between 4 hours and 8 hours, or between 5 hours and 7 hours, or for example 6 hours.

The method can also further comprise a step of comparison of the sensor readings, for example over time, and the identification of a trend that may be associated with a clinical pathology.

FIGURE LEGENDS

FIGS. 8a to 8c show: (a) a cross-sectional view through a part of the analysis module of FIG. 6; (b) enlarged detail K of FIG. 8a; and (c) a top view of the part of the analysis module in FIG. 8a;

Figure 1:
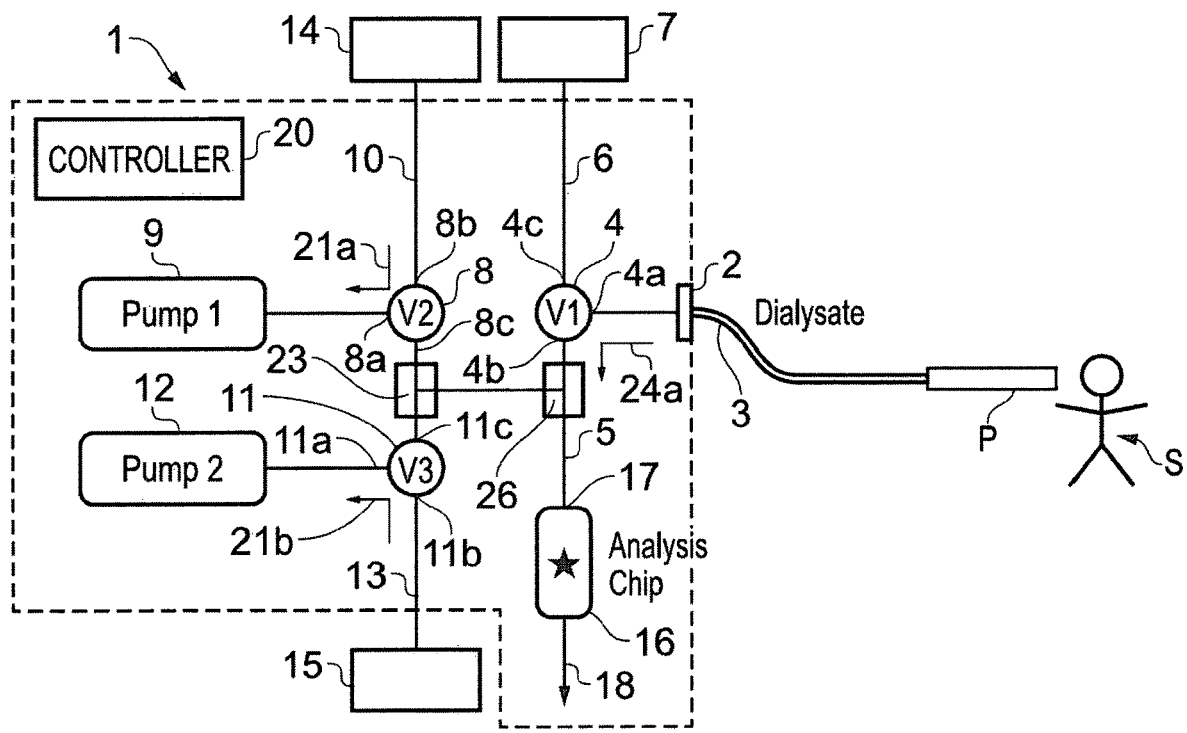
FIG. 1 is a schematic functional block diagram of a microfluidic flow controller configured to maintain a steady flow of fluid through an analyte conduit during analysis and calibration, showing the flow controller in analysis mode.
Figure 2:
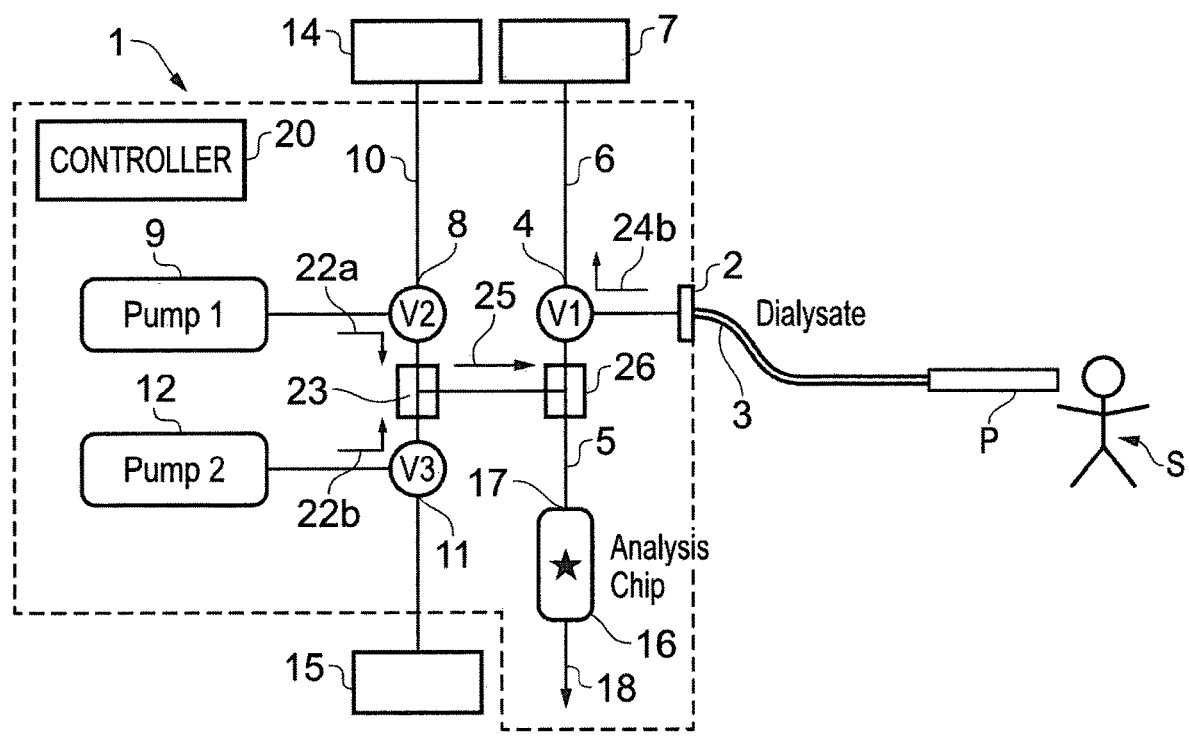
FIG. 2 is a schematic functional block diagram of the flow controller of FIG. 1 in calibration mode.
Figure 3:
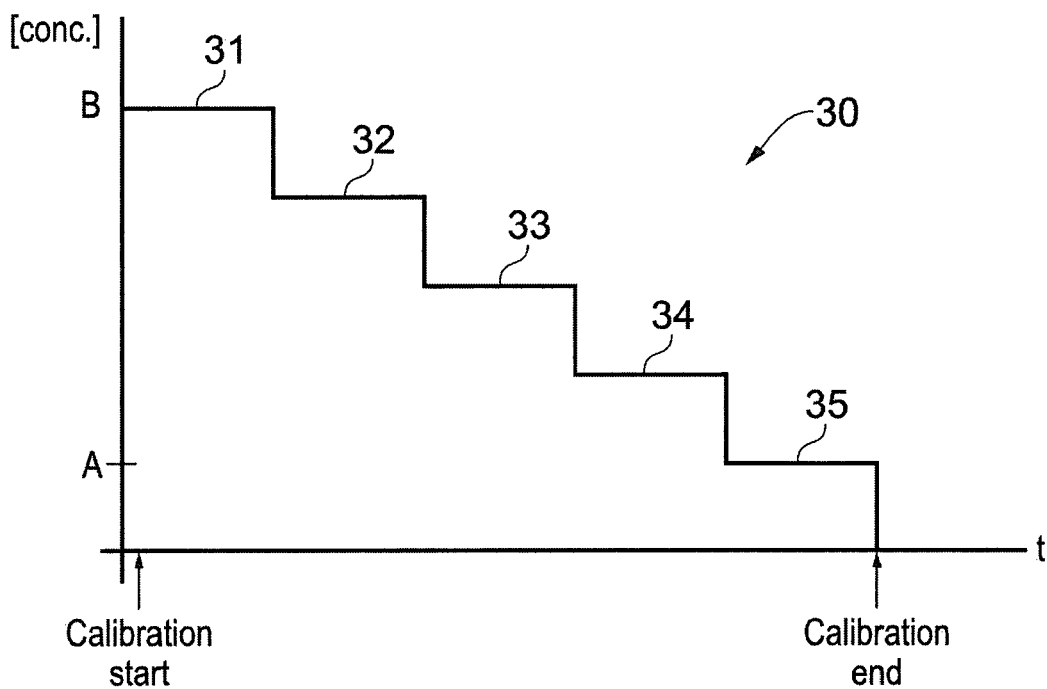
FIG. 3 is a calibration fluid concentration profile as a function of time illustrating a possible calibration process performed by the flow controller of FIGS. 1 and 2.
Figure 5:
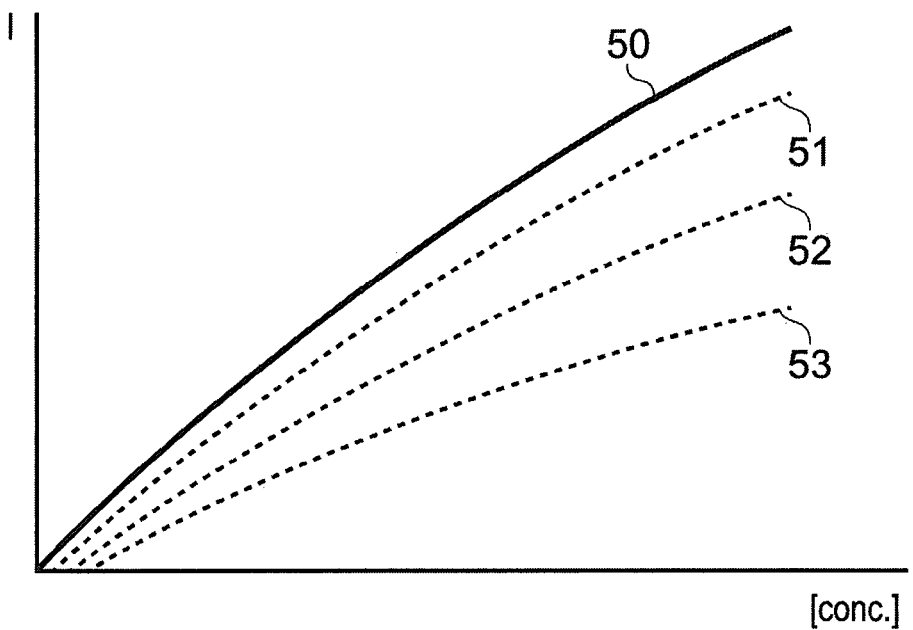
FIG. 5 is an illustration of the change in calibration profiles relating electrical current and analyte concentration as a function of time used in an autocalibration process.
Figure 4:
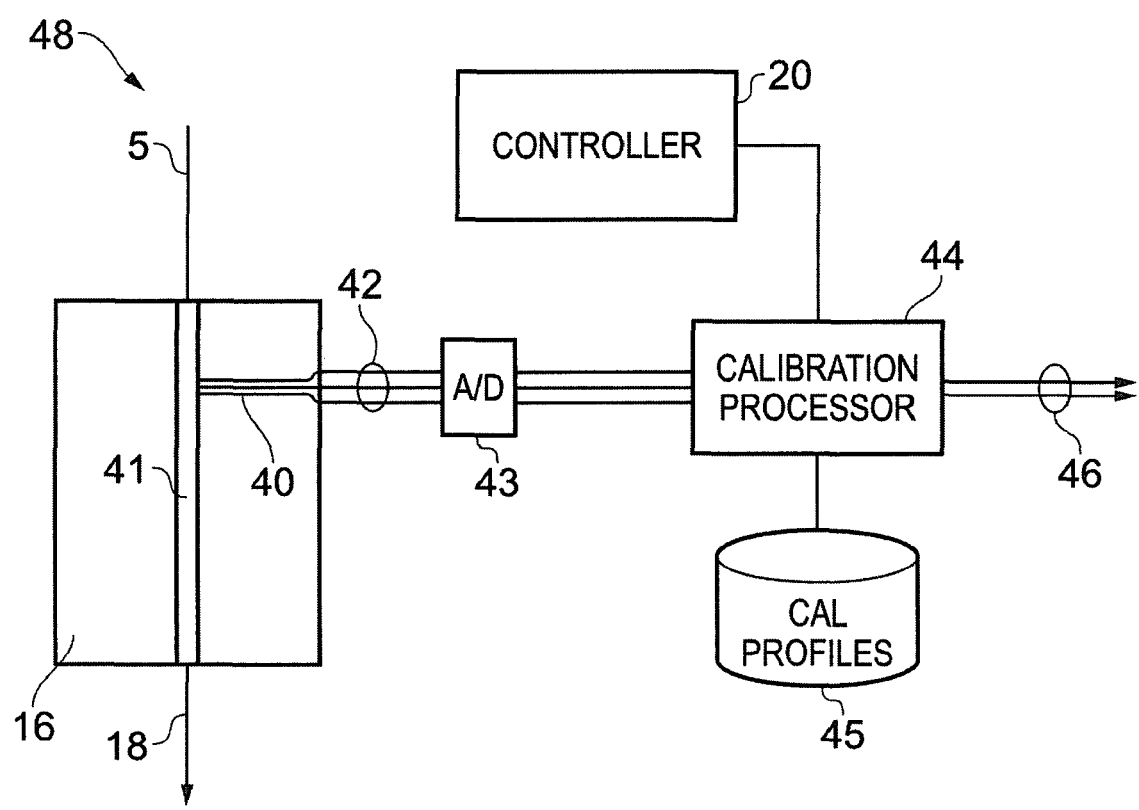
FIG. 4 is a schematic functional block diagram of a microfluidic analysis apparatus for enabling automatic calibration of an analysis module such as that in the system of FIGS. 1 and 2.
Figure 7:
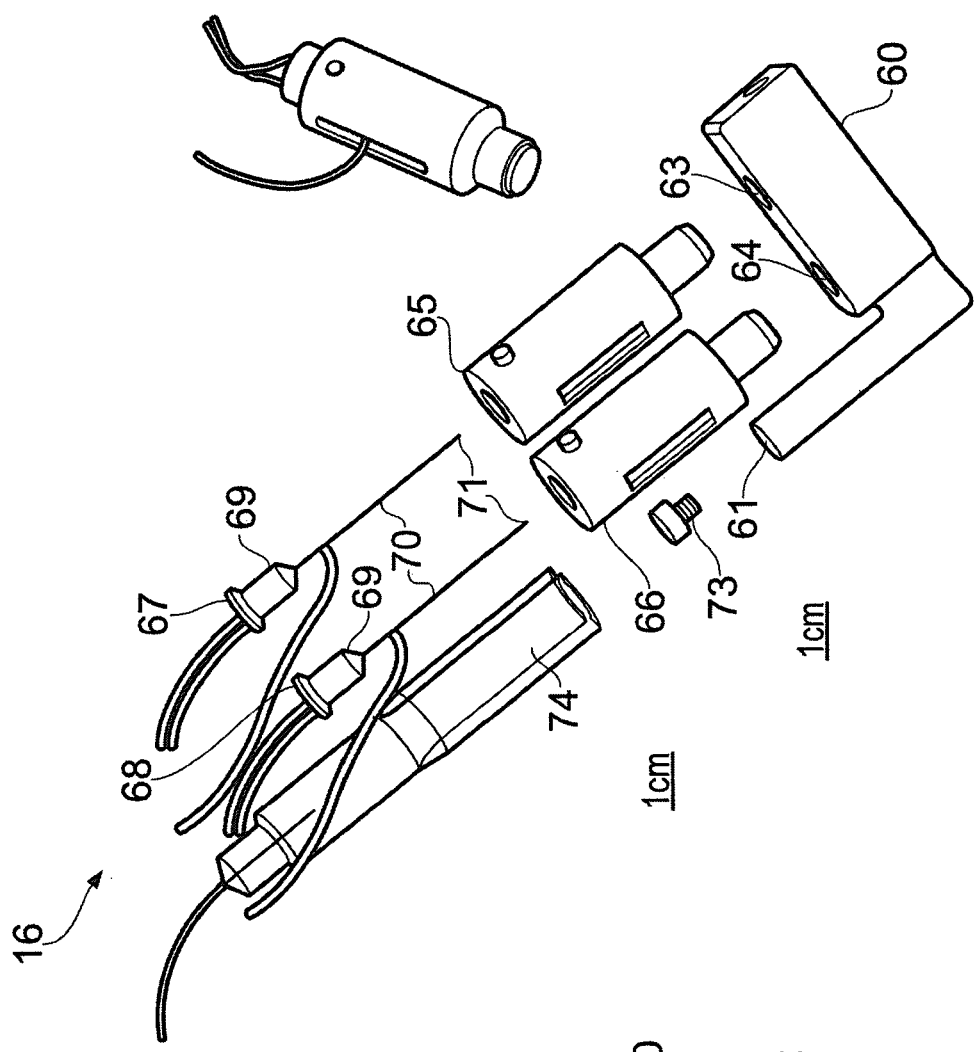
FIG. 7 is a perspective view of the analysis module of FIG. 6 with the components separated for clarity.
Figure 6:
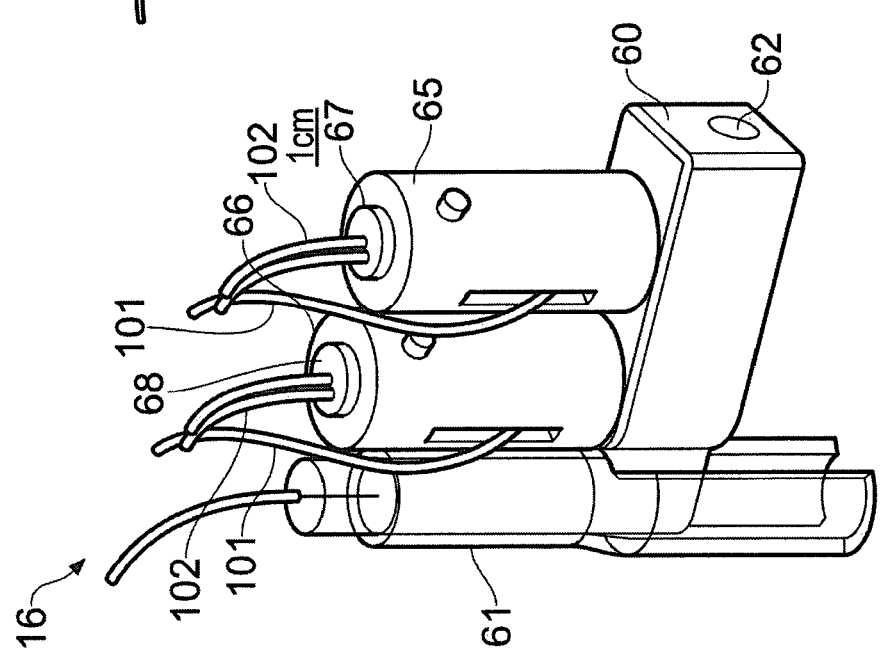
FIG. 6 is a perspective view of an analysis module suitable for use with the flow controller of FIG. 1.
Figure 8:
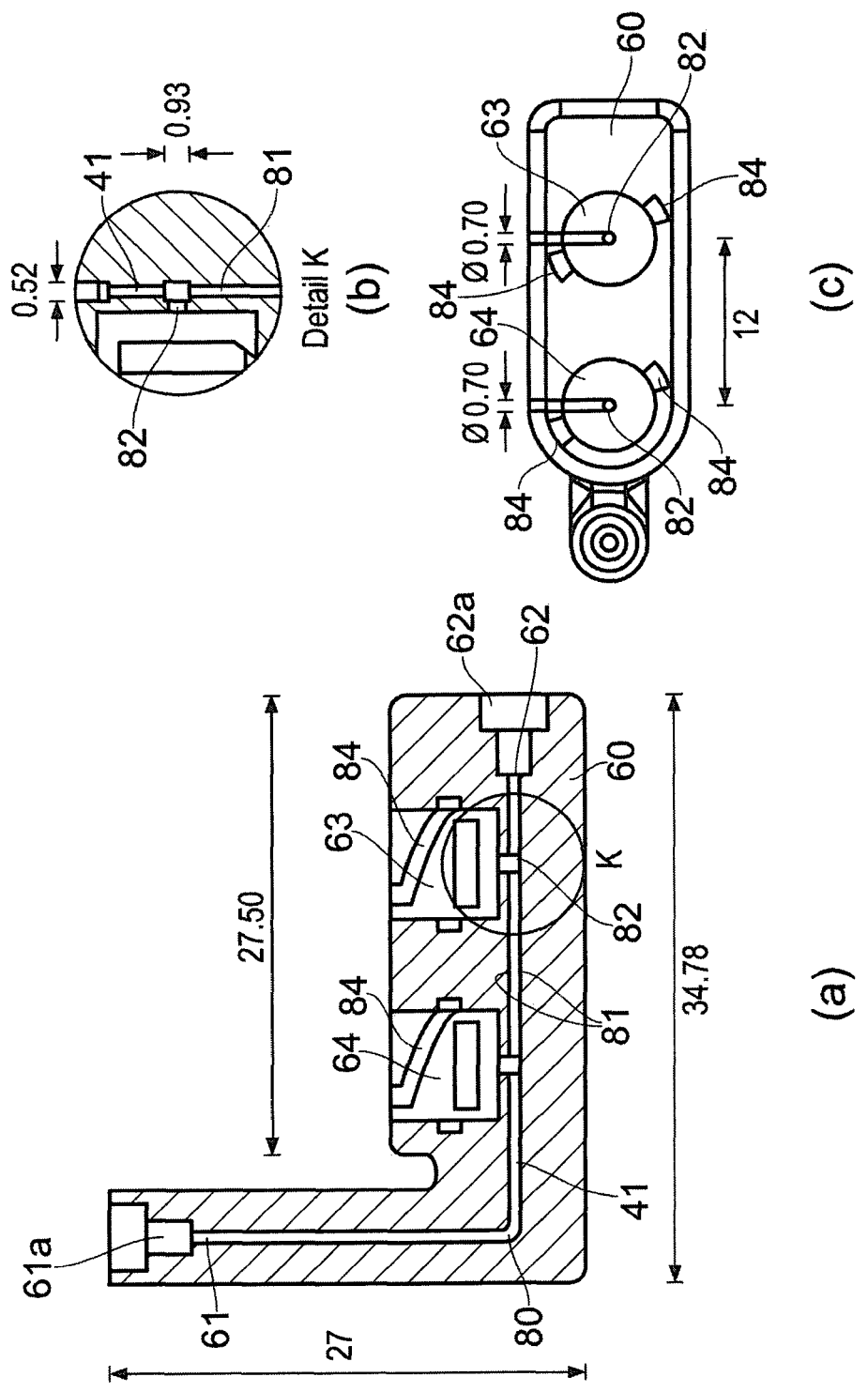
Figure 9:
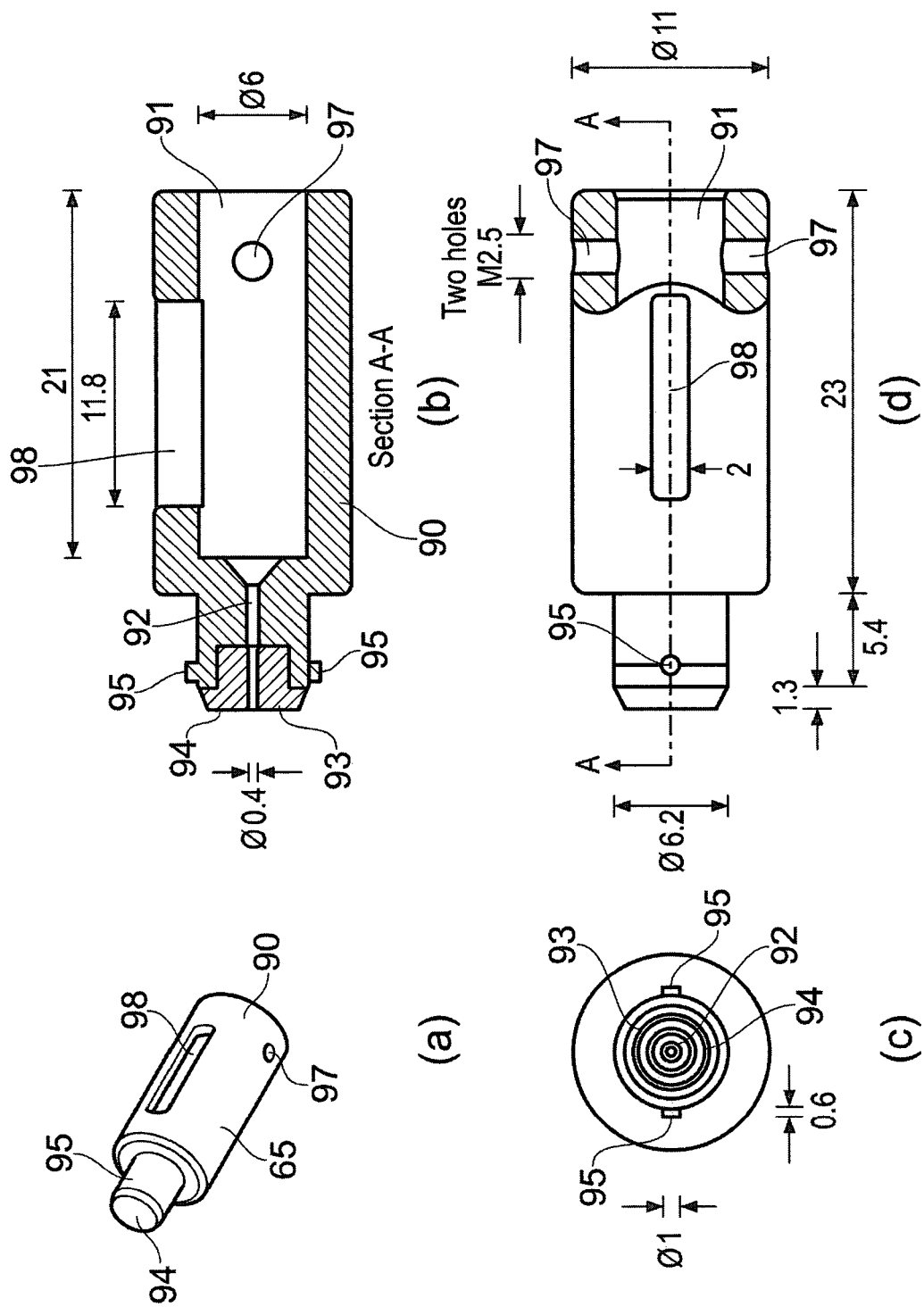
FIGS. 9a to 9d show: (a) a perspective view of an sensor holder of the analysis module of FIG. 6; (b) a cross-sectional side view of the sensor holder of FIG. 9b; (c) a distal end view of the sensor holder of FIG. 9c; and (d) a side view of the sensor holder of FIG. 9a with partial cut-away.
Figure 11:
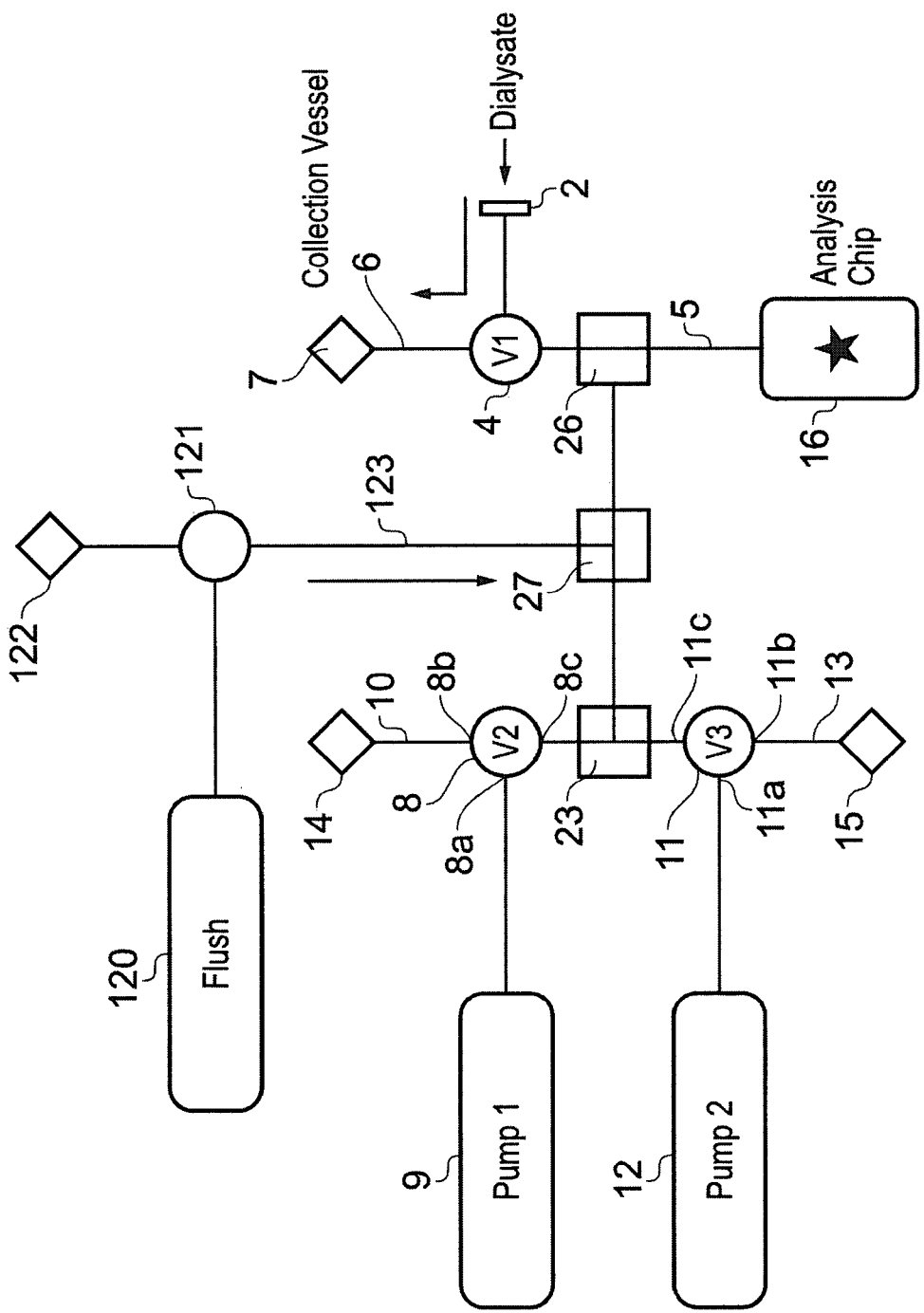
Figure 12:
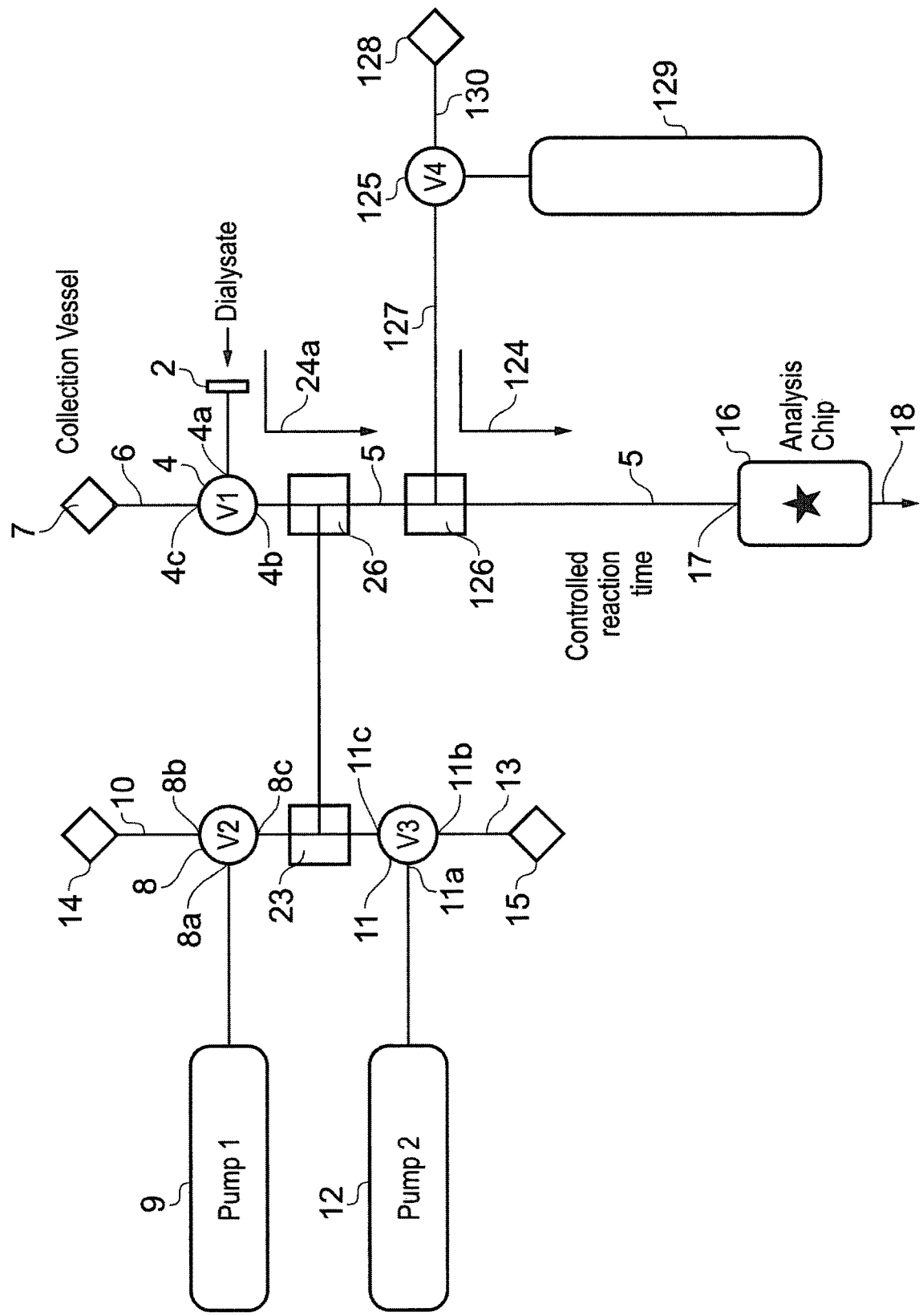
Figure 13:
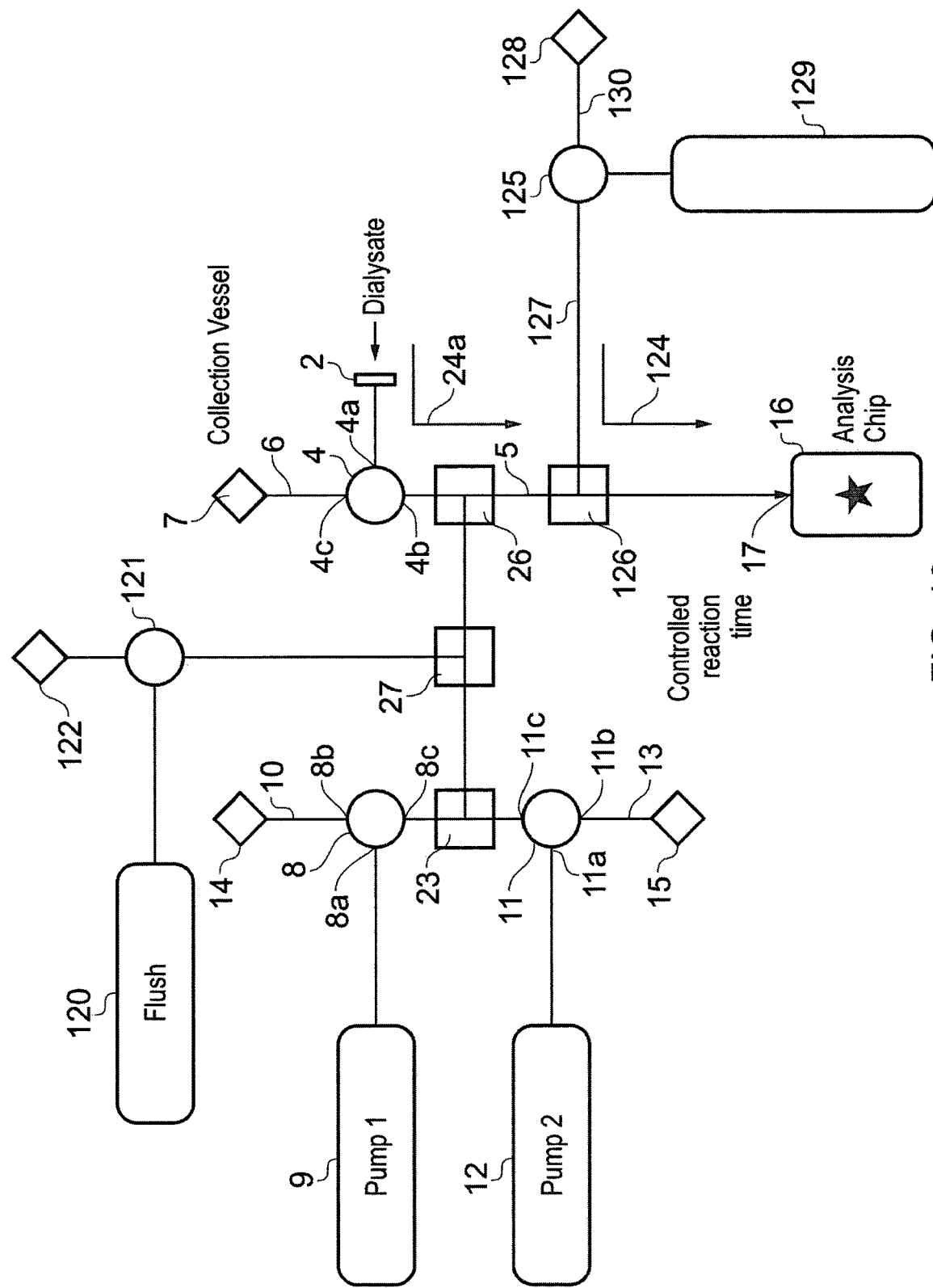

FIG. 10A shows a cross-sectional side view of an alternative sensor holder; FIG. 10B shows a cross-sectional side view of the sensor holder of FIG. 10B coupled to its base block, with inset plan views showing locked and unlocked positions; and FIG. 10C shows a cross-sectional end view of the sensor holder in position in an aperture of an analyte flow channel, with inset plan views of the locked and unlocked assembled apparatus;

FIG. 11 is a schematic functional block diagram of a variation in the configuration of microfluidic controller shown FIG. 1, including an analyte conduit flushing arrangement;

FIG. 12 is a schematic functional block diagram of a variation in the configuration of microfluidic controller shown in FIG. 1 including a reagent delivery system upstream of the analysis module;

FIG. 13 is a schematic functional block diagram of a microfluidic controller similar to that of FIG. 1 incorporating both analyte conduit flushing system and reagent delivery system.

Figure 14:
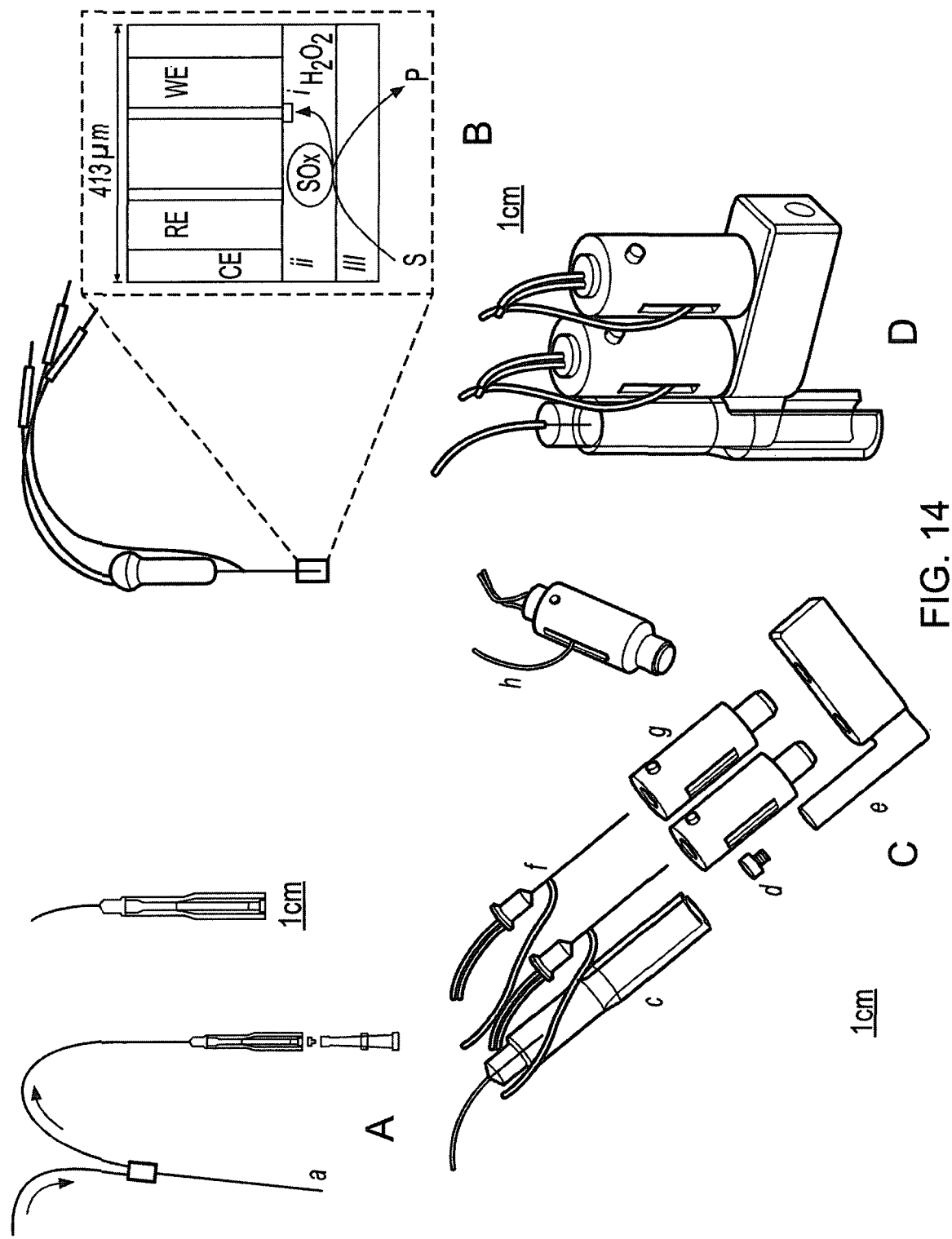

FIG. 14. A. Standard microdialysis set-up for discrete sampling. The probe (a) is perfused at a fixed low flow rate, and dialysate is collected into a microvial (b) at the probe outlet. Right: shows the microvial when connected to the probe holder. B. Photograph of combined needle electrode based on a 27 G hypodermic needle and schematic cross-section of the needle tip, showing the layers that make up the biosensor: (i) m-PD exclusion layer, (ii) substrate oxidase (SOx) entrapped in a hyrodgel and (iii) diffusion limiting polyurethane outer film. C. Exploded view of custom-made microfluidic device for continuous monitoring of dialysate, showing the multi-component system. The microfluidic chip (e) connects to the probe outlet holder (c) in place of a microvial. The outlet holder needle enters the microvial rubber insert (d) at the inlet of the microfluidic chip. Glucose and lactate needle biosensors (f) are housed in custom-made electrode holders (g) that screw into the microfluidic chip, placing the biosensors in the middle of the microfluidic channel, and providing a good seal between the holder and the microfluidic device. (h) shows a photograph of electrode holder containing needle biosensor. The black part at the base of the holder is made of soft, compressible plastic to ensure the holder makes a good seal with the microfluidic chip. D. The L-shaped design provides a tidy and compact overall system.

Figure 15:
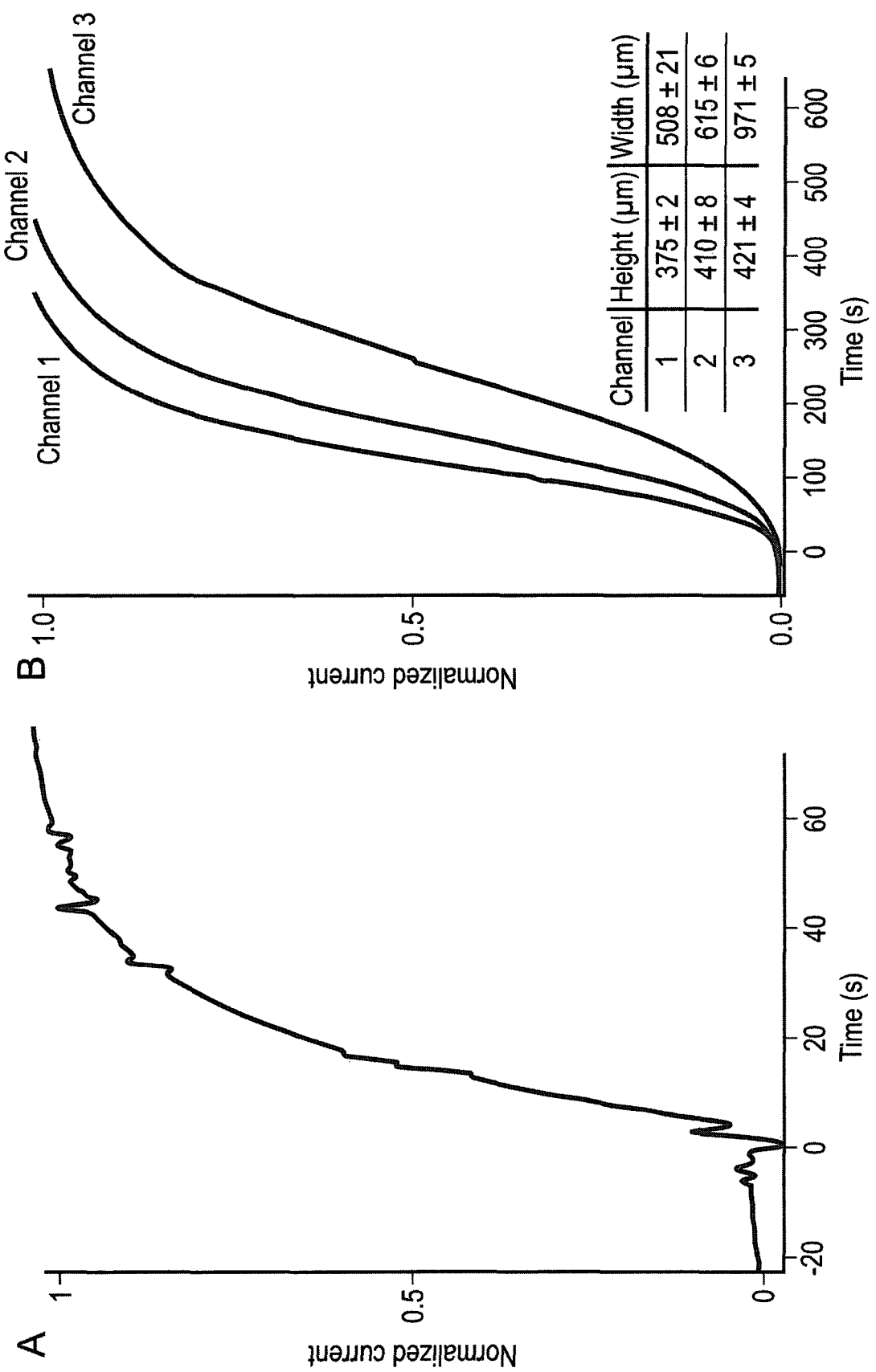

FIG. 15 A. Normalized current response of a 50 μm disc lactate biosensor in a stirred beaker to a 2 mM lactate concentration step (purple arrow). B. The graph shows the normalized current for a glucose biosensor to a step change from 0 to 2 mM at 1 μl/min in three different microfluidic channels. The measured channel sizes are shown in the table inset. The response time increases as the channel dimension increases.

In the subsequent figures the data comes from an integrated three electrode biosensor. The size (often 50 μm) indicates the size of the working electrode.

Figure 16:
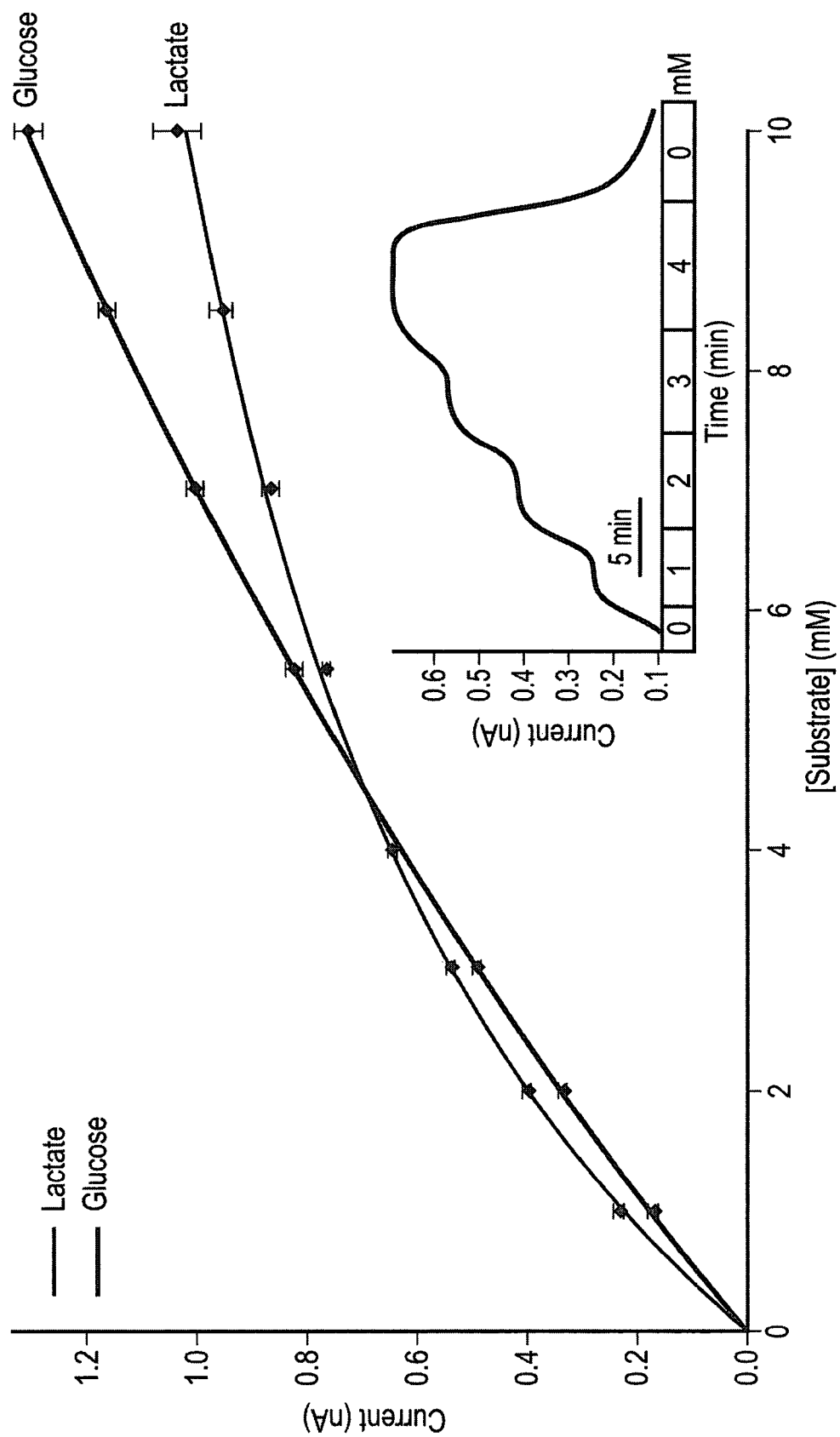

FIG. 16. Typical calibration curves for 50 μm disc glucose and lactate biosensors in the microfluidic device at 1 μl/min. Mean±standard deviation of measurement shown (n=4).

Points fitted with the Michaelis-Menten equation. Inset: Raw data for a typical 5-point lactate calibration from 0 to 4 mM in 1 mM steps.

Figure 17:
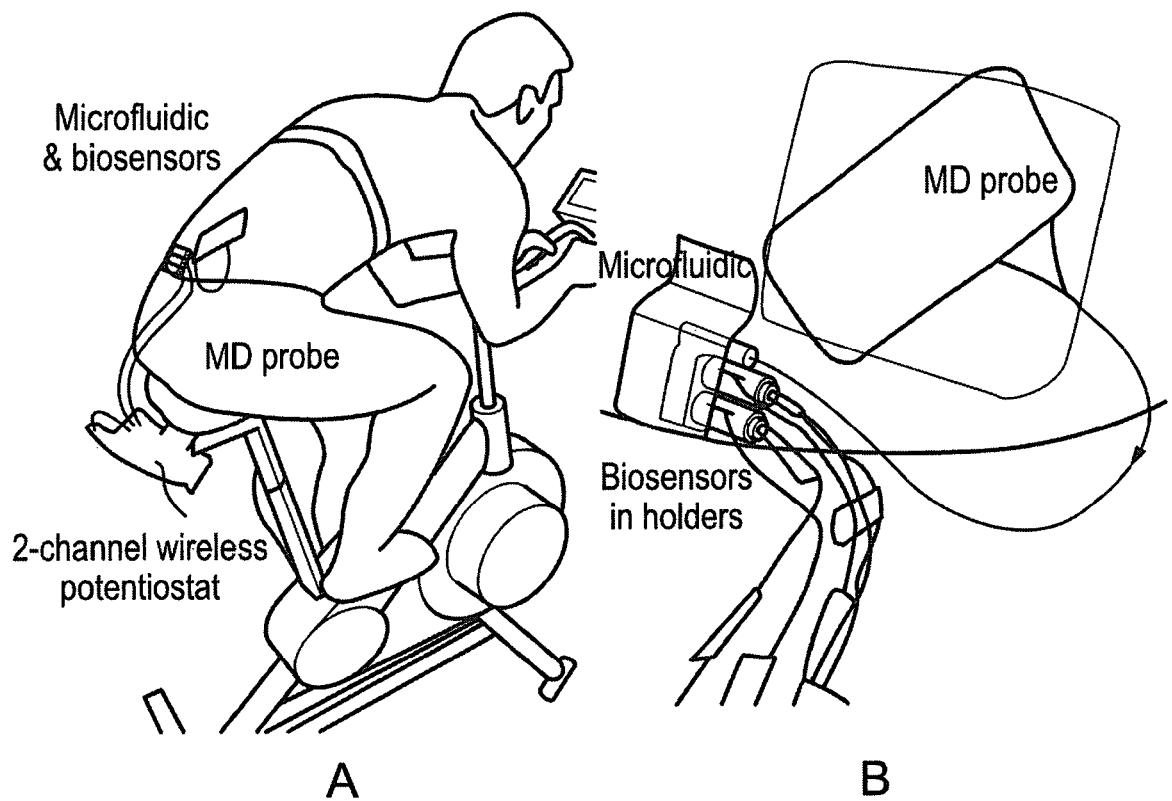
Figure 17:
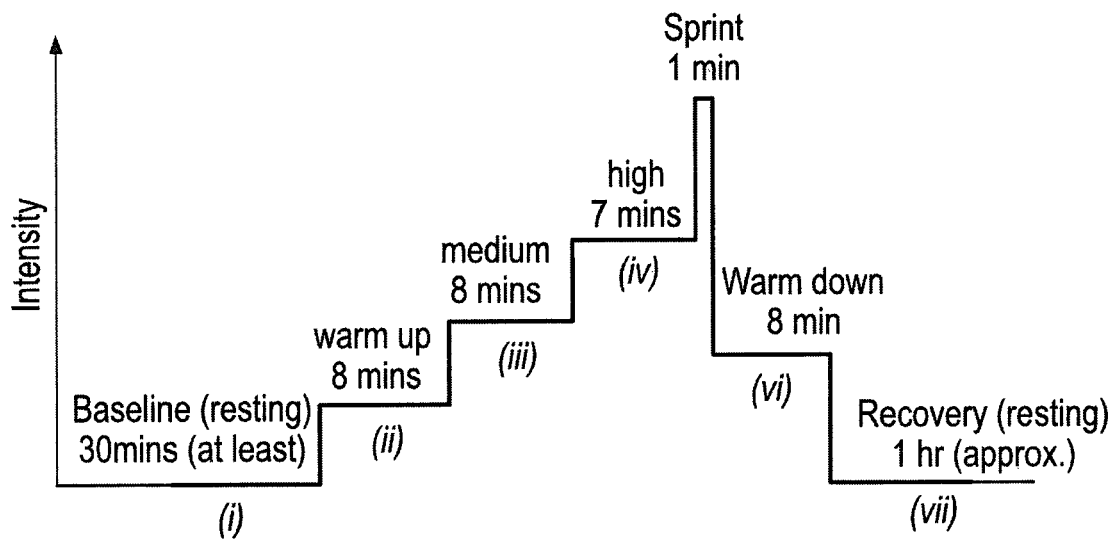
Figure 17:
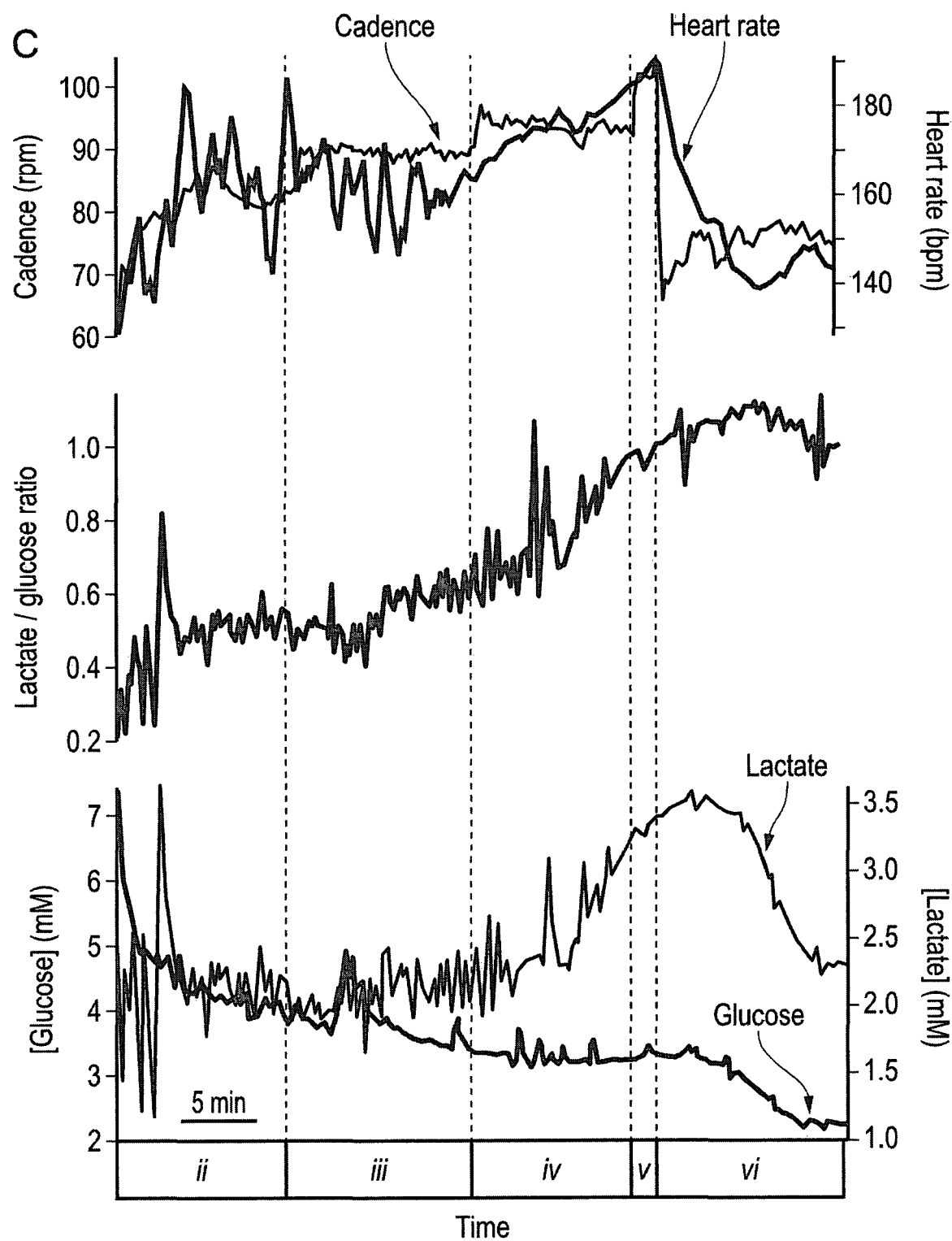
Figure 17:
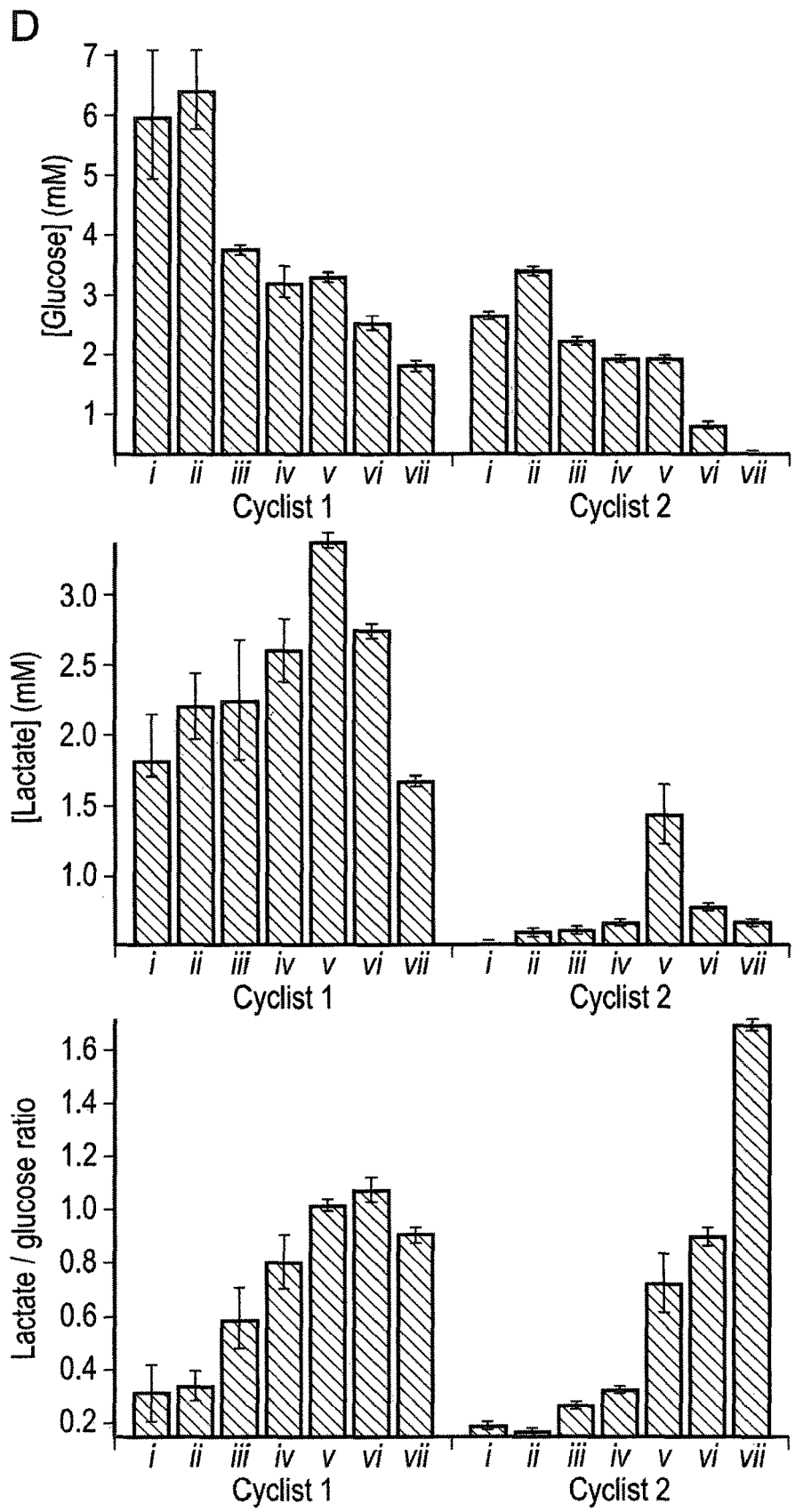

FIG. 17 A. Photograph of microfluidic device to measure tissue glucose and lactate levels in dialysate during cycling protocol. Dialysate flowed into the microfluidic chip, housing the glucose and lactate biosensors, which were connected to wireless potentiostats, secured onto the bike. B. Experimental protocol. Tissue levels were monitored during an initial resting period (i), followed by cycling at 4 levels of increasing rpm (ii-v), a level of warming down (vi) and a final period of resting (vii). C. Dialysate glucose and lactate levels during the exercise phase of the cycling protocol. The bottom graph shows the glucose (red) and lactate (green) levels, the middle graph (black) shows the lactate/glucose ratio, and the top graph shows the rotations per minute (blue) and heart rate (purple) throughout the cycling protocol. Glucose and lactate traces have been despiked.38 The dotted lines indicate the stages of varying cycling intensity: (ii) 55 rpm, (iii) 65 rpm, (iv) 75 rpm, (v) sprint, and (vi) 55 rpm. Data has been time-aligned, taking into account the time delay of the system. D. Histograms showing mean dialysate levels for two different cyclists during key points in cycling protocol. Labels correspond to stages described in the experimental protocol: (i) baseline (ii) midway through warm up, (iii) midway through medium intensity, (iv) midway through high intensity, (v) end of sprint, (vi) end of warm down and (vii) after 50 mins of recovery.

Figure 18:
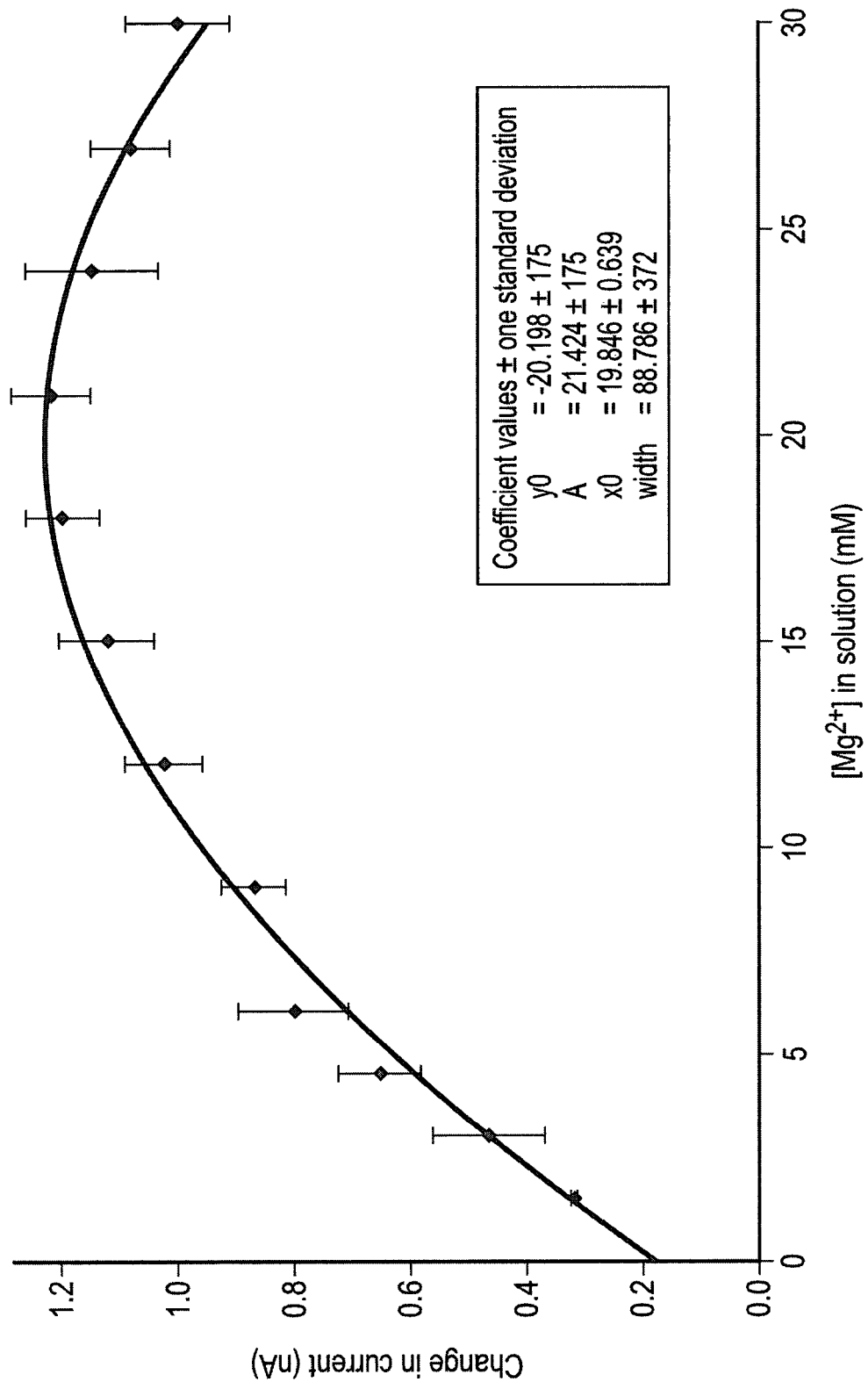
Figure 18:
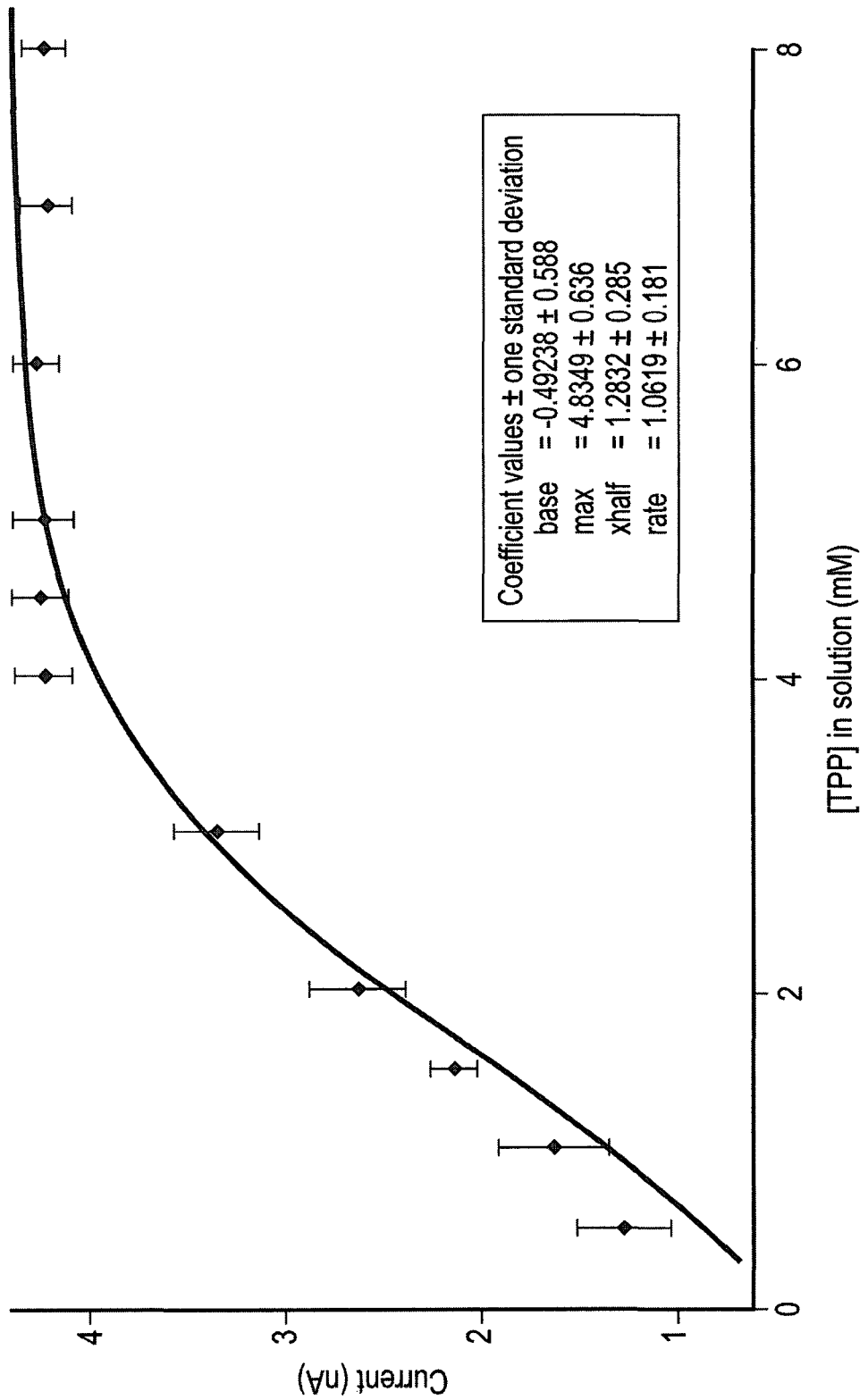
Figure 18:
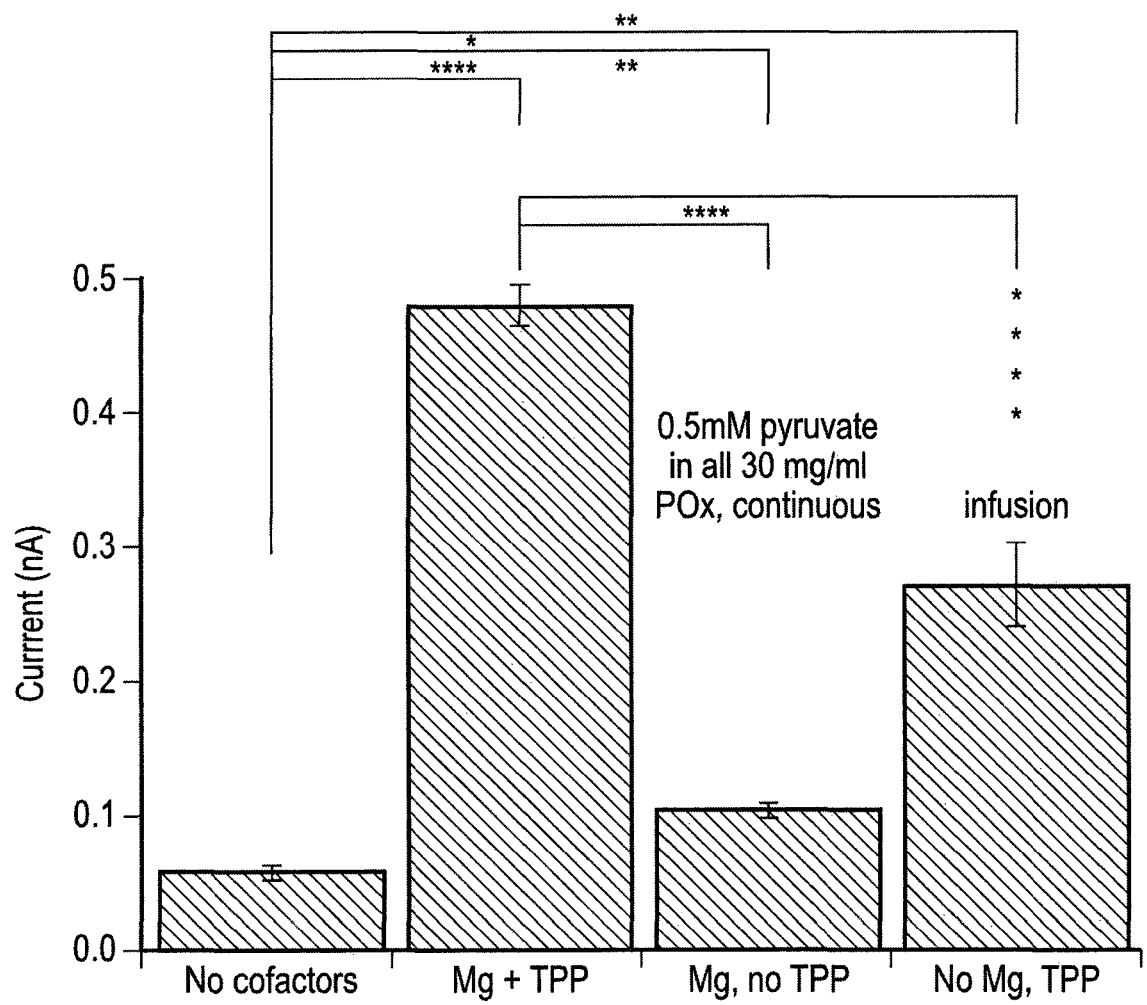
Figure 18:
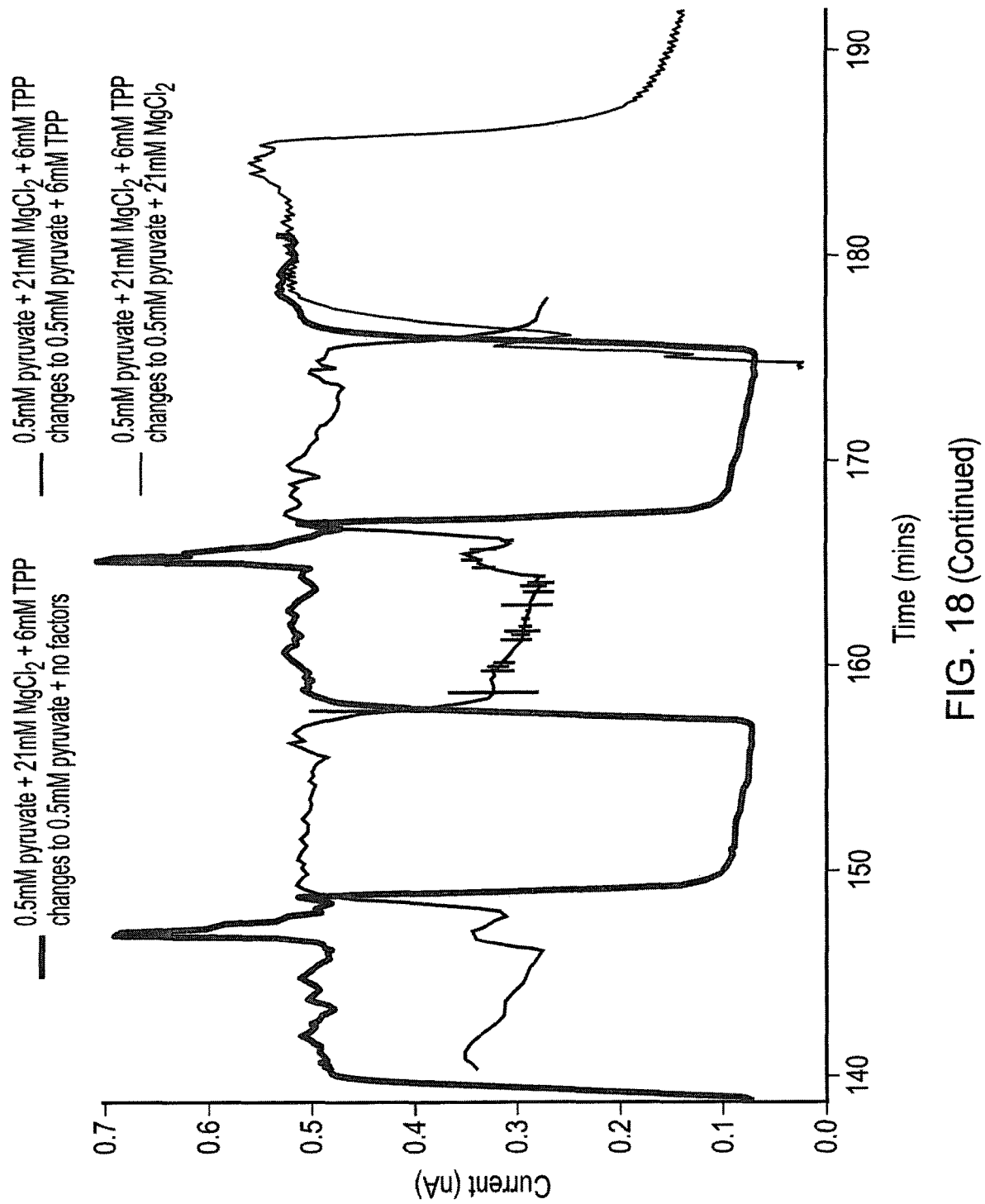

FIG. 18—The concentration of both the enzyme, pyruvate oxidase, and the substrate, pyruvate, was kept constant (30 mg/ml and 0.5 mM respectively) and individually the concentration of each cofactor (Mg2+ and TPP) was varied. The response to increasing the concentration of each cofactor is shown (VaryMg and VaryTPP). Thus, the optimised levels of each were 21 mM Mg2+ and 6 mM TPP.

In a separate experiment, the mixture was varied to contain the cofactors individually or both together for a direct comparison of signal output.

Figure 19:
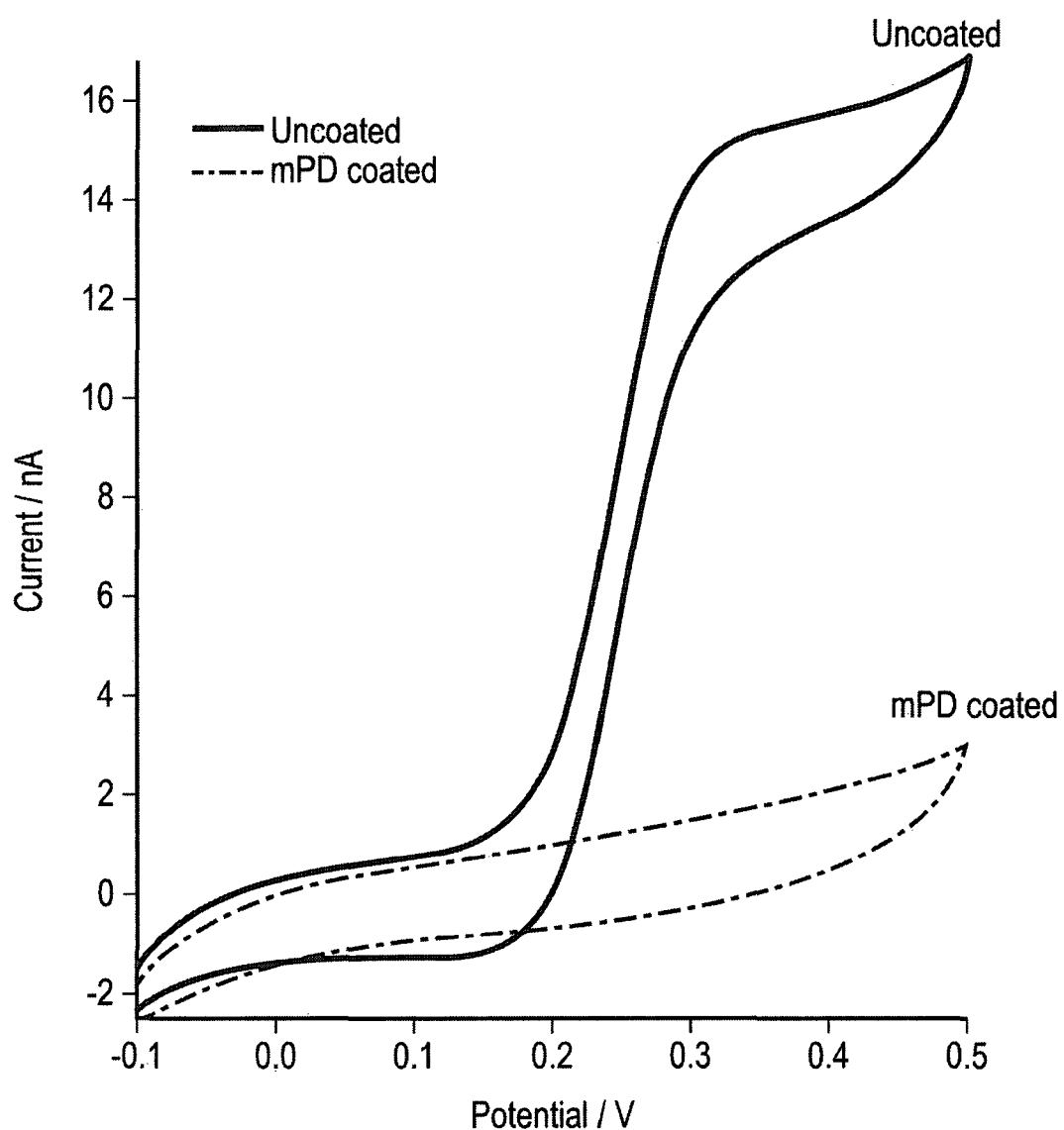

FIG. 19. Cyclic voltammograms assessing the surface of the working electrode. The potential was ramped at a scan rate of 50 mV/s in a solution of 1.5 mM ferrocene monocarboxylic acid. In red, the CV of a 50 µm bar platinum electrode is shown and in blue the CV of an mPD-coated electrode is shown. The presence of the mPD film over the electrode means that the ferrocene monocarboxylic acid molecules cannot reach the electrode surface.

Figure 20:
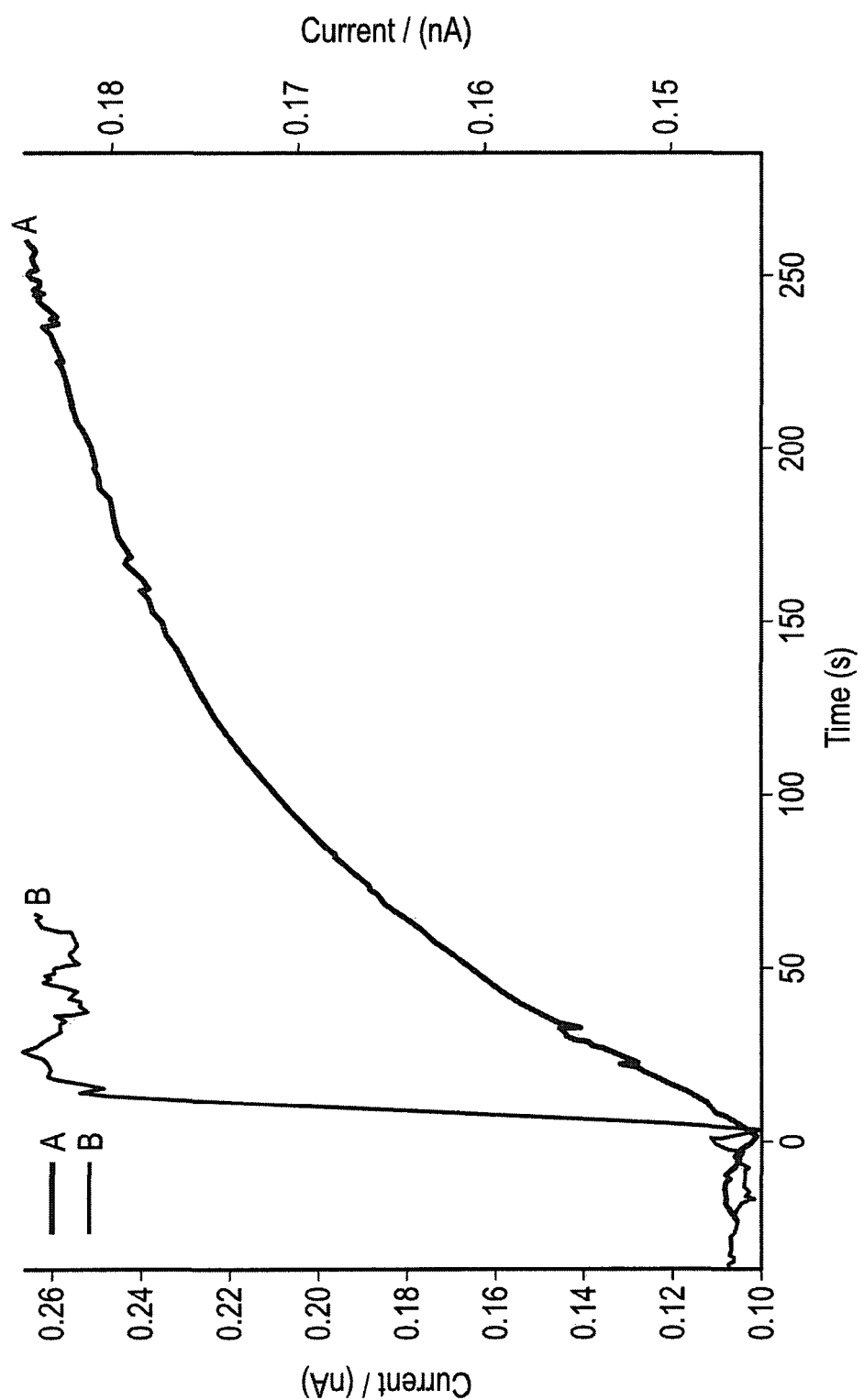

FIG. 20. Response from an optimally coating sensor B and a sub optimally coated sensor A versus time. Time zero is when the concentration was changed from 2 mM to 4 mM lactate.

Figure 21:
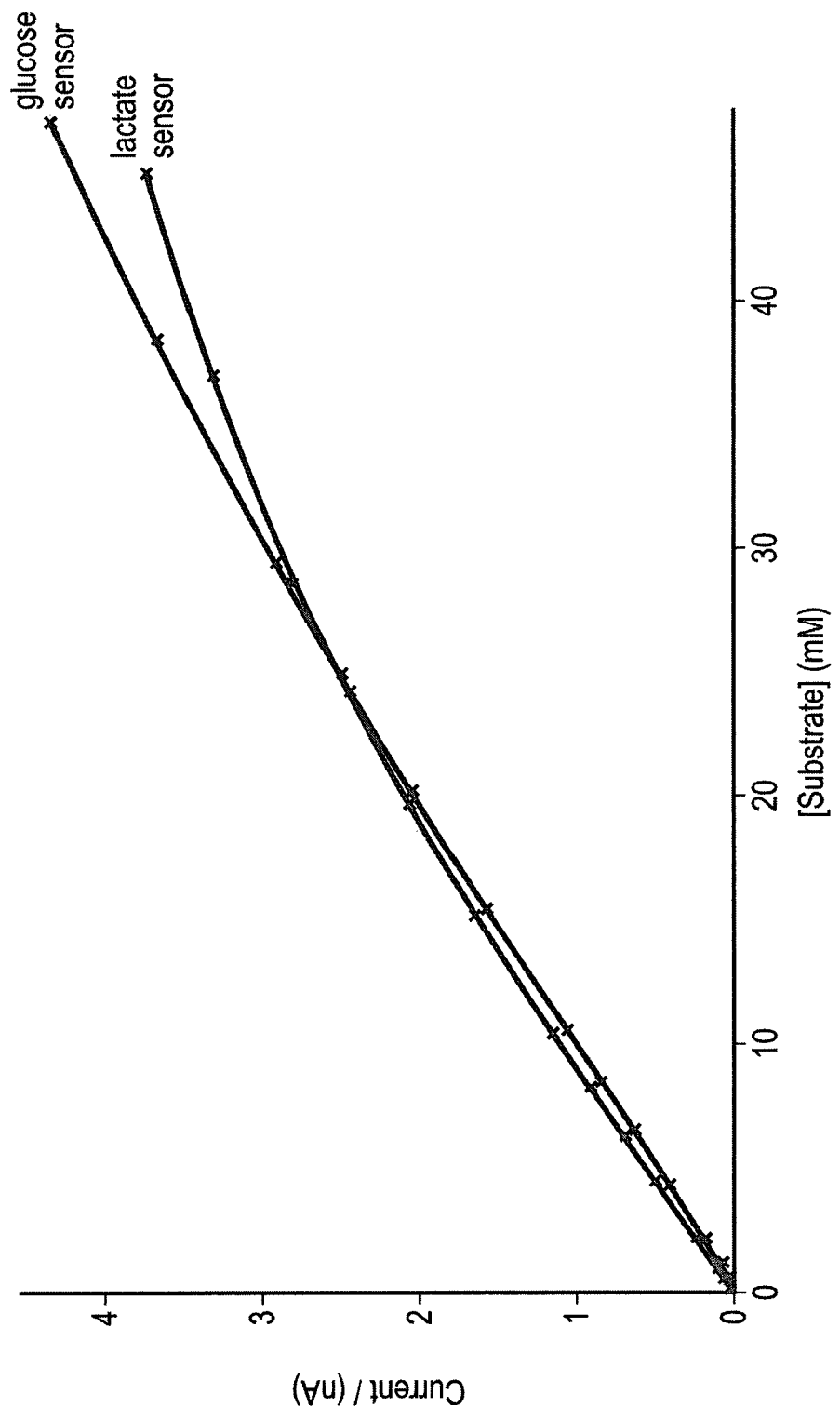

FIG. 21: Polyurethane was also added to the glucose sensor. Typical responses from the sensors with polyurethane layer added are shown, where green is the response from the lactate sensor, and red is the response from the glucose sensor. Clearly the sensors are mass transport limited.

Figure 22:
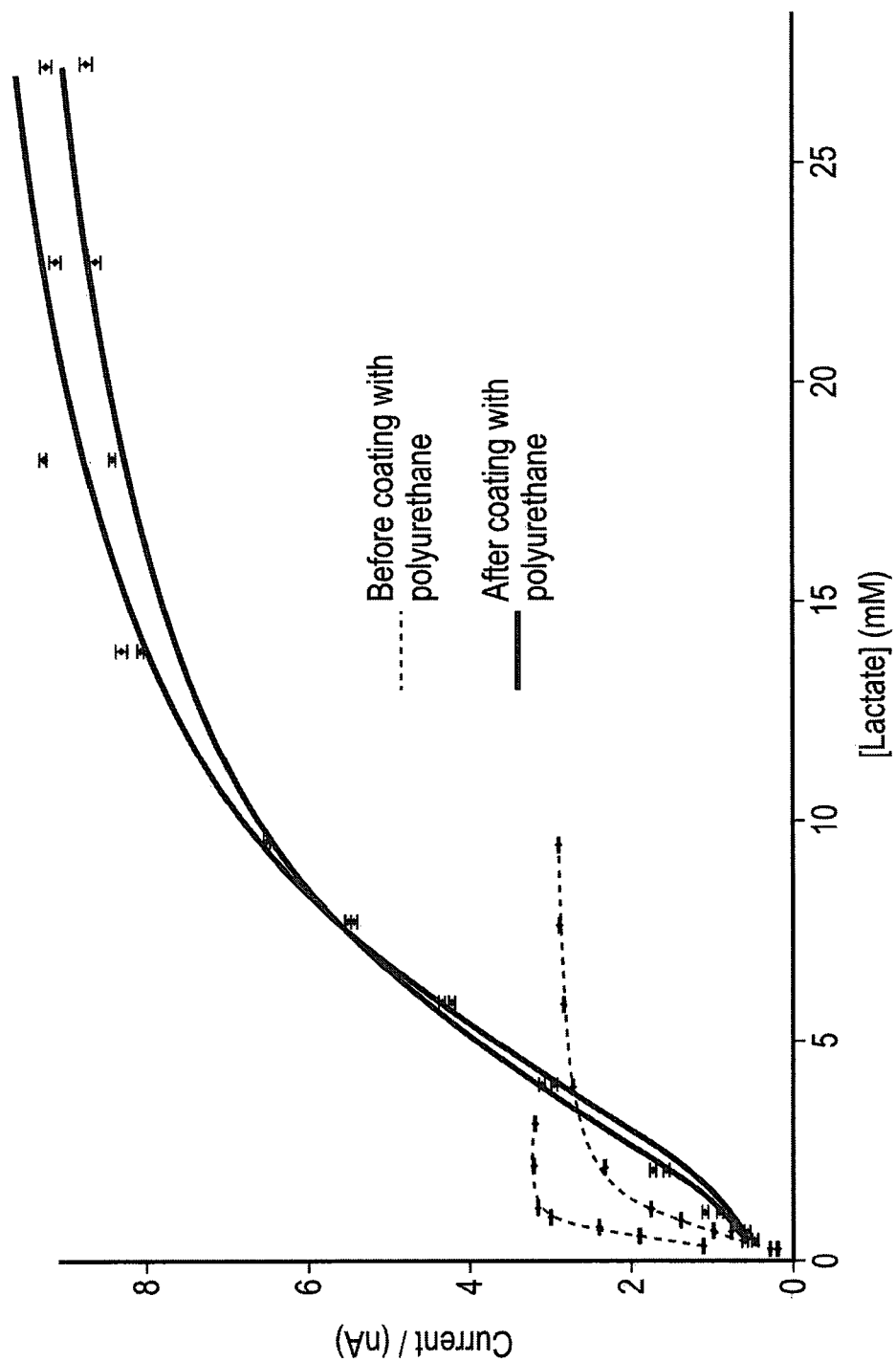

FIG. 22: Lactate biosensor calibration before (dotted lines) and after (solid lines) coating with polyurethane. Before coating the two sensors have different Km values and after coating the sensors are clearly mass transport limited, with an extended dynamic range. Furthermore, both sensors now have higher V max values. Clearly, a higher Vmax here cannot be better enzyme loading but is a direct result of the surprising interaction between the two layers.

Figure 23:
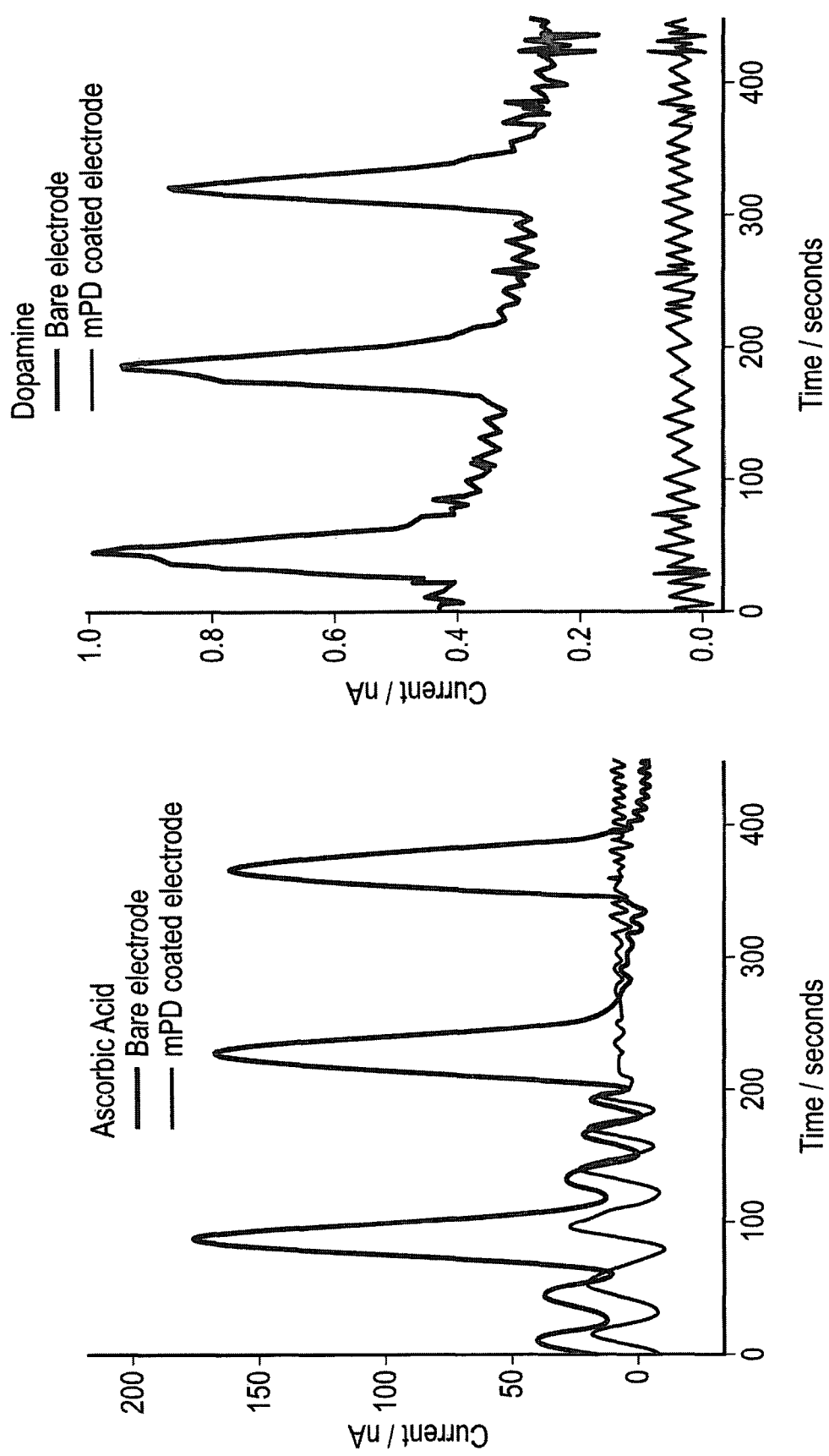

FIG. 23: Flow injection analysis of a 20 second pulse of 1 mM ascorbic acid (left hand graph) and 10 µM dopamine (right hand graph). Results from both a bare electrode and an mPD-coated electrode are shown. The bare electrode shows injection peaks for both interferents, whereas the mPD-coated electrode does not.

Figure 24:
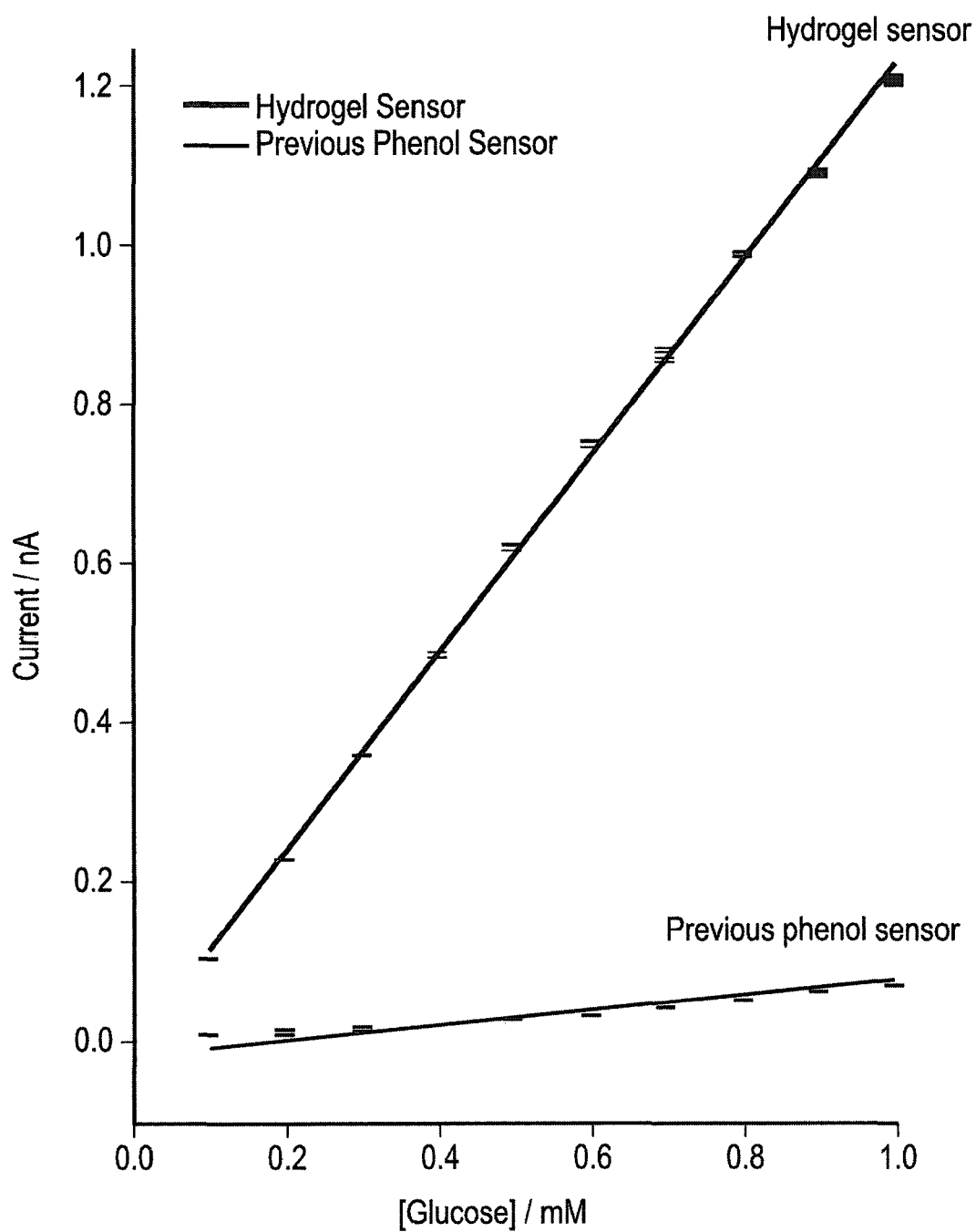

FIG. 24: Calibration of a glucose sensor in the physiological range. The sensors were held at a constant 0.7V vs Ag|AgCl reference in PBS solution, pH7.4. Aliquots of glucose were added to the stirred beaker at set time intervals using a Gilson pipette. In blue, a typical response from our previously used poly(phenol) sensors and in red, a typical response from the current hydrogel sensors is shown.

Figure 25:
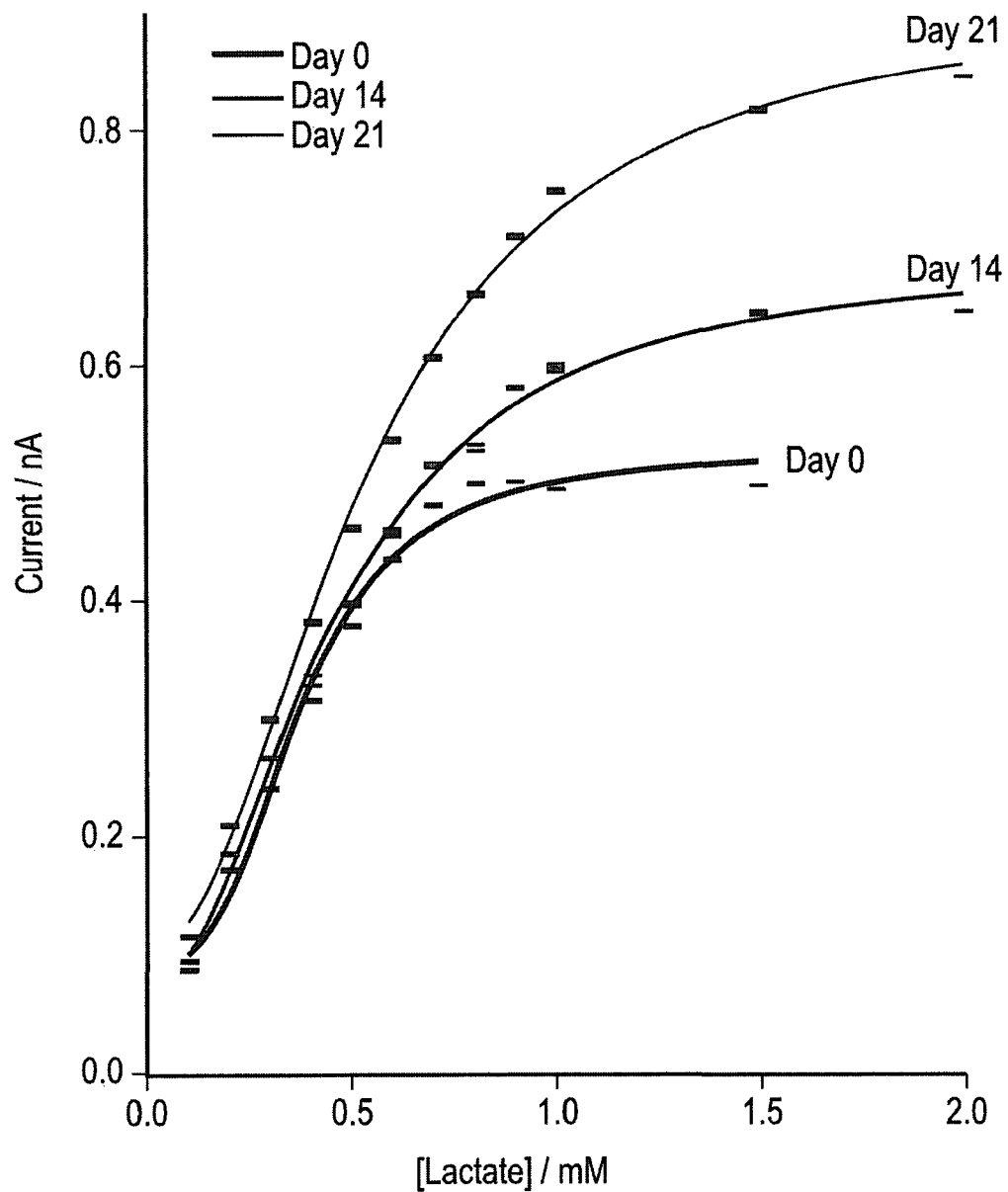

FIG. 25: Multiple calibrations of a lactate sensor in the physiological range. The sensors were held at a constant 0.7V vs. Ag|AgCl reference in PBS solution, pH7.4. Aliquots of lactate were added to the stirred beaker at set time intervals using a Gilson pipette. The sensor was tested on the day of fabrication (Day0) and stored in the freezer at −20 degrees Celsius. 2 weeks later and 3 weeks the calibration was repeated.

Figure 26:
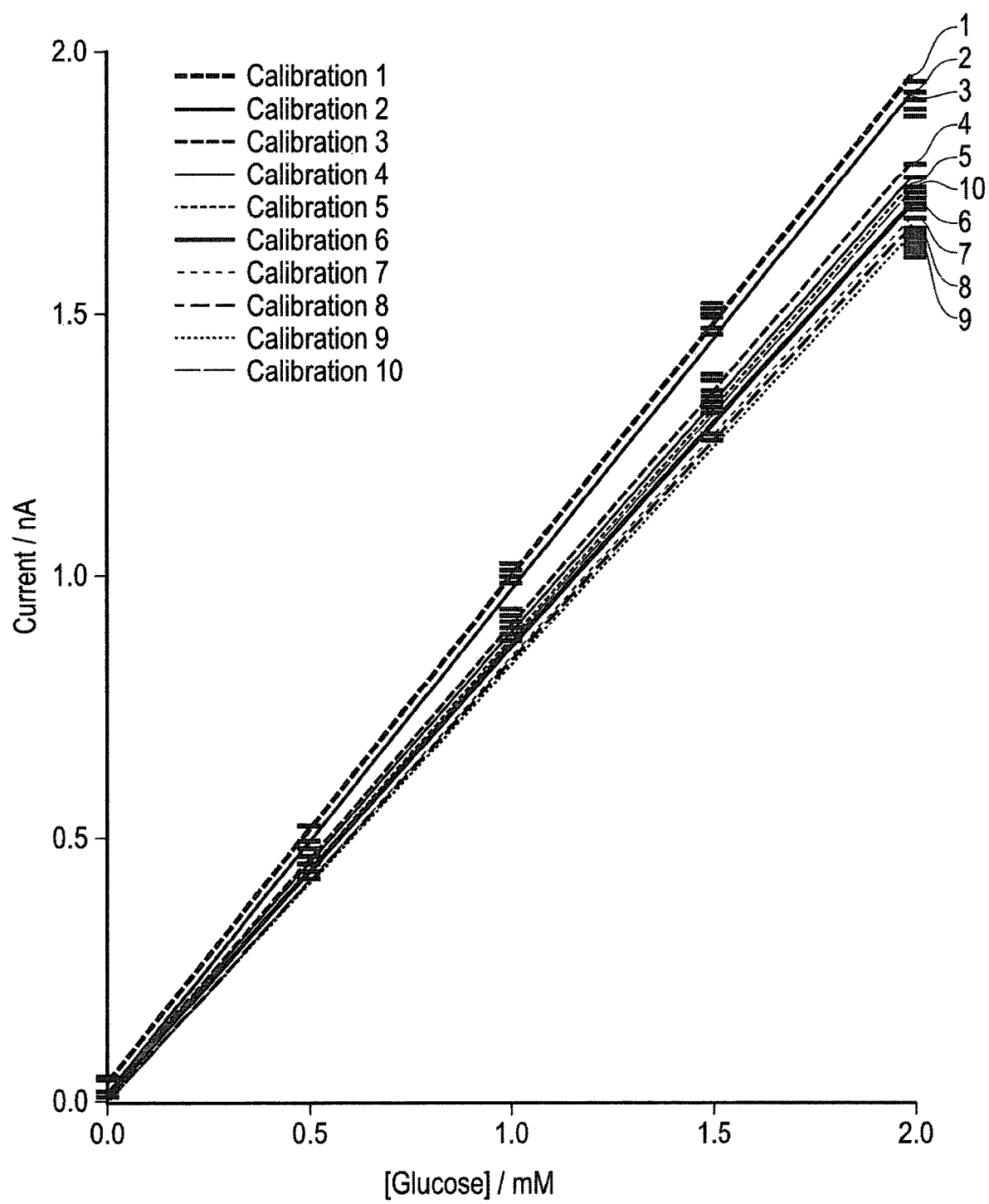

FIG. 26: Online calibrations of a glucose sensor in the physiological range using the microfluidic platform. The sensors were held at a constant 0.7V vs Ag|AgCl reference in a 0.1 mM glucose ad PBS solution, pH7.4, perfusing the microfluidic circuit at a constant 2 µL/min flow rate. After 1 hour, the system ran a 5-point calibration from PBS (0 mM glucose) to 2 mM glucose. This sequence was then repeated 10 times, resulting in 12.5 hours of constant use. All 10 calibrations are shown.

Figure 27:
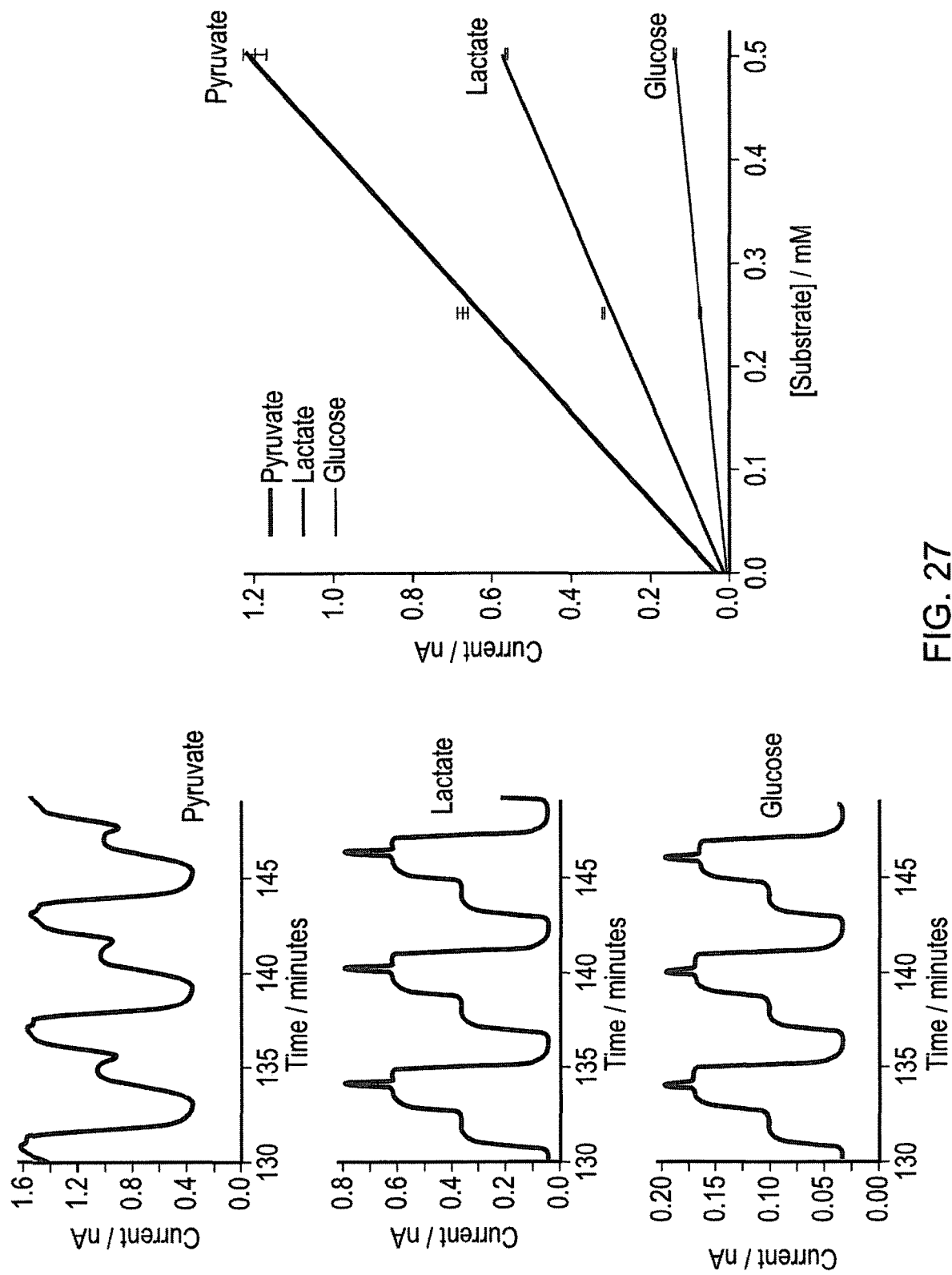

FIG. 27: Online simultaneous analysis of pyruvate, lactate and glucose using the microfluidic circuit board. The microfluidic circuit was used to vary the concentration of the three substrates from PBS (0 mM) to 0.5 mM to create a three-point calibration curve. The raw data is shown on the left, with pyruvate in blue, lactate in green and glucose in red. On the left, is the typical calibration curve for these three sensors.

FIG. 28:

C) An example continuous on-line analysis of a 15 minute segment of microdialysis stream from a patient with a brain microdialysis probe using sensors in a microfludic device. This segment corresponds to a period in which there appeared to be no on-going pathology and may be considered to represent baseline levels in brain tissue that is at risk but stable. Glucose is shown in red and lactate levels are shown in green.

D) Calibration profiles of a lactate sensor in continuous use on the clinical ward. Calibration standards were perfused passed the sensor at set time points using the automated calibration system and calibrations were typically conducted 3 hours apart. The auto calibration system copes with an unusual pattern of falling and rising sensitivity of the system possibly due to the presence of air bubbles disturbing flow though the chip. It is more common to see a gradual fall in sensitivity as shown in FIG. 26.

E) An example continuous on-line analysis of a 45 minute segment of microdialysis stream from a patient with a brain microdialysis probe using sensors in a microfludic device. This segment corresponds to a period in which dynamic events called spreading depolarisations were seen in electrical contacts in the brain adjacent to the microdialysis probe used to detect the electrical state of the brain. The neurochemical effects of these dynamic events i were recorded from an online glucose (red, middle trace) and lactate (green, bottom trace) sensor placed in a microfludic device. The lactate/glucose ratio is shown in the blue, top trace. Time zero has been assessed from the start of the dynamic event as recorded at the electrical contacts. There is a spontaneous repeat of this event, 17 minutes later, as indicated by the grey dotted lines. Glucose levels transiently fall, lactate levels and the LG ratio transiently rise.

The listing or discussion of an apparently prior-published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention.

EXAMPLES

Example 1—Electrode Fabrication

The biosensors used in this work are based on combined needle electrodes.[19,35] Briefly, a 50 µm diameter polytetrafluoroethylene (PTFE) insulated platinum/iridium (90%: 10%) wire (Advent Research Materials, UK) and a 50 µm polyester insulated silver wire were threaded through a 27 G hypodermic needle. The insulation layer was removed from the ends of the wires using a small flame, to expose the metal. The ends of the two wires were each connected to an electrical wire using conductive silver epoxy glue (RS Components, UK). Epoxy resin (Robnor resins, CY1301 and HY1300) was used to fill the needle and to secure the wires in place. Once the epoxy resin was cured, the sharp tip of the needle was abraded using sandpaper (Buehler, UK), to just above the bevel of the needle, to create silver and platinum disc electrodes. The blunt needle was then polished sequentially with alumina slurries (1, 0.3, and 0.05 µm). Finally, in order to create the Ag|AgCl reference electrode, the tip of the needle was dipped into a potassium dichromate reference solution (BASi, US) for 3 seconds, and then into a solution of diluted 37% hydrochloric acid for 20 seconds, to remove the oxide layer from the working and auxiliary electrodes. Cyclic voltammetry was used to assess the working electrode surface.

Example 2—Biosensor Fabrication

All biosensors were controlled using in-house potentiostats and a PowerLab 8/35, controlled by LabChart Pro (ADInstruments). Glucose and lactate biosensors were fabricated in several layers, as shown in FIG. 14-B. Layer i: The working electrode was first coated with poly-m-phenylenediamine (m-PD) using electropolymerization, to screen out potential interferences. Briefly, the combined needle electrode was placed in a 100 mM solution of m-phenylenediamine in 0.01M PBS at pH 7.4. The potential was held at 0 V for 20 s, 0.7 V for 20 min for electropolymerization to occur and then 0 V for 5 min. The electrode was gently rinsed with deionised water and cyclic voltammetry was used to verify that the working electrode had been successfully coated. Layer ii: After successful electropolymerization of the screening layer, the electrodes were dipped into the enzyme solution (60 mg/ml lactate oxidase (Lox—for example from *Aerococcus viridians*, for example purchased from Sekisui Diagnostics) or glucose oxidase (GOx, for example from *Aspergillus niger*, for example purchased from Sekisui Diagnostics) 30 mg/ml bovine serum albumin, 60 mg/ml poly(ethylene glycol) diglycidyl ether and 2% v/v glycerol in 0.01 M PBS, adapted from the method described by Vasylieva et al.[36,37]). The needles were placed in an oven at 55° C. for 2 hours. Layer iii: Following enzyme immobilisation, biosensors were also coated with a polyurethane film (Texin 985, for example from Bayer), in order to extend their dynamic range to include the higher lactate levels possible in exercising tissue and to protect against any flow variations, which could occur in a flow-cell, affecting mass transport conditions.

Example 3—Fabrication of Microfluidic Platform

The below describes only one method of making the claims microfluidic device. Other methods include soft lithography which is described in further examples.

Two different 3D printers were used for printing of the microfluidic platform. The microfluidic chip was fabricated using a 3D printer ULTRA® 3SP™. This machine provides 100 µm resolution in X and Y-axis and between 25-100 µm resolution in the Z-axis, depending on the parameters set. However, the true resolution of the printer is given by the voxel dimension and the material employed during fabrication. Throughout the development of this work, the 'ABS 3SP™ White' resist was used for printing of the microfluidic chip. ABS 3SP™ White allows printing of dimensionally and mechanically stable components, although due to shrinkage of the resist in the printing process smaller dimensions than those specified in the design of the microfluidic channel were observed. In general, a tolerance of about 100 µm needs to be considered during the design of the components. The microfluidic platform was designed with an L-shape, in which the inner microfluidic channel incorporates a 90° bend. As the microfluidic chip needs to integrate two separate needle biosensors, one for glucose and the other for lactate sensing, it was decided to insert the two needles into the microfluidic channel through two round openings printed on the top wall of the microchannel. This configuration ensures a tidy and compact packaging of the overall platform, as shown in FIG. 14-j. However, it limits the minimum microchannel width that is achievable, as it has to fit the 27 G needle (0=ca. 413 µm) biosensors. Three different sizes of microfluidic channels were printed and tested, which had different height and width dimensions, these were: (1) 520×520 µm, (2) 750×550 µm and (3) 1000×550 µm. Moreover, taking into account the material shrinkage, for channel (1) two slightly wider microfluidic chambers were designed at the two needle biosensor insertion locations to avoid issues during placement of the biosensors.

Printing of the needle holders was performed using the Objet260 Connex™ 3D printer. The main advantage of using this printer compared to the ULTRA® 3SP™ is the possibility to print rigid and soft material simultaneously on the same component. For instance, VeroWhitePlus (RGD835) and TangoBlack (FLX973) were employed for the printing of the rigid and soft parts, respectively. To fix the position of the needle biosensor inside the holder two grub screws M2.5 were also used. The rubbery part of the holder has a truncated cone shape to guarantee fluidic sealing and to avoid incorrect positioning of the biosensors inside the microfluidic channel. In fact, initial attempts using a cylindrical shape rubber part lead to incorrect mounting of the biosensor holder into the microfluidic chip due to XY expansion of the rubber when compressed.

Example 4—Calibration & Characterisation Studies

Glucose and lactate biosensors were both held at a constant potential of +0.7 V vs Ag|AgCl. The biosensors were calibrated inside the microfluidic chip using a calibration board, consisting of two LabSmith 20 μl programmable syringe pumps, one containing T1 perfusion solution and one containing a glucose/lactate standard. By mixing the flows, a multi-point calibration was carried out by varying the relative flow rates of the two pumps, while keeping the overall flow rate constant at 1 μl/min. This system was also used to measure the time response of the biosensors in the microfluidic chip, by switching between the two solutions and measuring the time taken for the sensors to reach a steady current. In vitro microdialysis experiments were conducted using an expired microdialysis probe (CMA70, MDialysis, 10 mm membrane length, 20 kDa molecular-weight cut-off), perfused with T1 solution (2.3 mM calcium chloride, 147 mM sodium chloride and 4 mM potassium chloride) at 1 μl/min using a microdialysis pump (CMA107, MDialysis).

Example 5—3D Printed Microfluidic Device

The design of the 3D printed microfluidic device was driven by the need to make a reliable and simple connection between the microfluidic chip and the commercially available microdialysis probe through the use of the probe outlet holder (FIG. 14-C item c). This simplifies the overall device architecture, as no extra connection tubing and adaptors are needed, additionally decreasing the overall dead volume of the system.

The design of the microfluidic device was inspired by the configuration used in the standard microdialysis set-up (FIG. 14-A), in which the microfluidic device slots into the probe outlet holder and replaces the microvial, as shown in FIG. 14-D. To achieve this, the microfluidic chip (FIG. 14-C item e) was designed and printed with a unique L-shape, the vertical arm for connection purpose and the horizontal arm for integration of the two needle biosensors. The vertical arm of the chip presents similar geometry to the microvial. For instance, the microfluidic inlet port was printed to incorporate the rubber insert (FIG. 14-C item d) from the microvial, so as to take advantage of the easy and leak-free connection port. Moreover, this design offers flexibility for the device to be used in a diverse range of microdialysis applications, as it can be used with all clinical microdialysis probes, since they have the same type of outlet holder.

With regard to the horizontal section of the microfluidic device, a major challenge was to incorporate and secure the biosensors in the correct position inside the microfluidic channel, preventing any leaks. Initially, attempts were made to achieve this by threading the needle electrode through a commercially available 1/32" one-piece fitting (2-56 UNC) and using this to secure the electrode in place inside the microfluidic chip.[29] Using this approach, the device dimensions were determined by the size of the fittings, and as such were relatively large (over 1 mm). However, integrating the biosensor in this way did not provide a good seal with the microfluidic chip, causing leaks to occur. Erkal et al. showed that electrodes could be successfully integrated with 3D printed microfluidics using commercially available fittings, however, due to the small size of our sensor, a 1/32" fitting was required. These threads were too small (2-56 UNC) to be printed and a thread taper (M2.5) was used instead. Unfortunately this approach did not provide a satisfactory seal, or good reproducibility. To overcome the issue of the previous method, custom-made electrode holders (FIG. 14-C parts g and h) were also designed and 3D printed, which allow better control over the electrode placement inside the microfluidic channel.

With regard to the horizontal section of the microfluidic device, a major challenge was to incorporate and secure the biosensors in the correct position inside the microfluidic channel, preventing any leaks. Initially, attempts were made to achieve this by threading the needle electrode through a commercially available 1/32" one-piece fitting (2-56 UNC) and using this to secure the electrode in place Inside the microfluidic chip.[29] Using this approach, the device dimensions were determined by the size of the fittings, and as such were relatively large (over 1 mm). However, integrating the biosensor in this way did not provide a good seal with the microfluidic chip, causing leaks to occur. Erkal et al. showed that electrodes could be successfully integrated with 3D printed microfluidics using commercially available fittings, however, due to the small size of our sensor, a 1/32" fitting was required. These threads were too small (2-56 UNC) to be printed and a thread taper (M2.5) was used instead. Unfortunately this approach did not provide a satisfactory seal, or good reproducibility. To overcome the issue of the previous method, custom-made electrode holders (FIG. 14-C parts g and h) were also designed and 3D printed, which allow better control over the electrode placement inside the microfluidic channel.

The electrode holder was printed using the Objet260 Connex™ 3D printer, capable of printing both hard and soft plastics simultaneously on the same component. This enabled the bottom part of the holder to be printed using a soft and compressible plastic, ensuring a good seal between the holder and the microfluidic device, preventing potential leaks. The holders were designed so that the needle tip protruded from the end and the needle was secured in place using two grub screws. The needle position inside the holder could be varied depending on the length of the needle, as this can change after repeated polishing of the electrode.

This ensures that the needle tip was at a fixed distance from the end of the holder and hence in the correct position inside the microfluidic channel. The microfluidic platform was designed so that the holder could be guided into position; two pegs on the sides of the electrode holder inserted into guiding slots and locked into place, positioning the needle tip precisely inside the channel (see supporting video 2). Moreover, to facilitate the positioning of the electrode inside the microchannel an additional cross-sectional cut-out of the microfluidic device was printed. Using the cut-out component it was possible to visualise the electrode inside the channel under a microscope and to precisely secure the sensors inside the holders so that the tip of the biosensor was at the desired height inside the microchannel.

The use of 3D printing for fabrication of the device enabled a modular approach to be adopted, designing separate parts to be integrated together. Using this method each part of the device could be designed and optimised iteratively to meet its own individual requirements.

Example 6—Biosensor Characterisation Inside 3D Printed Microfluidic Chip

To investigate the effect of the microfluidic channel dimensions on the response time of the sensors, three different channel sizes were tested, as described in the experimental section. FIG. 15 shows the normalised current response of a glucose biosensor to a step change from 0 to 2 mM at 1 μl/min for the different channel sizes. In each case the sensor was positioned in the middle of the channel. Cross-sections of each channel were measured using a microscope to determine the actual dimensions of each of the channels. The dimensions specified in the table in FIG. 15 refer to the measured dimensions.

Laminar flow inside the connection tubing and microfluidic channel leads to broadening of the concentration change, due to Taylor dispersion, as shown in FIG. 15B.[27] This demonstrates that the time response of the sensor to a step change is reduced by decreasing the channel size. The fastest response time was observed in channel 1, therefore, these dimensions were chosen for the final device. For comparison, FIG. 15-A shows the corresponding response of an extended-range lactate biosensor in a well-stirred beaker (mean T90 response 32.3±2.2 s). The sensor responses in the three different channel sizes are summarized in table 1.

TABLE 1

Effect of channel size on response time

| Channel dimensions H × W (µm) | Glucose $T_{90}$ (s) | Lactate $T_{90}$ (s) |
|---|---|---|
| 375 × 508 | 208 ± 6.5 | 194 ± 15 |
| 410 × 615 | 267 ± 7.7 | 227 ± 7.0 |
| 421 × 971 | 398 ± 12.8 | 286 ± 6.9 |

The horizontal section of the microfluidic chip is similar to the microfluidic device described by Erkal et al., which had an internal volume of 3.90 µl. Our microfluidic chip is broadly similar but the internal volume up until the first biosensor is approximately 1.91 µl based on measured dimensions.

Metabolite levels in tissue vary between people, and depend on a person's metabolism and fitness during exercise, as well as on the particular tissue being sampled.[39] The system was calibrated online from 0 to 10 mM, at 1 µl/min to verify that it is capable of detecting physiologically relevant concentrations of glucose and lactate levels in the dialysate. FIG. 16 shows typical current response vs. concentration for the biosensors when placed in the microfluidic device. These data indicate that the biosensing system has good sensitivity to glucose and lactate, with clear current changes corresponding to increasing levels of substrate. The biosensors show a good dynamic range, suitable for physiological monitoring. The fact that sensitivities are similar for the glucose and lactate sensors (FIG. 16) reflects the mass-transport limiting effects of the polyurethane membrane.

As a further validation test, it was important to test the microfluidic device with a microdialysis probe in vitro. To mimic changes occurring in the tissue, the microdialysis probe was placed in a well-stirred beaker, and subjected to changes in beaker lactate and glucose concentrations. The outlet holder of the microdialysis probe was connected to the microfluidic device, which continuously measured the glucose and lactate levels of the dialysate.

As the biosensors are placed consecutively in the microfluidic chip, there is a 2-minute delay between the lactate and glucose responses to the dialysate changes. There is also an additional delay to take into account, between the changes occurring at the probe membrane and the analysis system, due to the length of outlet tubing. Taking both factors into consideration, the total delay was found to be 13 minutes for the lactate biosensor, which was placed first in the direction of flow and 15 minutes for the glucose biosensor, which was placed second in the direction of flow. This delay is largely caused by the commercially available probe outlet tubing and, therefore, could be reduced further still if the extension on the probe outlet was shortened.

Nevertheless, the delay time of the microfluidic device described here was substantially improved compared to our PDMS-based microfluidic device, which had a lag time of 25 minutes using the same flow rate (1 µl/min).

Example 7—On Line Monitoring of Brain Glucose, Lactate and Glucose/Lactate Ratio in a Patient Using a Microdialysis Probe Placed in Perilesional Cortex In an ongoing proof of concept study to monitor the brain of traumatic brain injury patients, subarachnoid haemorrhage patients and malignant haemorrhagic stroke patients while there are in the intensive care unit, microfluidic device containing sensors for glucose and lactate was tested for periods of up to 120 h of continuous monitoring. Typically monitoring was for 48-72 hours.

A microdialysis probe was placed in at risk cortical tissue during a surgical operation carried out to address other clinical needs. Towards the completion of surgery, a sterile clinical microdialysis catheter (CMA 70, 60-cm flexible shaft, 10-mm membrane length, 20 kDa cutoff, M Dialysis, Stockholm, Sweden) was inserted obliquely into the cortex, to full membrane depth through a minimal pial incision. Along with the microdialysis catheter, a linear, six-platinum-contact electrocorticography (ECoG) recording strip (Wyler, 5 mm diameter contacts; Ad-Tech Medical, Racine, Wis., USA) was placed on the surface of the cortex accessible through the craniotomy. The aim was to locate the ECoG strip and microdialysis catheter closely together; it was usually possible to site them on the same gyrus, the microdialysis probe sited in penumbral cortical tissue between contacts of the EcoG strip that was radiating away from the lesioned area. After surgery, the patient was transferred to intensive care.

The microdialysis catheter was perfused with sterile artificial cerebro-spinal fluid (CMA perfusion fluid CNS: 147 mM NaCl, 2.7 mM KCl, 1.2 mM CaCl2, 0.85 mM MgCl2) at 2 µL/min using a CMA 100 Microinjection syringe pump (M Dialysis, Stockholm, Sweden). In classical microdialysis where hourly samples are taken a flow rate of 0.3 µL/min is used to monitor the human brain. For a 10 mm membrane length this equates to a mean relative recovery of approximately 65 to 72%. At faster flow rates such as those used in this work, recovery declines; at 1 µL/min recovery is between 21 and 34% for the same molecules. (Hutchinson P J, O'Connell M T, Al-Rawi P G, Maskell L B, Kett-White R, Gupta A K, et al. Clinical cerebral microdialysis: a methodological study. J Neurosurg 2000; 93: 37-43; Bellander B-M, Cantais E, Enblad P et al (2004) Consensus meeting on microdialysis in neurointensive care. Intensive Care Med 30:2166-2169. doi: 10.1007/s00134-004-2461-8)

Perfusion of the MD catheter started immediately after the end of the operation so that the blood brain barrier was sealed and the initial baseline dialysate levels were steady when the online measurements started in the intensive care unit (typically a few hours following surgery). The outlet tubing of the probe was adapted to connect to a continuous online analysis system. Typically, a one-meter length of low volume connection tubing was used between the patient and the online assay to facilitate patient movement and nurse care. The dialysate concentration time series were time-aligned with the ECoG data trace corresponding to the closest electrode on the strip, to take account of the 9 minutes delay due to the one-meter length low volume connection tubing between the patient and the analysis system. The auto calibration system was set to perform calibrations for glucose and lactate every 3 h. The microfluidic chip was made using soft lithography.

Results

Figure 28C:
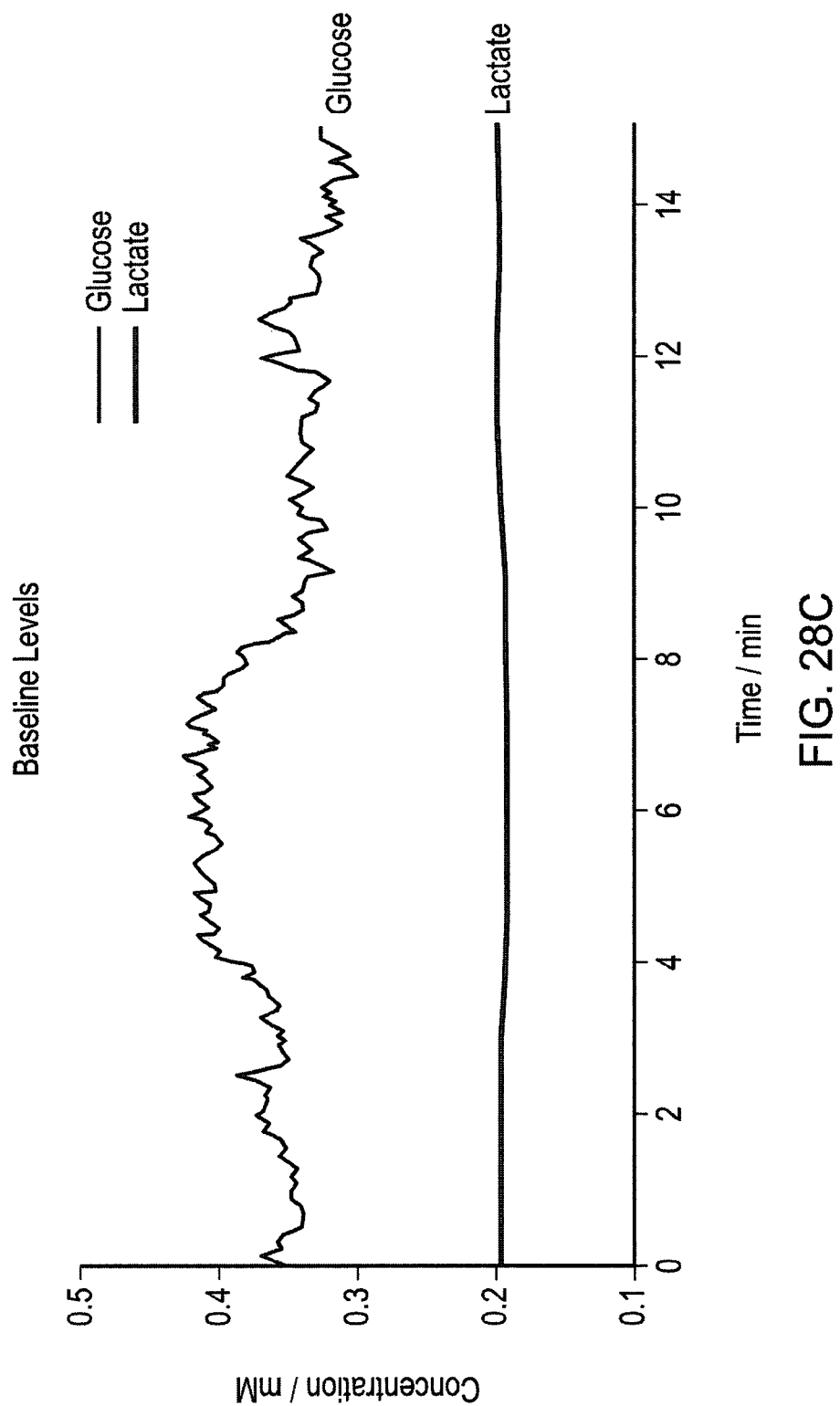
Figure 28D:
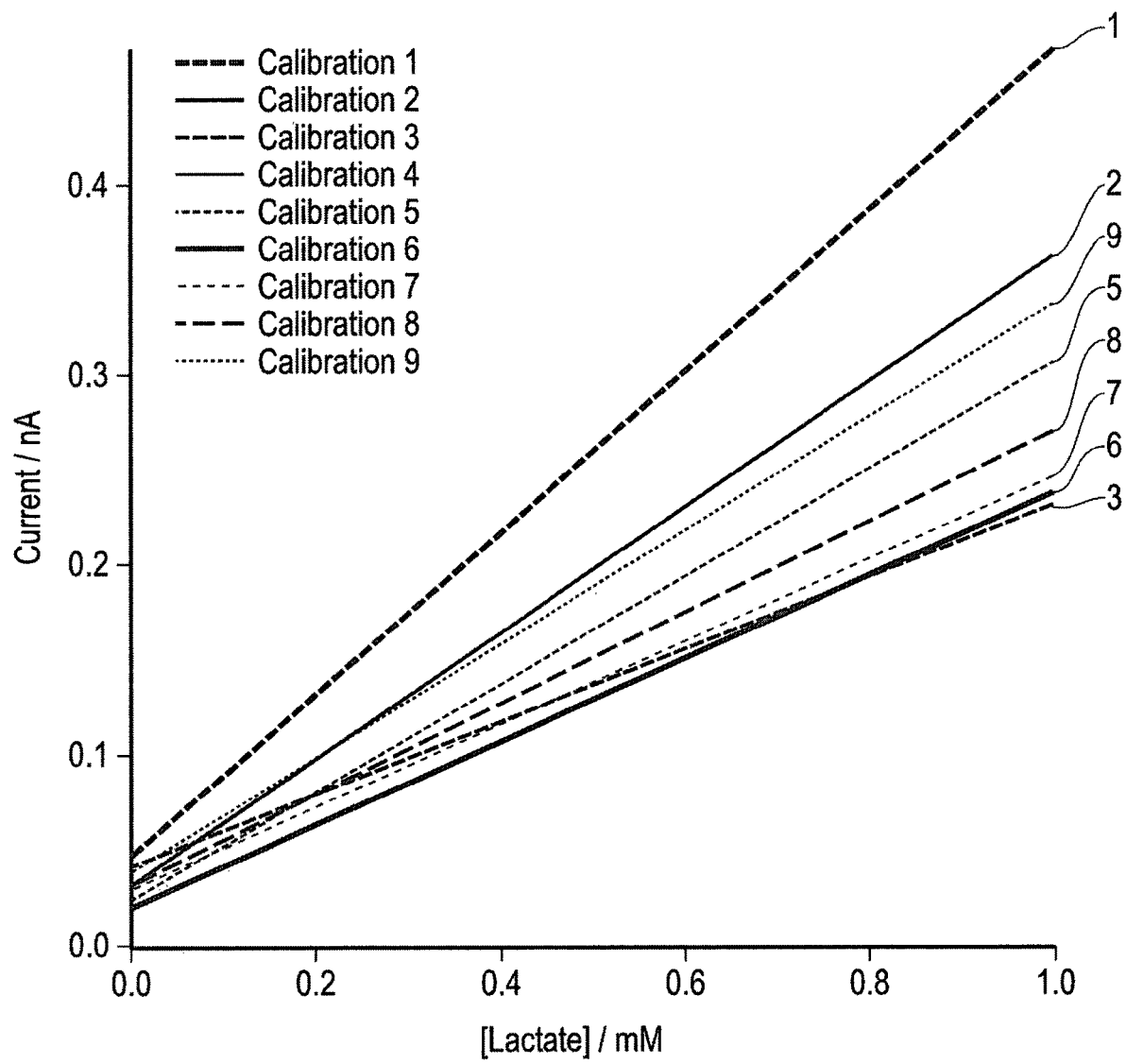

The data in FIG. 28 C shows a 15 minute period of the continuously analysed data from the brain microdialysis stream. In this patient the tissue is not undergoing any apparent on-going pathology and may be considered to represent baseline levels for this local area of brain tissue that is at risk but stable.

Brain glucose levels at 300-400 µM are typical for such tissue, and above recently agreed critical thresholds for action for brain glucose (CONSENSUS DOCUMENT 2015) once the difference on flow rates in taken into account. Lactate levels at 200 µM are low and well below critical threshold for clinical intervention. The Lactate to glucose ratio is between 0.5 and 0.6, a value we would consider as indicative of stable tissue.

FIG. 28 shows the results of auto calibration or the patient monitoring system carried out over a twenty four hour monitoring period at 3 hour intervals. The data plots the sensor amperometric current against lactate concentrations for the lactate sensor, and indicates initially an unexpectedly rapid fall in sensitivity followed by a recovery. This unusual pattern may well be explained by the presence of air bubbles disturbing flow through the microfludic device. More commonly a slow decline in sensitivity is found such as is shown in FIG. 26. This ability to cope with unexpected changes in sensor sensitivity is a strength of the auto calibration system.

Figure 28E:
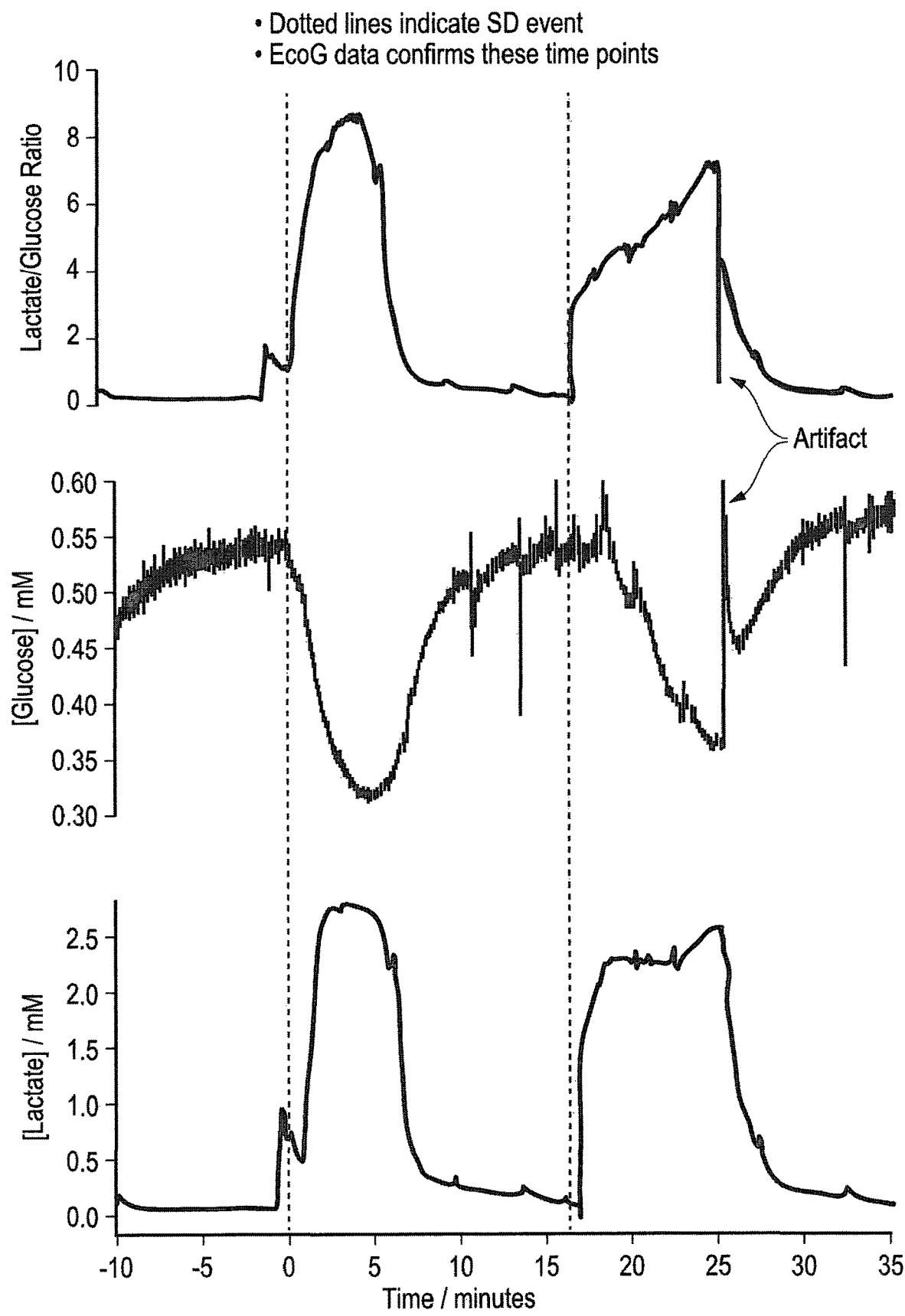

In FIG. 28 E data is shown from a period when the brain tissue is undergoing dynamic pathological events called spreading depolarisations (SDs). SDs are mass electrical depolarisations that move though injured at risk brain tissue, and are associated with poor patient outcomes (Fabricius M, Fuhr S, Bhatia R, Boutelle M, Hashemi P, Strong A J, Lauritzen M. 2006. Cortical spreading depression and peri-infarct depolarization in acutely injured human cerebral cortex. *Brain* 129: 778-90, leading to dynamic changes in brain glucose and lactate; and Hartings J A, Bullock M R, Okonkwo D O, Murray L S, Murray G D, Fabricius M, Maas A I R, Woitzik J, Sakowitz O, Mathern B, Roozenbeek B, Lingsma H, Dreier J P, Puccio A M, Shutter L A, Pahl C, Strong A J. 2011. Spreading depolarisations and outcome after traumatic brain injury: a prospective observational study. *The Lancet Neurology* 10: 1058-64). We have previously shown using rapid sampling microdialysis that these are associated with changes in glucose and lactate (Feuerstein D, Manning A, Hashemi P, Bhatia R, Fabricius M, Tolias C, Pahl C, Ervine M, Strong A J, Boutelle M G. 2010. Dynamic metabolic response to multiple spreading depolarizations in patients with acute brain injury: an online microdialysis study. *J Cereb Blood Flow Metab* 30: 1343-55), but were unable in patients to define the time courses of these changes. We see in FIG. 28E that initially brain glucose levels at 500 µM and brain lactate levels at 60 µM are safely inside critical thresholds. The Lactate/glucose ratio at 0.1 is healthily low. At time zero an SD event is detected at the electrocorticography electrode placed above the microdialysis probe. In the figure we see the neurochemical consequences of the SD for the brain levels of energy metabolites glucose and lacate. There is a dynamic fall in glucose to about 300 µM indicating an insufficiency of glucose supply compared to brain tissue use. For lactate there is a dramatic increase in brain lactate to >2.7 mM. This is transiently above the critical threshold for lactate levels (taking into account the microdialysis flow rates used).

The lactate to glucose ratio also shows a dramatic dynamic increase to 8.5 a value which we would consider to indicative of tissue facing metabolic crisis. The SD repeats spontaneously 17 min later and similar changes in glucose and lactate are seen. That such dynamic neurochemical changes which cross critical threasholds can be resolved is a great advantage of the on-line analysis system using sensors in a microfluidic device as an average of the data shown into an 1 hourly classical microdialysis sample would not cross the critical threshold.

Example 8—Determination of Optimal Concentrations of Co-Factors for Sensing Reagent The below was carried out using the microfluidic system described herein. This provides an example of the general flexibility of the autocalibration system.

Each enzyme has an optimal concentration of co-factors required for activity, dependent on various factors such as enzyme and substrate concentration. In the optimisation reaction the concentration of both the enzyme, pyruvate oxidase, and the substrate, pyruvate, was kept constant (30 mg/ml and 0.5 mM respectively) and individually the concentration of each cofactor ($Mg^{2+}$ and TPP) was varied. The response to increasing the concentration of each cofactor is shown (FIG. 18). Thus, the optimised levels of each were 21 mM $Mg^{2+}$ and 6 mM TPP.

In a separate experiment, the mixture was varied to contain the cofactors individually or both together for a direct comparison of signal output.

Example 9—Characterisation of Sensor and Electrode Layers

The electrode was constructed in house. Briefly, a 50 mm Teflon insulated platinum wire (A-M Systems Inc., US) and 50 mm polyester insulated silver wire (AM systems) were threaded through a metal shaft, ideally a 27 G hypodermic needle. The wires were stripped of their insulator at each end using a lighter to expose the metal wire. Electrical wire was glued to the exposed metal at one end using conductive silver epoxy glue (RS Components). Epoxy resin (Robnor resins, CY1301 and HY1300) was used to fill the internal volume of the metal shaft and secure the wires in place. Once the epoxy had cured, the tip of the metal shaft was polished first using Wet&Dry paper (3 grades) and then using alumina slurries 1 µm, 0.3 µm, and finishing with 0.05 µm, with use of an ultrasound sonicator bath between each slurry for 30 seconds. The silver disc was chloridised by placing in Referencing Solution (BAS) for 5 seconds, to create Ag|AgCl reference electrode, potassium dichromate reference solution (BASi, US) for 3 seconds, washed with deionized water, and then placed into a solution of diluted 37% hydrochloric acid for 20 seconds, to remove the oxide layer from the working and auxiliary electrodes, and finally rinsing thoroughly with de-ionised water. The platinum wire is used as the working electrode and the metal shaft is used as an auxiliary electrode. Cyclic voltammetry was used to assess the surface of the electrode prior to use. All biosensors were controlled by a lab built potentiostat feeding into a Powerlab 16/35 running LabChart Pro (AD Instruments).

Layer 1

The combined electrode was placed in a solution containing 100 mM m-phenylenediamine (mPD) in phosphate buffer saline (PBS), pH 7.4. Under potentiostatic control, the working electrode was held at 0 V for 20 s, polarised to 0.7 V for 20 minutes for electropolymerisation and then held at 0 V for 20 s. The electrode was gently rinsed with de-ionised water and stored dry at 4° C. before use. The coverage of the film can be assessed through cyclic voltammetry in a solution containing 1.5 mM ferrocene monocarboxylic acid (FIG. 19).

Layer 2

To entrap the enzyme to the surface of the electrode, a hydrogel film was used. The electrode was dipped in a solution containing 60 mg/ml substrate oxidase (glucose oxidase for glucose, lactate oxidase for lactate, pyruvate oxidase for pyruvate), 30 mg/ml bovine serum albumin, 60 mg/ml PEG-DE and 2% glycerol in PBS pH 7.4. The film is applied only to the tip and not the sides of the needle shaft by using a micromanipulator to move the electrode tip towards a drop of solution on a glass slide underneath. Electrostatic forces will cause the solution to jump towards the tip, coating only the bottom plane. The electrode is left in this position for 1 minute (currently being tested for optimal length of time) before being turned upside down and left to dry in the oven at 55 degrees Celsius for 2 hours. Turning the electrode upside down produces a thinner film that allows the sensor to react more quickly to its substrate. The sensor can be used directly from the oven or it can be stored at 4 degrees overnight or −20 degrees for long-term storage (up to 1 month typically).

Layer 3

A final polyurethane layer can be applied if required to extend the dynamic range of the sensor and to protect against any flow variations, which could occur within the microfluidic chip, affecting mass transport to the biosensor surface. This was achieved by dipping the needle tip into the polyurethane solution (25 mg/ml polyurethane and 0.25 µl/ml Brij 30 surfactant in tetrahydrofuran) twice for 15 s each, leaving the needle to dry upside down for 10 min in between dipping, and for 30 min after the final coating. Due to the high volatility of THF, evaporation of the polyurethane solution is fast and therefore the results from this method can be variable (FIG. 20). Whilst the sensors are clearly mass transport limited (FIG. 21) the dynamic range of the sensors is considerably extended (FIG. 22). For lactate sensors this is a necessity as physiological concentrations can be higher than the dynamic range of the hydrogel sensors.

Homogenous Addition of Sensing Reagent

Homogenous addition of the enzyme and cofactors can increase the sensitivity of the assay. For pyruvate, this effect is significant. The sensing reagent consists of 15 mg pyruvate oxidase, 21 mM MgCl, 6 mM TPP in buffered solution. This is added directly to the online sample, thorough mixing and a reaction time sufficient for exhaustion of substrate is allowed, before analysis at a downstream, mPD coated, electrode.

LabSmith pumps and valves that are set up in such a fashion to allow complete control of the movement and direction of the flow streams. The microdialysis flow rate is set to 2 µL/min and sensing reagent flow rate is typically 0.5 µL/min.

Key for use with clinical microdialysis, we have implemented a valve that allows the microdialysate to be switched to and from the analysis microfluidic chip, without disrupting or stopping the flow through the microdialysis probe itself. This is of great importance as the sampling technique of microdialysis relies upon a steady and constant flow across the semi-permeable membrane at its tip. The addition of this valve has the added ability of being able to collect the dialysate for more classical analysis.

When the dialysate has been switched away from the analysis chip, the other side of the microfluidic circuit can run. This consists of pumps, valves and reservoirs that perfuse calibration standards through to the sensors. The total flow rate here, must be the same flow rate as the microdalysate flow rate because the sensors are all flow sensitive, therefore a change in the flow rate will give a change in sensor output (current) regardless of any changes in concentration. This will lead to artefacts in the data and an inability to use the calibration curve to interpret the clinical data. Using a ratiometric approach, the microfluidic circuit allows any concentration to be delivered between 100% of solution 1 to 100% of solution 2. Once the calibration has been achieved, the valves all switch back and the dialysate is once again perfused through the analysis chip. This microfludic circuit board is set-up such that there are no air bubbles introduced (which can occur when removing connectors by hand). Air bubbles are very disruptive to electrochemical recordings as well as disruptive the flow over the sensors and through the microdialysis probe. As the calibrations are automated to occur at set time intervals, we have ensured that the data from the samples can be analysed and interpreted accurately and reliably.

Results

Figure 10:
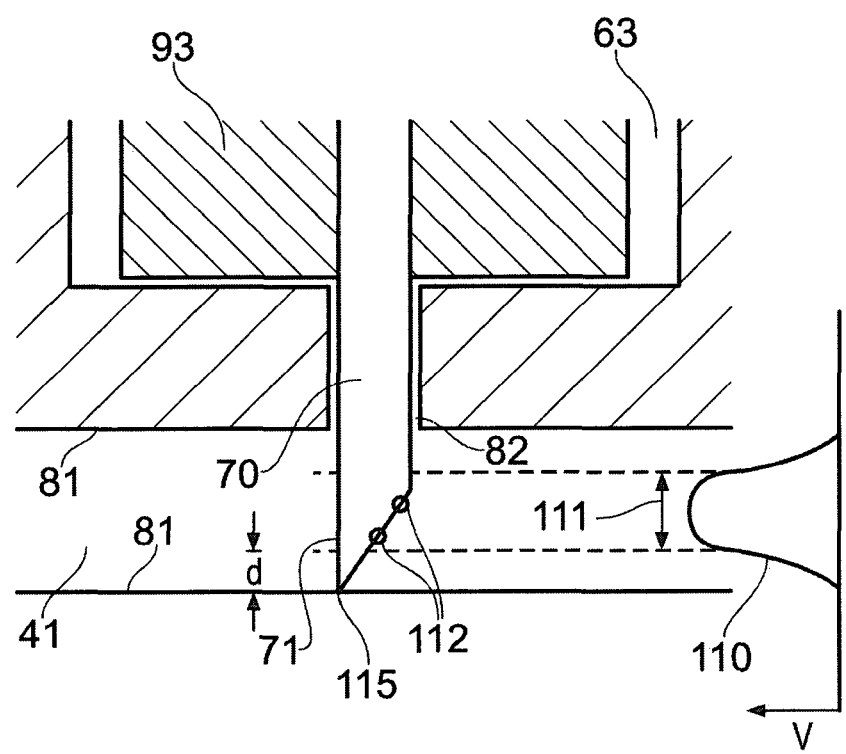
FIG. 10 is a cross-sectional view of a needle electrode extending into a flow channel of the analysis module of FIG. 6.

For selectivity measurements, flow injection analysis (FIA) was carried out, FIGS. 10 and 23. An mPD coated electrode and a bare electrode were placed in a flow cell that was connected to a quaternary HPLC pump (HP1050, Aligent), where the flow rate was set at 1 ml min-1. Pump A was used to maintain a constant flow of Krebs buffer pH 7.4. The cell was switched to pump B, which contained various interferents, for the duration of 20 s. The responses of the unmodified electrode and the coated electrode, which were both held at a constant 0.7V vs Ag|AgCl reference, were assessed for selectivity in the presence of 1 mM ascorbic acid and 10 µM dopamine (FIG. 23).

The presence of the hydrogel increases sensitivity and stability by allowing a higher loading of enzyme on to the surface, FIG. 24. Previously, the enzyme was incorporated into the interference layer, here poly(phenol) has been used. Whilst this worked with good results, the addition of the hydrogel has dramatically improved the sensor. The calibration here was conducted in a beaker with additions added using a Gilson pipette:

The hydrogel sensors can be stored at −20. Here are typical results of sensors stored in such a way, FIG. 25. The sensitivity of the sensor seems to increase with each use. We believe that this is due to the freeze-thaw action on the hydrogel film that occurs at each use. The freeze-thaw action acts to rehydrate and break up the hydrogel. After one or two repeats, the hydrogel has a more open structure allowing better diffusion through and perhaps reorientation of enzyme molecules for optimal signals. However, further freeze-thaw action will see the complete breakup of the hydrogel film and now further response is elicited from the sensor.

To test the sensor stability during constant use the sensors were placed on the microfluidic platform monitoring a continuous stream of substrate (0.1 mM glucose). After 1 hour of continuous substrate perfusion, the sensor was calibrated in an automated fashion (using the microfluidic flow system described herein) (each calibration taking 15 minutes to complete). In total, the sensor was run for 12.5 hours. Here, FIG. 26, are the calibration curves from these automated calibrations. Whilst the calibration does change over time, the sensitivity of the sensor is still very good for clinical monitoring. This highlights the importance of regular calibrations to ensure a reliable and accurate interpretation of clinical results.

The 3 types of sensors were all run on the same microfluidic circuit board simultaneously. Glucose and lactate were measured using the hydrogel sensors and homogenous addition of pyruvate sensing reagent was used to measure the level of pyruvate. The raw data is shown on the left and the relative calibration curves are shown on the right (FIG. 27).

The limit of detection, as defined by 3 times the standard deviation of the baseline, for pyruvate is 2.7 µM, for lactate is 2.1 µM and for glucose is 6.1 µM. The time to 90% response $t_{90}$, on the microfluidic platform for this set-up with these sensors (n=3) are 44.2±0.7 seconds for pyruvate, 29.2±1.4 seconds for lactate and 38±3 seconds for glucose. This time reflects the response time from the execution of the command to the autocalibration device, and so includes the dispersion taking place in the connection tubing and within the microfluidic chip. The time responses of the sensors in a beaker to injection of standards is much faster being for example for glucose 5.5 seconds and lactate 3.6 seconds.

Example 10—Online Subcutaneous Glucose and Lactate Measurement During Cycling Trials In a proof-of-concept study to demonstrate the potential of this device for continuous monitoring applications the 3D printed microfluidic chip, housing glucose and lactate needle biosensors, was tested as a wearable device for online measurement of subcutaneous metabolite levels during cycling training in two cyclists.

Following probe insertion, the microfluidic device was connected to the probe outlet holder and secured to the lower back, as shown in FIG. 17-A. The biosensors were connected to an in-house wireless potentiostat, housed inside a saddlebag attached to the bike seat. The wireless potentiostat used was relatively large (10.5×6.0×5.0 cm L×W×H) compared to the microfluidic device and is not yet small enough to be integrated into a fully wearable system. Current research within our groups is aimed at miniaturization of this device Cycling Protocol For in vivo microdialysis experiments, all procedures were approved by the local ethics committee (NRES 10/H0808/124, protocol CRO1608) and probes were inserted percutaneously by a qualified clinician. The skin was cleaned with alcohol wipes, and an anaesthetic cream (EMLA, APP Pharmaceuticals) was applied to the skin 45 minutes prior to probe insertion. An ice pack was also placed on the skin 5 minutes before probe insertion, to further numb the area. A sterile CMA63 microdialysis probe (Mdialysis, 10 mm membrane length, 20 kDa molecular-weight cut-off) was inserted subcutaneously, using the tunneling needle and introducer supplied, and secured in place with 3M™ single coated conformable incise medical tape. The probe was perfused with sterile T1 perfusion solution (MDialysis) at 1 µl/min using a microdialysis pump (CMA107, MDialysis). Prior to beginning exercise, baseline dialysate levels of glucose and lactate were measured. The cycling protocol consisted of 3 levels of increasing intensity, followed by a 1 min sprint, and finally a warm-down phase, as shown in FIG. 17-B. Dialysate glucose and lactate levels were also recorded during the recovery phase immediately after exercise.

Cycling trials were performed using a Wattbike (Wattbike, UK), that allows recording of pedal cadence (rpm) and heart rate using a wireless chest belt (Sunto™ dual chest belt). Data was despiked[38] and the time delay between the microdialysis probe and the analysis system removed. Current measurements were converted into concentration values using pre-experiment calibrations.

A schematic of the cycling protocol is shown in FIG. 17-B. Baseline glucose and lactate levels were measured in the dialysate, following probe insertion, prior to exercise. The exercise phase consisted of three levels of increasing intensity, followed by a short sprint and a period of warming down. Finally, dialysate glucose and lactate levels were monitored during the recovery period following exercise.

Initial levels after probe insertion were variable due to the trauma of insertion. Therefore, baseline levels were monitored for at least 30 minutes to allow time for the tissue to stabilise following probe insertion; typically this occurred 12 minutes after insertion.[20] Results obtained from one of the cyclists during the exercise phase of the cycling protocol are presented in FIG. 17-C, together with data recorded using the exercise bicycle, showing heart rate and rotations per minute (rpm), to quantify the exercise intensity. Initially, during phases ii and iii the heart rate signal was noisy as there was insufficient sweat to ensure good contact between the skin and wireless chest belt electrodes. Prior to starting exercise, baseline glucose and lactate levels in the dialysate were 6.02±1.08 mM and 1.81±0.33 mM respectively (mean±standard deviation over 30 second time period). Measured subcutaneous glucose levels decreased with increasing exercise intensity and local levels were driven down further still, following exercise even after 50 minutes of rest. In contrast, lactate levels increased with increasing exercise intensity, peaking immediately after the sprint, and gradually decreased once cycling had stopped. After 50 minutes of resting, dialysate glucose and lactate levels were 1.84±0.05 mM and 1.67±0.03 mM respectively.

To guard against possible changes in probe recovery, a ratio of the two metabolites was also calculated. The lactate/glucose ratio increased with exercise, and rose more steeply with increasing cycling intensity. Interestingly, the lactate/glucose ratio continued to increase considerably, even after exercise had stopped.

An overview of the dialysate glucose and lactate levels and the lactate/glucose ratio throughout the cycling protocol for two cyclists is shown in FIG. 17-D. The overall trends in glucose and lactate levels are similar for the two cyclists, although the absolute concentrations appear quite different. This variability could be caused by changes in probe recovery or by differences in the fitness levels of the cyclists. In principle, level changes caused by differences in probe recovery would have been removed using ratios of analyte concentrations, such as the lactate/glucose ratio.[15] Such ratios are widely used for monitoring in the injured human brain (lactate/pyruvate)[40] and in muscle (lactate/pyruvate and lactate/glucose),[41] though this needs to be further investigated for subcutaneous tissue. Nevertheless, there are clear differences in the lactate/glucose ratio trend for the two cyclists.

We have demonstrated the first example of a 3D printed microfluidic device with integrated removable biosensors that joins directly to a clinical microdialysis probe for continuous human monitoring applications. Here we have demonstrated its capabilities as a wearable device for subcutaneous monitoring of tissue glucose and lactate levels in cyclists during exercise. The clear changes recorded in the local glucose and lactate levels indicate that this device could have huge potential for monitoring and evaluating athlete training effectiveness in real-time. Moreover, this miniaturized device also has potential for clinical microdialysis applications, such as bedside monitoring, as its wearable nature removes the need for long connection tubing, which usually leads to long lag times.

Due to the dimensional control provided by 3D printing, it was possible to design the microfluidic device so that it could easily be integrated with commercially available microdialysis probes, making it suitable for numerous potential applications. Future work will focus on miniaturization of the wireless potentiostats to enable integration of the electronics within the wearable device. Due to the modular nature of the device, the platform can be expanded to include monitoring of other clinically-relevant biomarkers, offering promise in a wide range of clinical and fitness applications.

REFERENCES (1) Body Sensor Networks; Yang, G.-Z., Ed.; Springer, 2014.
(2) Matzeu, G.; Florea, L.; Diamond, D. *Sensors Actuators B Chem.* 2015, 211, 403-418.
(3) Diamond, D.; Coyle, S.; Scarmagnani, S.; Hayes, J. *Chem. Rev.* 2008, 108, 652-679.
(4) Windmiller, J. R.; Wang, J. *Electroanalysis* 2013, 25, 29-46.
(5) Woderer, S.; Henninger, N.; Garthe, C. D.; Kloetzer, H. M.; Hajnsek, M.; Kamecke, U.; Gretz, N.; Kraenzlin, B.; Pill, J. *Anal. Chim. Acta* 2007, 581, 7-12.
(6) Facchinetti, A.; Sparacino, G.; Cobelli, C. *J. diabetes Sci. Technol.* 2007, 1, 617-623.
(7) Curto, V. F.; Fay, C.; Coyle, S.; Byrne, R.; O'Toole, C.; Barry, C.; Hughes, S.; Moyna, N.; Diamond, D.; Benito-Lopez, F. *Sensors Actuators B Chem.* 2012, 171-172, 1327-1334.
(8) Jia, W.; Bandodkar, A. J.; Valde, G.; Windmiller, J. R.; Yang, Z.; Ram, J.; Chan, G.; Wang, J. *Anal. Chem.* 2013, 85, 6553-6560.
(9) Kabilan, S.; Ph, D.; Lowe, C. *Diabetes Technol. Ther.* 2006, 8, 89-93.
(10) Iguchi, S.; Kudo, H.; Saito, T.; Ogawa, M.; Saito, H.; Otsuka, K.; Funakubo, A.; Mitsubayashi, K. *Biomed. Microdevices* 2007, 9, 603-609.
(11) Yoda, K.; Shimazaki, K.; Ueda, Y. *Ann. N. Y Acad. Sci.* 1998, 864, 600-604.
(12) Mannoor, M. S.; Tao, H.; Clayton, J. D.; Sengupta, A.; Kaplan, D. L.; Naik, R. R.; Verma, N.; Omenetto, F. G.; McAlpine, M. C. Graphene-based wireless bacteria detection on tooth enamel. *Nature Communications,* 2012, 3, 763.
(13) Krustrup, P.; Mohr, M.; Steensberg, A.; Bencke, J.; Kjaer, M.; Bangsbo, J. *Med. Sci. Sports Exerc.* 2006, 38, 1165-1174.
(14) Watson, C. J.; Venton, B. J.; Kennedy, R. T. *Anal. Chem.* 2006, 78, 1391-1399.
(15) Parkin, M. C.; Hopwood, S. E.; Boutelle, M. G.; Strong, A. J. *TrAC Trends Anal. Chem.* 2003, 22, 487-497.
(16) Schultz, K. N.; Kennedy, R. T. *Annu. Rev. Anal. Chem.* 2008, 1, 627-661.
(17) Nandi, P.; Lunte, S. M. *Anal. Chim. Acta* 2009, 651, 1-14.
(18) Rogers, M. L.; Brennan, P. A.; Leong, C. L.; Gowers, S. A. N.; Aldridge, T.; Mellor, T. K.; Boutelle, M. G. *Anal. Bioanal. Chem.* 2013, 405, 3881-3888.
(19) Rogers, M. L.; Feuerstein, D.; Leong, C. L.; Takagaki, M.; Niu, X.; Graf, R.; Boutelle, M. G. *ACS Chem. Neurosci.* 2013, 4, 799-807.
(20) Deeba, S.; Corcoles, E. P.; Hanna, G. B.; Hanna, B. G.; Pareskevas, P.; Aziz, O.; Boutelle, M. G.; Darzi, a. *Dis. Colon Rectum* 2008, 51, 1408-1413
(21) Birke-Sorensen, H. J. *Transplant.* 2012, 2012, 970630.
(22) Wang, M.; Roman, G. T.; Schultz, K.; Jennings, C.; Kennedy, R. T. *Anal. Chem.* 2008, 80, 5607-5615.
(23) Sun, S.; Slaney, T. R.; Kennedy, R. T. *Anal. Chem.* 2012, 84, 5794-5800.
(24) Nandi, P.; Desai, D. P.; Lunte, S. M. *Electrophoresis* 2010, 31, 1414-1422.
(25) Lucca, B. G.; Lunte, S. M.; Tomazelli Coltro, W. K.; Ferreira, V. S. *Electrophoresis* 2014, 35, 3363-3370.
(26) Rogers, M.; Leong, C.; Niu, X.; de Mello, A.; Parker, K. H.; Boutelle, M. G. *Phys. Chem. Chem. Phys.* 2011, 13, 5298-5303.
(27) Taylor, G. Proc. R. *Soc. Lond. A. Math. Phys. Sci.* 1953, 219, 186-203.
(28) Lunte, S. M.; Nandi, P.; Regel, A.; Grigsby, R.; Hulvey, M. K.; Scott, D.; Naylor, E.; Gabbert, S.; Johnson, D. In *14th International Conference on Miniaturized Systems for Chemistry and Life Sciences;* 2010; pp. 1535-1537.
(29) Erkal, J. L.; Selimovic, A.; Gross, B. C.; Lockwood, S. Y.; Walton, E. L.; McNamara, S.; Martin, R. S.; Spence, D. M. *Lab Chip* 2014, 14, 2023-2032.
(30) Kitson, P. J.; Rosnes, M. H.; Sans, V.; Dragone, V.; Cronin, L. *Lab Chip* 2012, 12, 3267.
(31) Therriault, D.; White, S. R.; Lewis, J. a. *Nat. Mater.* 2003, 2, 265-271.
(32) Snowden, M. E.; King, P. H.; Covington, J. a; Macpherson, J. V; Unwin, P. R. *Anal. Chem.* 2010, 82, 3124-3131.
(33) Anderson, K. B.; Lockwood, S. Y.; Martin, R. S.; Spence, D. M. *Anal. Chem.* 2013, 85, 5622-5626.
(34) Waldbaur, A.; Rapp, H.; Länge, K.; Rapp, B. E. *Anal. Methods* 2011, 3, 2681.
(35) Patel, B. A.; Rogers, M.; Wieder, T.; O'Hare, D.; Boutelle, M. G. *Biosens. Bioelectron.* 2011, 26, 2890-2896.
(36) Viggiano, A.; Marinesco, S.; Pain, F.; Meiller, A.; Gurden, H. *J. Neurosci. Methods* 2012, 206, 1-6.
(37) Vasylieva, N.; Barnych, B.; Meiller, A.; Maucler, C.; Pollegioni, L.; Lin, J.-S.; Barbier, D.; Marinesco, S. *Biosens. Bioelectron.* 2011, 26, 3993-4000.
(38) Feuerstein, D.; Parker, K. H.; Boutelle, M. G. *Anal. Chem.* 2009, 81, 4987-4994.
(39) Heinonen, I.; Kalliokoski, K. K.; Hannukainen, J. C.; Duncker, D. J.; Nuutila, P.; Knuuti, J. *Physiology (Bethesda).* 2014, 29, 421-436.
(40) Timofeev, I.; Carpenter, K. L. H.; Nortje, J.; Al-Rawi, P. G.; O'Connell, M. T.; Czosnyka, M.; Smielewski, P.; Pickard, J. D.; Menon, D. K.; Kirkpatrick, P. J.; Gupta, a. K.; Hutchinson, P. J. *Brain* 2011, 134, 484-494.
(41) Kristensen, D. L.; Ladefoged, S. a; Sloth, E.; Aagaard, R.; Birke-Sørensen, H. Br. *J. Oral Maxillofac. Surg.* 2013, 51, 117-122

Aspects of the invention also provide:
1. A sensor comprising at least one working electrode, at least one auxiliary electrode, and at least one reference electrode,
  wherein the sensor comprises a hydrogel layer that extends over the said at least one working electrode, auxiliary electrode and reference electrode.
2. The sensor of aspect 1 wherein the sensor is for use as an amperometric sensor.
3. The sensor according to any of aspects 1 or 2 wherein the hydrogel layer comprises one or more enzymes, for example an oxidase, for example an oxidase that produces hydrogen peroxide.
4. The sensor according to aspect 3 wherein the one or more enzymes include lactate oxidase, glucose oxidase, pyruvate oxidase, choline oxidase, hexokinase or horseradish peroxidase.

5. The sensor according to any one of aspects 1-4 wherein the at least one working electrode has a first coating layer, optionally wherein the first coating layer comprises a coating of a dense polymeric film, optionally wherein the dense polymeric film is poly-m-phenylenediamine (PPD) or polyphenol.

6. The sensor according to aspect 5 wherein the first layer allows $H_2O_2$ but not enzymes or smaller interferent molecules that could be oxidased by the electrode at the same potential to give a current, optionally ascorbic acid or neurotransmitters, to contact the electrode.

7. The sensor according to aspect 5 or 6 wherein the first layer protects against poisoning of the working electrode function, optionally by poisoning of the electrochemical transduction reaction.

8. The sensor according to any of aspects 5 to 7 wherein the first layer assists in protecting against fouling.

9. The sensor according to any of aspects 1-8 wherein the at least one working electrode, and optionally at least one auxiliary electrode and at least one reference electrode, are coated in an further layer outside the hydrogel layer, optionally wherein the further layer is polyurethane.

10. The sensor according to any of aspects 1-9 wherein the auxiliary electrode comprises or consists of a metal shaft, optionally a hollow metal shaft, optionally a hollow needle.

11. The sensor according to aspect 10 wherein the at least one working electrode and the at least one reference electrode are located inside the hollow metal shaft of the auxiliary electrode.

12. The sensor according to any of aspects 1-11 wherein the distal tip of the sensor has an angled surface such that it produces a sharp point to enable the sensor to pierce a polymeric fluidic chamber, optionally angled between 90 degrees and 30 degrees to the longest end of the sensor, optionally angled to a degree to allow contact with the far side of the sensor and accurate placement of the electrodes within a polymeric fluidic chamber.

13. The sensor according to any of aspects 1-12 wherein the hydrogel layer allows detection of a metabolite, optionally allows detection of lactate or glucose or pyruvate.

14. The sensor according to any of aspects 1-13 wherein the hydrogel layer aids in reducing electrical disconnection of one or more electrodes due to multi-phase flow, for example air bubbles or non-aqueous carrier liquid within the fluid flow.

15. The sensor according to any of aspects 1-14 wherein the third layer extends the dynamic range and increases the sensitivity of the sensor.

16. The sensor according to any of aspects 1-15 wherein the hydrogel layer comprises albumin, and/or electrochemical mediator reagents, and horseradish peroxidase.

17. The sensor according to any of aspects 1-16 wherein the hydrogel extends only over the distal end of the at least one working electrode, auxiliary electrode and reference electrode.

18. A lactate sensor comprising a sensor according to any of aspects 1-17, wherein the hydrogel comprises lactate oxide.

19. A glucose sensor comprising a sensor according to any of aspects 1-17, wherein the hydrogel comprises glucose oxidase.

20. A pyruvate sensor comprising a sensor according to any of aspects 1-17, wherein the hydrogel comprises pyruvate oxidase.

21. A pyruvate sensor comprising at least one working electrode, at least one auxiliary electrode, and at least one reference electrode, wherein the sensor does not comprise a hydrogel layer that extends over the said at least one working electrode, auxiliary electrode and reference electrode.

22. A sensing reagent comprising pyruvate oxidase, TPP (Thyamine Pyrophosphate), and a divalent cation.

23. The sensing reagent according to aspect 22 wherein the reagent comprises a buffer, optionally PBS, citrate buffer or HEPES.

24. The sensing reagent according to any one of aspects 22 and 23 wherein the reagent is at a pH between 5 and 8, optionally at a pH between 6.0, 6.1, 6.2, 6.3, 6.4, 6.5, 6.6, 6.7, 6.8, 6.9, 7.0, 7.1, 7.2 or 7.3 and 8.0, 7.9, 7.8, 7.7, 7.6, or 7.5, optionally between pH 6.5 and 7.5, optionally between pH 6.8 and 7.5 optionally pH 7.4.

25. The sensing reagent according to any one of aspects 22 to 24 wherein the concentration of the pyruvate oxidase is such as to provide a concentration of 0.06 mg/ml to 12 mg/ml pyruvate oxidase, optionally 1 to 8 mg/ml, optionally 6 mg/ml of added pyruvate oxidase in the sensing reaction solution.

26. The sensing reagent according to any of aspects 22-25 wherein the divalent cation is Mn2+, Ca2+, Co2+ or Mg2+, and optionally the concentration of the divalent cation, optionally $Mg^{2+}$, optionally $MgCl_2$ is such as to provide a concentration of 0.0 mM to 20 mM, optionally 16.8 mM of added divalent cation in the sensing reaction solution.

27. The sensing reagent according to any of aspects 22-26 wherein the concentration of the TPP is such as to provide a concentration of 0.01 to 8.0 mM TPP, or 2.0 to 6.0 mM TPP, optionally 4.8 mM of added TPP in the sensing reaction solution.

28. The sensing reagent according to any of aspects 22 to 27 wherein the reagent is concentrated relative to the intended sensing reaction solution, optionally concentrated such that a concentration of 0.06 mg/ml to 18 mg/ml pyruvate oxidase, 0.04 mM to 60 mM divalent cation, optionally MgCl2 and 0.5 to 20 mM TPP, optionally 6 mg/ml pyruvate oxidase, 16.8 mM MgCl2, 4.8 mMTPP is obtained in the sensing reaction solution.

29. The sensing reagent according to any of aspects 22-28 wherein the reagent comprises 0.3 mg/ml to 80 mg/ml pyruvate oxidase, 0.2 mM to 70 mM divalent cation, optionally Mg2+, 0.06 to 15 mM TPP, optionally 30 mg/ml pyruvate oxidase, 21 mM Mg2+, 6 mM TPP or 60 mg/ml pyruvate oxidase, 42 mM Mg2+, 12 mM TPP.

30. A sensor system comprising one or more sensors according to any one of aspects 1-21, optionally wherein the sensor is a biosensor.

31. The sensor system according to aspect 30 further comprising a sensing reagent.

32. The sensor system according to any of aspects 30 and 31 comprising a sensing reagent comprising pyruvate oxidase.

33. The sensor system according to any of aspects 31 and 32 wherein the sensing reagent comprises pyruvate oxidase, TPP, a divalent cation optionally $MgCl_2$ and a buffer optionally PBS, citrate buffer or HEPES.

34. The sensor system according to any of aspects 31 to 33 wherein the sensing reagent is as defined in any of aspects 22-29.

35. The sensor system according to any of aspects 30-34 wherein the hydrogel of one or more of the sensors comprises one or more enzymes immobilised in the hydrogel layer.

36. The sensor system according to any of aspects 30-35 wherein the hydrogel of one or more of the sensors does not comprise an enzyme immobilised in the hydrogel layer.

37. The sensor system according to any of aspects 30-36 comprising two or more sensors according to any of aspects 1-21.
38. The sensor system according to any of aspects 30-37 wherein at least one sensor is for the detection of lactate, optionally wherein the hydrogel of at least one sensor comprises lactate oxidase.
39. The sensor system according to any of aspects 30-38 wherein at least one sensor is for the detection of pyruvate.
40. The sensor system according to any of aspects 30-39 wherein at least one sensor is for the detection of glucose, optionally wherein the hydrogel of at least one sensor comprises glucose oxidase.
41. The sensor system according to any of aspects 30-35 comprising a microfluidic circuit, comprising a microfluidic device.
42. The sensor system according aspect 41 wherein the microfluidic circuit or microfluidic device is adapted for insertion of the sensor or sensors.
43. The sensor system according to any one of aspects 41 and 42 wherein the microfluidic circuit or microfluidic device is adapted for addition of a sensing reagent, microdialysate fluid and/or calibration fluid.
44. The sensor system according to any of aspects 30-43 wherein the sensing end of the one or more sensors is positioned in the middle of the channel of the microfluidic device.
45. The sensor system according to any of aspects 30-44 wherein the system further comprises a means of controlling the placement of the sensor within the microfluidic device.
46. The sensor system according to any of aspects 30-45 comprising a microdialysis probe and optionally a continuous flow system, optionally wherein the microdialysis probe is a Brain CMA-70 (from MDialysis); a Freeflap CMA-70 (from MDialysis); a MAB9.14.2 (Microbiotech SE); MAB6.14.2 (Microbiotech SE); or MAB11.35.4 (Microbiotech SE).
47. The sensor system according to any one of aspects 30 to 46 comprising a means for maintaining a steady flow.
48. The sensor system according to aspect 47 wherein the means for maintaining a steady flow are as defined in relation to any one of claims 1 to 51.
49. The sensor system according to any of aspects 30-48 further comprising calibration standards.
50. The sensor system according to any of aspects 30-49 further comprising horseradish peroxidase and an electrochemical mediator, optionally ferrocene.
51. A method for the analysis of dialysate from a human or animal subject, the method comprising detection of a metabolite using a sensor according to any one of aspects 1-21 or the sensor system according to any of aspects 30-50.
52. The method according to aspect 51 wherein the metabolite is lactate, and wherein the hydrogel of one or more of the amperometric sensors comprises lactate oxidase.
53. The method according to aspect 51 wherein the metabolite is glucose, and wherein the hydrogel of one or more of the amperometric sensors comprises glucose oxidase.
54. The method according to aspect 51 wherein the metabolite is pyruvate and wherein the hydrogel of one or more of the amperometric sensors comprises pyruvate oxidase.
55. The method according to aspect 51 wherein glucose, and/or lactate, and/or pyruvate are analysed in the dialysate, optionally wherein the relative levels of two or more of glucose, lactate and pyruvate are determined.
56. The method according to any one of aspects 51-55 wherein the dialysate is a microdialysate.
57. The method according to aspect 56 wherein the microdialysate is extracted from the subject in a continuous flow.
58. The method according to aspect 56 or 57 wherein the microdialysate is analysed in a polymeric microfluidic chamber.
59. The method according to aspect 58 wherein the flow of the microdialysate into the polymeric microfluidic chamber is controlled, optionally controlled by a system as defined in relation to any one of aspects 1 to 51.
60. The method according to any of aspects 51-59 wherein the sensor continuously monitors the metabolite for at least one, two, three, four, five, six or more days, optionally with interruptions for calibration, optionally of up to about 60, 50, 40, 30, 20 or 10 minutes, optionally with calibration occurring at intervals of between 0.5 and 12 hours.
61. A method for detecting the amount of pyruvate in the dialysate from a human or animal comprising:
   adding a sensing reagent for the sensing of pyruvate to the dialysate,
   contacting the dialysate and sensing reagent with a sensor according to any one of aspects 1-21, or the sensor system according to any one of aspects 30-50, wherein the hydrogel does not comprise an enzyme.
62. The method according to aspect 61 wherein the sensing reagent is as defined in aspects 22-29.
63. The method according to any of aspects 61 or 62 wherein the sensing reagent is sufficient for essentially complete conversion of pyruvate to acetyl phosphate+$CO_2$+$H_2O_2$.
64. The method according to any of aspects 61-63 wherein the sensing reagent is added prior to contacting the dialysate with the sensor, optionally wherein the sensing reagent is added at least 1, 2, 5, 10, 20, 25 or 30 seconds prior to contact with the sensor.
65. The method according to any one of aspects 61-64 further comprising:
   taking multiple readings over a period of time, optionally over 1 hour, 4 hours, 12 hours, 24 hours, 48 hours, 72 hours or longer, optionally taking multiple readings of more than one metabolite, optionally taking multiple readings of the levels or ratios of lactate, pyruvate and glucose
   comparing the readings and determining a change in levels of metabolite.

The invention claimed is:
1. A microfluidic flow controller comprising:
   a fluid source connector for receiving analyte fluid;
   a first valve having: (i) a first inlet coupled to the fluid source connector, (ii) a first outlet coupled to an analyte conduit for coupling to an analysis module; and (iii) a second outlet coupled to a drain conduit;
   a second valve having a first port coupled to a first pump and a second port coupled to a calibration fluid source inlet and an outlet coupled to the analyte conduit;
   a controller configured to substantially simultaneously:
      a) switch the first valve between: (i) an analysis mode in which the first inlet is fluidly coupled to the first outlet, and (ii) a divert mode in which the first inlet is fluidly coupled to the second outlet; and
      b) switch the second valve between (i) a standby mode in which delivery of calibration fluid to the analyte conduit is blocked and (ii) a calibration mode in which the second valve is configured to deliver calibration fluid to the analyte conduit,
   the flow controller being thereby configured to maintain a constant flow rate of fluid through the analyte conduit during both the analysis mode and the calibration mode, and the second valve being configured such that in the standby mode the first and second ports are fluidly coupled to one another and in the calibration mode the first pump is fluidly coupled to the analyte conduit.

2. The microfluidic flow controller of claim 1 further including a third valve coupled to a second calibration fluid source inlet and having an outlet coupled to the analyte conduit,
the controller being configured to switch the third valve between (i) a standby mode in which delivery of second calibration fluid to the analyte conduit is blocked and (ii) a calibration mode in which the third valve is configured to deliver calibration fluid to the analyte conduit, the switching being substantially simultaneous with the switching of the first and second valves such that the standby modes of the second and third valves coincide and the calibration modes of the second and third valves coincide.

3. The microfluidic flow controller of claim 2 in which the third valve further includes a first port and a second port, the first port being coupled to a second pump and the second port being coupled to a second calibration fluid source inlet,
the third valve being configured such that in the standby mode the first and second ports are fluidly coupled to one another and in the calibration mode the second pump is fluidly coupled to the analyte conduit.

4. The microfluidic flow controller of claim 2 further including a second reservoir of calibration fluid coupled to the second calibration fluid source inlet.

5. The microfluidic flow controller of claim 1 in which the first pump is a piston pump and the controller is further configured to activate the first pump to charge via the second port of the second valve when the second valve is in the standby mode and to discharge via the second valve outlet when the second valve is in the calibration mode.

6. The microfluidic flow controller of claim 1 in which the second valve is coupled to the calibration source inlet via a pump.

7. The microfluidic flow controller of claim 1 further including an analysis module fluidly coupled to the analyte conduit.

8. The microfluidic flow controller of claim 1 further including a first reservoir of calibration fluid coupled to the calibration fluid source inlet.

9. The microfluidic flow controller of claim 1 further including a collection vessel fluidly coupled to the drain conduit for receiving analyte when the first valve is in the divert mode.

10. The microfluidic flow controller of claim 1 in which the controller is further configured to periodically switch from the analysis mode to the calibration mode.

11. The microfluidic flow controller of claim 10 further including a reservoir of flush fluid coupled to the flush fluid source inlet.

12. The microfluidic flow controller of claim 1 further including a flush valve coupled to a flush fluid source inlet and having an outlet coupled to the analyte conduit, the controller being further configured to switch the flush valve between (i) a standby mode in which delivery of flush fluid to the analyte conduit is blocked and (ii) a flush mode in which the flush valve is configured to deliver flush fluid to the analyte conduit and in which the first valve is switched to a divert mode in which the first inlet is fluidly coupled to the second outlet,
the flow controller being thereby configured to enable a flush fluid to pass through the analyte conduit to clear gas bubbles and obstructions from the analyte conduit.

13. The microfluidic flow controller of claim 12 in which the flush valve further includes a first port and a second port, the first port being coupled to a flush pump and the second port being coupled to the flush fluid source inlet,
the flush valve being configured such that in the standby mode the first and second ports are fluidly coupled to one another and in the flush mode the flush pump is fluidly coupled to the analyte conduit.

14. The microfluidic flow controller of claim 13 further including a reagent valve coupled to a reagent fluid source inlet and having an outlet coupled to the analyte conduit, the controller being further configured to switch the reagent valve between (i) a standby mode in which delivery of reagent to the analyte conduit is blocked and (ii) an analysis mode in which the reagent valve is configured to deliver reagent to the analyte conduit.

15. The microfluidic flow controller of claim 14 in which the reagent valve further includes a first port and a second port, the first port being coupled to a reagent pump and the second port being coupled to the reagent fluid source inlet,
the flush valve being configured such that in the standby mode the first and second ports are fluidly coupled to one another and in the analysis mode the flush pump is fluidly coupled to the analyte conduit,
the switching being substantially simultaneous with the switching of the first and second valves such that the analysis modes of the first valve and the reagent valve coincide and the divert mode of the first valve and the standby mode of the reagent valve coincide.

16. The microfluidic flow controller of claim 15 further including a reservoir of reagent coupled to the reagent fluid source inlet.

17. The microfluidic flow controller of claim 14 in which the controller is configured to ensure that a combined flow rate of analyte fluid entering the analyte flow conduit from the fluid source connector and from the reagent valve during the analysis mode is matched to a flow volume of calibration fluid and reagent fluid entering the analyte flow conduit during the calibration mode.

18. A microfluidic fluid analysis apparatus comprising:
a fluid source connector for receiving analyte fluid;
a first calibration source inlet for coupling to a first reservoir for a first calibration fluid;
a second calibration source inlet for coupling to a second reservoir for a second calibration fluid;
an analysis module configured to receive fluid for analysis;
a first pump for delivering said first calibration fluid and a second pump for delivering said second calibration fluid to the analysis module;
a controller configured to (i) fluidly couple the fluid source connector to the analysis module, fluidly couple the first calibration source inlet to the first pump, and fluidly couple the second calibration source inlet to the second pump during an analysis mode; and (ii) deliver the first and second calibration fluids from the first and second pumps, respectively, to the analysis module during a calibration mode;
the controller being further configured to vary the ratio of flow rates of the first and second calibration fluids to the analysis module during the calibration mode, in which the controller is configured to periodically implement a calibration routine comprising:
operating the controller to deliver the first and second calibration fluids in a first ratio of volumes to the analysis module and subsequently to deliver at least the first and second calibration fluids in a second ratio of volumes, different from the first ratio, to the analysis module;

the apparatus further including a calibration processor configured to determine a calibration profile derived from the ratios of calibration fluids and an output from the analysis module, and in which the controller is configured to implement the calibration routine periodically at intervals of between 0.5-12 hours.

19. The microfluidic fluid analysis apparatus of claim 18 further including a first calibration fluid reservoir coupled to supply said first pump and a second calibration fluid reservoir coupled to supply said second pump.

20. The microfluidic fluid analysis apparatus of claim 18 in which the controller is configured to implement the calibration routine periodically based on a rate of change of the calibration profile.

21. The microfluidic fluid analysis apparatus of claim 18 in which the controller is further configured to isolate the fluid source connector and the analysis module when the controller is in in the calibration mode.

22. The microfluidic fluid analysis apparatus of claim 18 further configured to issue an alert signal based on the determined calibration profile, which indicates an expiry time of the analysis module.

* * * * *